United States Patent
Guevremont et al.

(10) Patent No.: US 7,034,286 B2
(45) Date of Patent: Apr. 25, 2006

(54) FAIMS APPARATUS HAVING PLURAL ION INLETS AND METHOD THEREFORE

(75) Inventors: Roger Guevremont, Ottawa (CA); Randy Purves, Orleans (CA); David Barnett, Orleans (CA); Kevin Mansfield, Ottawa (CA)

(73) Assignee: Ionalytics Corporation, Ottawa (CA)

(*) Notice: Subject to any disclaimer, the term of this patent is extended or adjusted under 35 U.S.C. 154(b) by 110 days.

(21) Appl. No.: 10/861,518

(22) Filed: Jun. 7, 2004

(65) Prior Publication Data

US 2004/0232326 A1    Nov. 25, 2004

Related U.S. Application Data

(63) Continuation-in-part of application No. 10/359,642, filed on Feb. 7, 2003, now Pat. No. 6,753,522.

(60) Provisional application No. 60/505,868, filed on Sep. 26, 2003, provisional application No. 60/354,711, filed on Feb. 8, 2002.

(51) Int. Cl.
*H01J 49/40* (2006.01)

(52) U.S. Cl. ............ 250/282; 250/281; 250/288; 250/287; 250/286; 250/283; 250/292

(58) Field of Classification Search ......... 250/281–288
See application file for complete search history.

(56) References Cited

U.S. PATENT DOCUMENTS

| | | | |
|---|---|---|---|
| 5,420,424 | A | 5/1995 | Carnahan et al. |
| 5,905,258 | A | 5/1999 | Clemmer et al. |
| 6,621,077 | B1 | 9/2003 | Guevremont et al. |
| 6,639,212 | B1 | 10/2003 | Guevremont et al. |
| 6,713,758 | B1 * | 3/2004 | Guevremont et al. ....... 250/290 |
| 2003/0150984 | A1 * | 8/2003 | Guevremont et al. ....... 250/281 |
| 2005/0145789 | A1 * | 7/2005 | Miller et al. ................ 250/290 |

FOREIGN PATENT DOCUMENTS

| | | |
|---|---|---|
| WO | WO 00/08455 A1 | 2/2000 |
| WO | WO 00/63949 A1 | 10/2000 |
| WO | WO 01/44795 A2 | 6/2001 |

(Continued)

OTHER PUBLICATIONS

Carr et al., "Plasma Chromatography", Plenum Press (1984), NY, USA.

(Continued)

*Primary Examiner*—Nikita Wells
*Assistant Examiner*—Johnnie L Smith, II
(74) *Attorney, Agent, or Firm*—Freedman & Associates

(57) ABSTRACT

An apparatus for multiplexing ions from a plurality of ionization sources includes a FAIMS analyzer including an inner electrode and an outer electrode, the outer electrode having a plurality of spaced-apart ion inlet orifices and a single ion outlet orifice. A plurality of non-trapping FAIMS analyzers is disposed adjacent to the FAIMS analyzer. Each non-trapping FAIMS analyzer of the plurality of non-trapping FAIMS analyzers has a single ion outlet orifice in communication with one ion inlet orifice of the plurality of ion inlet orifices of the FAIMS analyzer, and each non-trapping FAIMS analyzer has a single ion inlet orifice for supporting introduction of ions into the non-trapping FAIMS. An electrical controller is provided in communication with the FAIMS, for providing conditions within the FAIMS for supporting transmission of at least some of the ions introduced into the FAIMS from one of the non-trapping FAIMS and for not supporting transmission of substantially all of the ions introduced simultaneously into the FAIMS from the other one of the non-trapping FAIMS.

55 Claims, 40 Drawing Sheets

FOREIGN PATENT DOCUMENTS

WO WO 01/69217 A2 9/2001
WO WO 01/69221 A2 9/2001

OTHER PUBLICATIONS

Mason et al., "Transport Properties of Ions in Gases", Wiley (1988), NY, USA.

Buryakov et al., "A New Method of Separation of Multi-Atomic Ions by Mobility at Atmospheric Pressure using a High-Frequency Amplitude-Asymmetric Strong Electric Field", Int. J. Mass Spectrom. Ion Processes, No. 128, pp.143-148, Elsevier Science Publishers B.V. (1993).

Eiceman et al., "Ion Mobility Spectrometry", (1994), CRC Press, FL, USA.

Carnahan et al., "Field Ion Spectrometry—A New Analytical Technology for Trace Gas Analysis", Proceedings of the 41st Annual ISA Analysis Division Symposium, paper #96-009, pp. 87-95, (1996), Framingham, MA, USA.

Riegner et al., "Qualitative Evaluation of Field Ion Spectrometry for Chemical Warfare Agent Detection", Proceedings of the 45th ASMS Conference on Mass Spectrometry and Allied Topics, pp. 473, (1997), Palm Springs, CA, USA.

Krylov, "A Method of Reducing Diffusion Losses in a Drift Spectrometer", Tech. Phys., vol. 44, No. 1, pp. 113-116, American Institute of Physics (1999).

Spangler, "Fundamental Considerations for the Application of Miniature Ion Mobility Spectrometry to Field Analytical Applications", Field Analytical Chemistry and Technology, 4, pp. 225-267 (2000), USA.

Eiceman et al., "Monitoring Volatile Organic Compounds in Ambient Air Anside and Outside Buildings with the use of a Radio-Frequency-Based Ion-Mobility Analyzer with a Micromachined Drift Tube", Field Analytical Chemistry and Technology, 4, pp. 297-308 (2000), USA.

Miller et al., "A Novel Micromachined High-Field Asymmetric Waveform-Ion Mobility Spectrometer", Sensors and Actuators B Chemical, 67, pp. 300-306, Elsevier Science S.A. (2000).

Miller et al., "A MEMS Radio-Frequency Ion Mobility Spectrometer for Chemical Vapor Detection", Sensors and Actuators A Physical, 91, pp. 307-318, Elsevier Science S.A. (2000).

Eiceman et al., "Miniature Radio-Frequency Mobility Analyzer as a Gas Chromatographic Detector for Oxygen-Containing Volatile Organic Compounds, Pheromones and other Insect Attractants", Journal of Chromatography A, 917, pp. 205-217, Elsevier Science B.V. (2001).

Buryakov et al., "Detection of Explosive Vapors in the Air Using an Ion Drift Nonlinearity Spectrometer", Journal of Analytical Chemistry, vol. 56, No. 4, pp. 336-340 (2001).

Guevremont et al., "Atmospheric Pressure Ion Trapping in a Tandem FAIMS—FAIMS Coupled to a TOFMS: Studies with Electrospray Generated Gramicidin S ions", Journal of the American Society for Mass Spectrometry, vol. 12, pp. 1320-1330, Elsevier Science Inc. (2001).

Spangler et al., "Application of Mobility Theory to the Interpretation of Data Generated by Linear and RF Excited Ion Mobility Spectrometers", International Journal of Mass Spectrometry, 12017, pp. 1-10, Elsevier Science B.V. (2002).

* cited by examiner

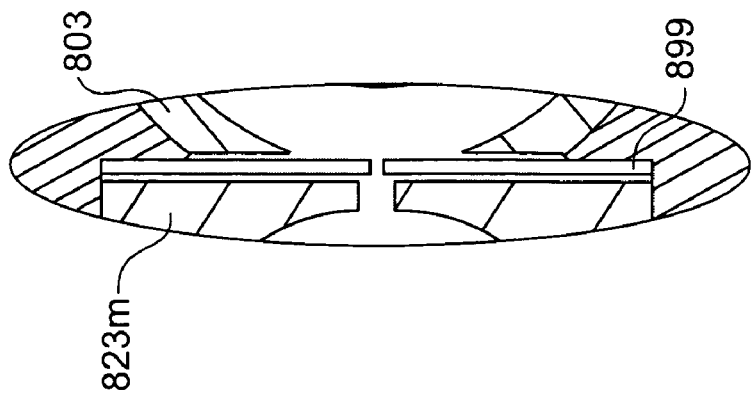
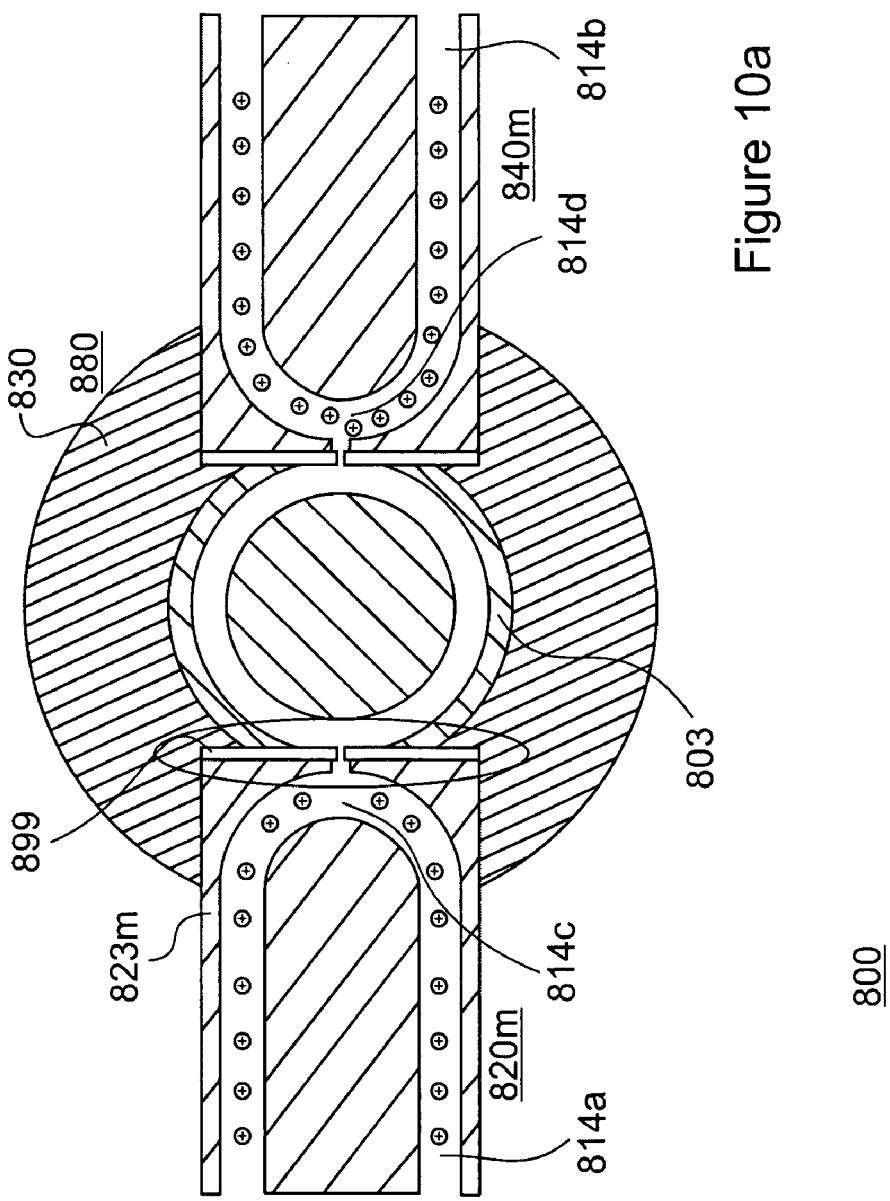
Figure 10a
Figure 10b

FAIMS APPARATUS HAVING PLURAL ION INLETS AND METHOD THEREFORE

CROSS-REFERENCE TO RELATED APPLICATIONS

This application is a continuation-in-part of U.S. application Ser. No. 10/359,642, filed Feb. 07, 2003 Now U.S. Pat. No. 6,753,522, which claims the benefit of U.S. Provisional Application No. 60/354,711 filed Feb. 08, 2002. This application also claims the benefit of U.S. Provisional Application No. 60/505,868 filed Sep. 26, 2003.

FIELD OF THE INVENTION

The instant invention relates generally to high field asymmetric waveform ion mobility spectrometry (FAIMS). In particular, the instant invention relates to an apparatus and method for multiplexing ion streams from a plurality of separate ionization sources through a single orifice.

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994), the contents of which are incorporated by reference herein. In IMS, gas-phase ion mobilities are determined using a drift tube with a constant electric field. Ions are separated in the drift tube on the basis of differences in their drift velocities. At low electric field strength, for example 200 V/cm, the drift velocity of an ion is proportional to the applied electric field strength, and the mobility, K, which is determined from experimentation, is independent of the applied electric field. Additionally, in IMS the ions travel through a bath gas that is at sufficiently high pressure that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988), the contents of which are incorporated by reference herein, teach that at high electric field strength, for instance fields stronger than approximately 5,000 V/cm, the ion drift velocity is no longer directly proportional to the applied electric field, and K is better represented by $K_H$, a non-constant high field mobility term. The dependence of $K_H$ on the applied electric field has been the basis for the development of high field asymmetric waveform ion mobility spectrometry (FAIMS). Ions are separated in a FAIMS analyzer on the basis of a difference in the mobility of an ion at high field strength, $K_H$, relative to the mobility of the ion at low field strength, K. In other words, the ions are separated due to the compound dependent behavior of $K_H$ as a function of the applied electric field strength.

In general, a device for separating ions according to the FAIMS principle has an analyzer region that is defined by a space between first and second spaced-apart electrodes. The first electrode is maintained at a selected dc voltage, often at ground potential, while the second electrode has an asymmetric waveform V(t) applied to it. The asymmetric waveform V(t) is composed of a repeating pattern including a high voltage component, $V_H$, lasting for a short period of time $t_H$ and a lower voltage component, $V_L$, of opposite polarity, lasting a longer period of time $t_L$. The waveform is synthesized such that the integrated voltage-time product, and thus the field-time product, applied to the second electrode during each complete cycle of the waveform is zero, for instance $V_H t_H + V_L t_L = 0$; for example +2000 V for 10 µs (microseconds) followed by −1000 V for 20 µs. The peak voltage during the shorter, high voltage portion of the waveform is called the "dispersion voltage" or DV, which is identically referred to as the applied asymmetric waveform voltage.

Generally, the ions that are to be separated are entrained in a stream of gas flowing through the FAIMS analyzer region, for example between a pair of horizontally oriented, spaced-apart electrodes. Accordingly, the net motion of an ion within the analyzer region is the sum of a horizontal x-axis component due to the stream of gas and a transverse y-axis component due to the applied electric field. During the high voltage portion of the waveform an ion moves with a y-axis velocity component given by $v_H = K_H E_H$, where $E_H$ is the applied field, and $K_H$ is the high field ion mobility under operating electric field, pressure and temperature conditions. The distance traveled by the ion during the high voltage portion of the waveform is given by $d_H = v_H t_H = K_H E_H t_H$, where $t_H$ is the time period of the applied high voltage. During the longer duration, opposite polarity, low voltage portion of the asymmetric waveform, the y-axis velocity component of the ion is $v_L = K E_L$, where K is the low field ion mobility under operating pressure and temperature conditions. The distance traveled is $d_L = v_L t_L = K E_L t_L$. Since the asymmetric waveform ensures that $(V_H t_H) + (V_L t_L) = 0$, the field-time products $E_H t_H$ and $E_L t_L$ are equal in magnitude. Thus, if $K_H$ and K are identical, $d_H$ and $d_L$ are equal, and the ion is returned to its original position along the y-axis on the completion of one cycle of the waveform. If at $E_H$ the mobility $K_H \neq K$, the ion experiences a net displacement from its original position relative to the y-axis. For example, if $K_H > K$, a positive ion travels farther during the positive portion of the waveform, for instance $d_H > d_L$. Then the ion migrates away from the second electrode and eventually will be neutralized at the first electrode.

In order to reverse the transverse drift of the positive ion in the above example, a constant negative dc voltage is applied to the second electrode. The difference between the dc voltage that is applied to the first electrode and the dc voltage that is applied to the second electrode is called the "compensation voltage" (CV). The CV voltage prevents the ion from migrating toward either the second or the first electrode. If ions derived from two compounds respond differently to the applied high strength electric fields, the ratio of $K_H$ to K may be different for each compound. Consequently, the magnitude of the CV that is necessary to prevent the drift of the ion toward either electrode is also different for each compound. Thus, when a mixture including several species of ions, each with a unique $K_H/K$ ratio, is being analyzed by FAIMS, only one species of ion is selectively transmitted to a detector for a given combination of CV and DV. In one type of FAIMS experiment, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained.

Guevremont et al. have described the use of curved electrode bodies, for instance inner and outer cylindrical electrodes, for producing a two-dimensional atmospheric pressure ion focusing effect that results in higher ion transmission efficiencies than can be obtained using, for example, a FAIMS device having parallel plate electrodes. In particular, with the application of an appropriate combination of DV and CV an ion of interest is focused into a band-like region in the annular gap between the cylindrical electrodes as a result of the electric fields, which change with radial distance. Focusing the ions of interest has the effect of reducing the number of ions of interest that are lost as a result of the ion suffering a collision with one of the inner and outer electrodes. FAIMS devices with cylindrical electrode geometry have been described in the prior art, as for example in U.S. Pat. No. 5,420,424, issued May 30, 1995 in the name of Carnahan et al., the contents of which are incorporated by reference herein.

In WO 00/08455, filed on Aug. 5, 1999, and in U.S. Pat. No. 6,504,149, issued Jan. 7, 2003, the contents of both of which are incorporated by reference herein, Guevremont and Purves describe a domed-FAIMS analyzer. In particular, the domed-FAIMS analyzer includes a cylindrical inner electrode having a curved surface terminus proximate an ion outlet orifice of the FAIMS analyzer region. The curved surface terminus is substantially continuous with the cylindrical shape of the inner electrode and is aligned co-axially with the ion outlet orifice. During use, the application of an asymmetric waveform to the inner electrode results in the normal ion-focusing behavior as described above, and in addition the ion-focusing action extends around the generally spherically shaped terminus of the inner electrode. This causes the selectively transmitted ions to be directed generally radially inwardly within the region that is proximate the terminus of the inner electrode. Several contradictory forces are acting on the ions in this region near the terminus of the inner electrode. The force of the carrier gas flow tends to influence the ions to travel towards the ion-outlet orifice, which advantageously also prevents the ions from migrating in a reverse direction, back towards the ion source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as described in greater detail by Guevremont and Purves in U.S. Pat. No. 6,621,007, issued on Sep. 16, 2003, the contents of which are incorporated by reference herein.

Guevremont and Purves further disclose a near-trapping mode of operation for the above-mentioned domed-FAIMS analyzer, which achieves ion transmission from the domed-FAIMS to a mass spectrometer with high efficiency. Under near-trapping conditions, the ions that accumulate in the three-dimensional region of space near the spherical terminus of the inner electrode are caused to leak from this region, being pulled by a flow of gas towards the ion-outlet orifice. The ions that are extracted from this region do so as a narrow, approximately collimated beam, which is pulled by the gas flow through the ion-outlet orifice and into a small orifice leading into the vacuum system of the mass spectrometer. Accordingly, a tandem domed-FAIMS/MS device is a highly sensitive instrument that is capable of detecting and identifying ions of interest at part-per-billion levels.

More recently, in WO 01/69216 the contents of which are incorporated by reference herein, Guevremont and Purves describe a so-called "perpendicular-gas-flow-FAIMS", which is identically referred to as a side-to-side FAIMS. The analyzer region of the side-to-side FAIMS is defined by an annular space between inner and outer cylindrical electrodes. In particular, ions that are introduced into the analyzer region of the side-to-side FAIMS are selectively transmitted in a direction that is generally around the circumference of the inner electrode. For instance, the ion inlet and the ion outlet of a side-to-side FAIMS device are disposed, one opposing the other, within a surface of the outer electrode such that ions are selectively transmitted through the curved analyzer region between the ion inlet and the ion outlet along a continuously curving ion flow path absent a portion having a substantially linear component. In particular, the ions travel from the ion inlet to the ion outlet by flowing around the inner electrode in one of a "clockwise" and a "counter clock-wise" direction. This is in contrast to the above-mentioned FAIMS devices in which the ions are selectively transmitted along the length of the inner electrode.

Advantageously, the side-to-side FAIMS device reduces the minimum distance that must be traveled by the ions within the analyzer region to approximately fifty per cent of the circumference of the inner electrode. Since the ions split into two streams traveling in opposite directions around the inner electrode after they are introduced through the ion inlet, the effective ion density within the analyzer region is reduced, and so too is the ion-ion repulsion space charge effect reduced. Furthermore, the reduction of the minimum ion travel distance has the added benefit of improving the ion transmission efficiency. For example, by keeping the time for travel short, the effect of diffusion and ion-ion repulsion forces are minimized. In keeping distances short, the transit time of the ions through the analyzer region is also short, which supports more rapid analysis of ion mixtures.

Of course, there are various drawbacks associated with state of the art side-to-side FAIMS devices, particularly relating to the efficient utilization of a FAIMS analyzer. The down time of a FAIMS analyzer often is determined not by limitations of the FAIMS device itself, but by the specifics of an ion source, or by requirements due to sample preparation. Additionally, Tandem-FAIMS devices comprising two FAIMS analyzers are known in the prior art; however, while ions are being accumulated in a first, trapping FAIMS analyzer, before being released to the second, continuous FAIMS analyzer, the second continuous FAIMS analyzer is "idling," and thus is not being fully utilized. It would therefore be highly advantageous to provide an apparatus that overcomes this problem of the prior art. For instance, a FAIMS analyzer that is in communication with a plurality of ion sources would allow for a more efficient utilization of the FAIMS analyzer. Advantageously, each ion source of the plurality of ion sources could be an embodiment of a different ionization technique. This would provide for an advanced method for optimizing ionization conditions for an unknown sample.

Furthermore, in conventional operation, a mass spectrometer is limited to one inlet aperture (orifice), due to limitations of pumping speed of the vacuum pumps that are connected to the low-pressure chamber, and because of the requirements of the ion optical components after the inlet aperture. It is a disadvantage that, in many experiments, including but not limited to liquid chromatographic separations, the mass spectrometer is underutilized during the time that is required for this chromatographic separation to occur.

In many cases, methods to improve sample throughput are considered important for effective utilization of expensive instruments, and to reduce the time that is required to deliver information.

Two prior art approaches are considered. First, Waters/Micromass has proposed directing two independent streams of ions to one orifice of a mass spectrometer using a mechanical baffle in a system called LockSpray™. In this approach, two electrospray ionization (ESI) needles are brought to the vicinity of the ion orifice leading into the vacuum chamber. In order that the two sample streams not be mixed together as solutions, and delivered through one stream to one ESI needle, this system includes two ESI sources conveying separate sample streams to their respective needles. In order to keep the electrospray sources operational and to simplify data acquisition, the device includes a mechanical baffle driven by a motor. The mechanical device serves to allow only one, but not both sprays at a same time, to deliver ions towards the orifice leading into the mass spectrometer. Simultaneously, the alternate sprayer continues to operate, but the baffle prevents cross talk between the two sprays. One application, in LockSpray™, is to deliver a reference compound through one of the two spray needles. The reference compound is delivered to the mass spectrometer for short periods of time on an intermittent basis, to serve to re-calibrate the mass scale of the mass spectrometer. This ensures accurate mass measurements.

Covey et al. in U.S. application Ser. No. 10/148,888, filed on Dec. 14, 2000, propose a system including two or more ESI needles and having an electrode in the vicinity of each needle. By variation of the voltage to the deflector electrode of the ESI needle, the ions may either be moved toward the orifice of the mass spectrometer, or collide with the deflector (or other conductive surface) and not be delivered to the mass spectrometer.

In a second method, a commercial device is available that uses a mechanical multiport valve to deliver various liquid sample streams into one liquid stream, which is then delivered to an electrospray needle. In this case, the selection of liquid streams is performed before the electrospray ionization process. It is clear that liquid streams take time to be purged from the capillary leading to the electrospray needle, therefore the rate of switching is limited by this clean-out period. Faster switching of the liquid flows results in "memory" and "carry-over" from one stream to another. The mass spectrometer data is then of limited quality. Also, it is clear that the sample streams must be compatible, and must also have similar solvent composition and ionic strength.

The requirement for a mechanical, motor-driven device is a limitation of the prior art approaches. In addition to the reliability problems that are inherent in such mechanical systems, the delivery of ions from one or more of the sources is compromised relative to what it would be if the single ionizer were used in conjunction with the mass spectrometer. In the LockSpray™ system, the sensitivity of the sample stream is about 80% of what it would be in a conventional system because the ESI source cannot be located in an optimal position relative to the orifice of the mass spectrometer. In general, compared to mechanical devices, an electronic solution is less costly and more reliable. Although electronic manipulation of the ESI-produced ions by deflector electrode systems overcomes this limitation of mechanical devices, the deflector electrode approach also induces loss of sensitivity of each ESI source relative to what it would be if the ESI sources were located at optimum positions in front of the orifice leading into the mass spectrometer. It is an additional limitation of a deflector electrode system that the sensitivity of each ESI needle may not be equivalent to the other ESI needles, as a result of small variations in the mechanical positions relative to the orifice and to the deflector electrodes. The need for careful mechanical, electronic and gas flow adjustment limits the practical application of the multiple deflector approach to multiplexing ions from several ESI sources. Accordingly, this approach does not permit simultaneous parallel operation of two or more different types of sources. For example, simultaneous delivery of one sample with ESI and a second using atmospheric pressure MALDI is not practical.

Multiplexing switching of liquid sample flows prior to delivery of a single liquid stream to an ESI source (for example) using a multiport valve is slow and puts severe constraints on the types of liquid flows that may be sampled simultaneously. Liquid sample switching is practical if repeat identical analyses are being performed in parallel with identical conditions of flow and solvent media. Sample streams containing immiscible solvents cannot be mixed using a multiport valve system. High Performance Liquid Chromatography (HPLC) separations using solvent gradients are impractical unless the parallel separations have the same gradient, and are started simultaneously. In a liquid-multiplexing system, all samples are ionized with one type of source (ESI, Atmospheric Pressure Chemical Ionization (APCI), photoionization, thermospray, particle beam as some non-limiting examples) without opportunity to ionize in parallel using other types of ionization sources including atmospheric pressure Matrix Assisted Laser Desorption Ionization (MALDI) for example.

SUMMARY OF THE INVENTION

It is an object of the instant invention to provide a system that overcomes some of the limitations of the prior art.

It is another object of the instant invention to provide a FAIMS system for multiplexing ions from a plurality of ionization sources through a single ion inlet aperture of a mass spectrometer.

In accordance with an aspect of the instant invention there is provided an apparatus for separating ions in the gas phase, comprising: a high field asymmetric waveform ion mobility spectrometer including an inner electrode having an outer surface and a length; and, an outer electrode having an inner surface and a length and surrounding the inner electrode over at least a portion of the length of the inner electrode, the inner electrode and the outer electrode defining an analyzer region therebetween and being disposed in a spaced apart arrangement for allowing ions to propagate therebetween, the outer electrode comprising an outlet from the analyzer region and at least a first ion inlet and a second distinct ion inlet into the analyzer region, the first ion inlet and the second distinct ion inlet each for communicating with at least one ionization source, the inner electrode and the outer electrode for providing an electric field within the analyzer region resulting from application of an asymmetric waveform voltage to at least one of the inner electrode and the outer electrode and from application of a compensation voltage to at least one of the inner electrode and outer electrode, the electric field for selectively transmitting ions within the analyzer region between at least one of the first ion inlet and the second distinct ion inlet and the outlet.

In accordance with another aspect of the instant invention there is provided method for separating ions originating from different ion sources, the method comprising the steps of: providing a high field asymmetric waveform ion mobility spectrometer having at least a first ion inlet and a second distinct ion inlet into an analyzer region thereof, the at least a first ion inlet and a second distinct ion inlet being separately in fluid communication with a first ionization source and a second ionization source, respectively; directing ions from at least one of the first ionization source and the second ionization source toward the first ion inlet and the second distinct ion inlet, respectively; receiving ions including ions of interest into the analyzer region via at least one of the first ion inlet and the second ion inlet; and, transmitting the ions of interest through the analyzer region between the at least one of the first ion inlet and the second distinct ion inlet and an outlet of the analyzer region.

In accordance with another aspect of the instant invention, there is provided a method of multiplexing ions from a first ionization source and from a second ionization source, comprising: during a first period of time, providing in a substantially continuous manner first ions from a first ionization source into an analyzer region of a FAIMS device via a first ion inlet of the FAIMS device; during a second period of time at least partially overlapping with the first period of time, providing in a substantially continuous manner second ions from a second ionization source into the analyzer region of the FAIMS device via a second ion inlet of the FAIMS device; during a first overlapping portion of the first period of time and of the second period of time, providing first conditions within the analyzer region of the FAIMS device for transmitting at least some of the first ions to an ion outlet of the FAIMS device and for other than transmitting the second ions to the ion outlet of the FAIMS device; and, during a second overlapping portion of the first period of time and of the second period of time, providing second conditions within the analyzer region of the FAIMS device for transmitting at least some of the second ions to the ion outlet of the FAIMS device and for other than transmitting the first ions to the ion outlet of the FAIMS device.

In accordance with another aspect of the instant invention, there is provided a method of multiplexing ions from a first ionization source and from a second ionization source, comprising: during a first period of time, providing in a substantially continuous manner first ions along a first ion flow route between a first ionization source and a first ion inlet of a first FAIMS device; during a second period of time overlapping with the first period of time, providing in a substantially continuous manner second ions along a second ion flow route between a second ionization source and a second ion inlet of the first FAIMS device; during a first overlapping portion of the first period of time and of the second period of time: providing first conditions within the first FAIMS device for transmitting at least some of the first ions between the first ion inlet and an ion outlet of the first FAIMS device; and, affecting trajectories of the second ions so as to interrupt a flow of the second ions along the second ion flow route; and, during a second overlapping portion of the first period of time and of the second period of time: providing second conditions within the first FAIMS device for transmitting at least some of the second ions between the second ion inlet and the ion outlet of the first FAIMS device; and, affecting trajectories of the first ions so as to interrupt a flow of the first ions along the first ion flow route.

In accordance with another aspect of the instant invention, there is provided a apparatus for multiplexing ions from a first ionization source and from a second ionization source, comprising: a monolithic outer-electrode member including a first passageway defined therethrough and open at opposite ends thereof, a second passageway defined therethrough and open at opposite ends thereof, and a third passageway defined therethrough and open at opposite ends thereof, the second passageway defined adjacent to the first passageway and intersecting with the first passageway so as to form a first orifice therebetween, and the third passageway defined adjacent to the first passageway and intersecting with the first passageway so as to form a second orifice therebetween; a first inner electrode for being positioned within the first passageway so as to define a first annular space between an outer surface of the first inner electrode and an inner surface of the first passageway; a second inner electrode for being positioned within the second passageway so as to define a second annular space between an outer surface of the second inner electrode and an inner surface of the second passageway; and, a third inner electrode for being positioned within the third passageway so as to define a third annular space between an outer surface of the third inner electrode and an inner surface of the third passageway; wherein, during use, ions introduced into the second annular space propagate through the first orifice and into the first annular space, and ions introduced into the third annular space propagate through the second orifice and into the first annular space.

An apparatus for multiplexing ions from a plurality of ionization sources, comprising: a first FAIMS analyzer including an inner electrode and an outer electrode defining an annular space therebetween, the outer electrode having a plurality of spaced-apart ion inlet orifices and a single ion outlet orifice; a plurality of other FAIMS analyzers disposed adjacent to the first FAIMS analyzer, each FAIMS analyzer of the plurality of other FAIMS analyzers having a single ion outlet orifice in communication with one ion inlet orifice of the plurality of ion inlet orifices of the first FAIMS analyzer, and each FAIMS analyzer having a single ion inlet orifice for supporting introduction of ions thereto; and, an electrical controller in communication with the first FAIMS analyzer, for providing conditions within the first FAIMS analyzer for supporting transmission therethrough of at least some of the ions introduced into the first FAIMS analyzer from at least one FAIMS analyzer of the plurality of other FAIMS analyzers.

U.S. Provisional Patent Application No. 60/354,711, filed Feb. 08, 2002, is incorporated by reference herein.

U.S. Provisional Patent Application No. 60/505,868 filed Sep. 26, 2003, is incorporated by reference herein.

BRIEF DESCRIPTION OF THE DRAWINGS

Exemplary embodiments of the invention will now be described in conjunction with the following drawings, in which similar reference numerals designate similar items:

FIG. 1b is a side elevational view of the cylindrical side-to-side FAIMS device shown in FIG. 1a;

FIG. 7d shows a cross sectional end view of the FAIMS device of FIG. 7a;

FIG. 9a shows a time-profile of the $V_{tF1}$ voltage applied to the inner electrode of one of the trapping FAIMS devices of the multiple FAIMS device of FIG. 8a;

FIG. 9b shows a time-profile of the $V_{tF2}$ voltage applied to the inner electrode the other one of the trapping FAIMS devices of the multiple FAIMS device of FIG. 8a;

FIG. 9c shows a time-profile for the CV applied to the inner electrode of the other FAIMS device of the multiple FAIMS device of FIG. 8a;

FIG. 10a shows a simplified cross sectional view of another multiple FAIMS device, including two trapping FAIMS devices that are aligned one each with ion inlets into another FAIMS device, each trapping FAIMS device including a modified outer electrode and an electrically isolated disk electrode;

FIG. 10b shows an enlarged partial view of the multiple FAIMS device of FIG. 10a about a region proximate the disk electrode;

DESCRIPTION OF THE PREFERRED EMBODIMENTS

The following description is presented to enable a person skilled in the art to make and use the invention, and is provided in the context of particular applications thereof. Various modifications of the disclosed embodiments will be apparent to those of skill in the art, and the general principles defined herein are readily applied to other embodiments and applications without departing from the spirit and scope of the invention. Thus, the present invention is not intended to be limited to the embodiments disclosed, but is to be accorded the widest scope consistent with the principles and features disclosed herein.

The underlying principle that the disclosed embodiments have in common is the presence of a plurality of ion inlets provided through a FAIMS electrode into an analyzer region of a FAIMS device, the ion inlets for communicating with one or more ionization source. The term ionization source is intended to include any device that produces ions of a temporary nature in a dynamic fashion. Some non-limiting examples of ionization sources that are envisaged for use with the instant invention include: an electrospray ionization source, a corona discharge ionization source, a radioactive foil ionization source, a photoionization source, a laser source, etc. In the detailed description and in the claims that follow, an ion inlet is considered to be communicating with an ionization source when there is a reasonable probability that an ion of interest, which is flowing along an ion flow route from the ionization source to the ion inlet, will pass through the ion inlet and enter into the analyzer region. Optionally, a portion of the ion flow route is through an analyzer region of another FAIMS device, which other FAIMS device is disposed intermediate the ionization source and the ion inlet. Accordingly, communicating is not intended to include remote communication with an ionization source, in which there is a statistically low probability of ions propagating from the ionization source, through the ion inlet, and into the analyzer region. The reader will appreciate the instant invention, when viewed in the context of prior art.

Figure 1A:
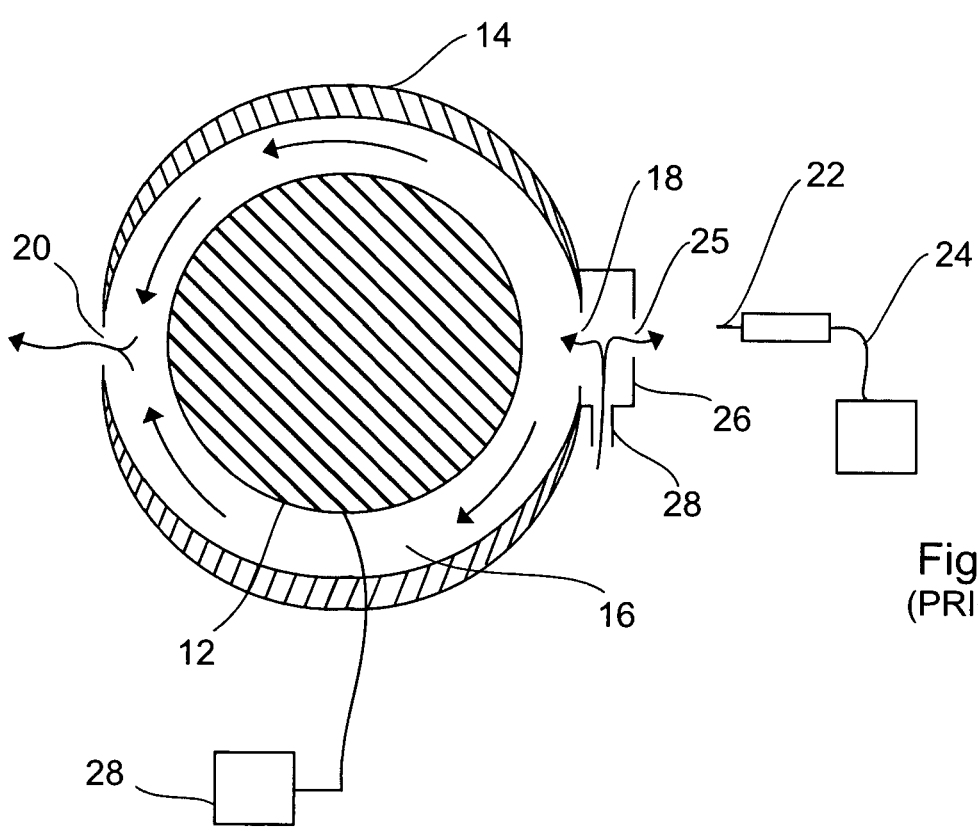
FIG. 1a is a simplified cross sectional end view of a cylindrical side-to-side FAIMS device according to the prior art.

Referring to FIG. 1a, shown is a simplified cross sectional end view of a cylindrical side-to-side FAIMS according to the prior art. The cylindrical side-to-side FAIMS device, shown generally at 10, includes inner and outer cylindrical electrodes 12 and 14, respectively, which are supported by an electrically insulating material (not shown) in an overlapping, spaced-apart arrangement. The generally annular space between the inner electrode 12 and the outer electrode 14 defines a FAIMS analyzer region 16. The analyzer region 16 is of approximately uniform width and extends around the circumference of the inner electrode 12. An ion inlet 18 is provided through the outer electrode 14 for introducing ions from an ion source into the analyzer region 16. For example, the ion source is in the form of an electrospray ionization ion source including a liquid delivery capillary 24, a fine-tipped electrospray needle 22 that is held at high voltage (power supply not shown) and a curtain plate 26 serving as a counter-electrode for the electrospray needle 22. Of course, any other suitable ionization source is optionally used in place of the electrospray ionization ion source. A flow of a carrier gas, which is represented in the figure by a series of closed-headed arrows, is provided within the analyzer region 16 to carry the ions around the inner electrode 12 and toward an ion outlet 20. An orifice 25 within the curtain plate electrode 26 allows for a portion of the carrier gas introduced at gas inlet 28 to flow in a direction that is counter-current to the direction in which the ions are traveling near the ion inlet 18, so as to desolvate the ions before they are introduced into the analyzer region 16. The inner electrode 12 is in electrical communication with a power supply 28 that during use is capable of applying a high voltage asymmetric waveform (DV) and a low voltage dc compensation voltage (CV) to the inner FAIMS electrode 12.

Still referring to FIG. 1a, ions are produced in the gas phase at the fine-tipped electrospray needle 22 from a suitable sample containing a species of interest. Typically, a mixture including a plurality of different ion types is produced when the sample is ionized. The potential gradient pushes the ions of the mixture away from the electrospray needle 22, toward the curtain plate electrode 26. A portion of the ions pass through the orifice 25 in the curtain plate electrode 26, become entrained in the carrier gas flow and are carried into the FAIMS analyzer region 16. Once inside the FAIMS analyzer region 16, the ions are carried through an electric field that is formed within the FAIMS analyzer region 16 by the application of the DV and the CV to the inner FAIMS electrode 12. Ion separation occurs within the FAIMS analyzer region 16 on the basis of the high field mobility properties of the ions. Those ions of the mixture that have a stable trajectory for a particular combination of DV and CV are selectively transmitted through the FAIMS analyzer region 16, whilst other ions of the mixture collide with an electrode surface and are lost. The selectively transmitted ions are extracted from the analyzer region 16 via ion outlet 20 and are typically subjected to one of detection and further analysis.

Figure 1B:
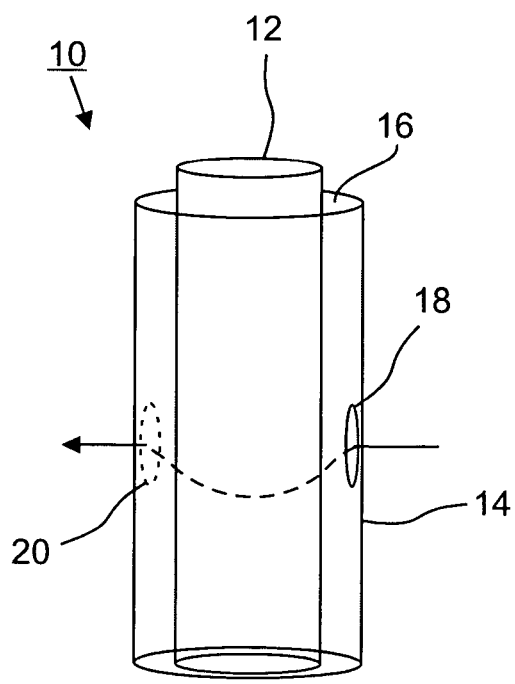

Referring now to FIG. 1b, shown is a simplified side elevational view of the cylindrical side-to-side FAIMS of FIG. 1a. Elements labeled with the same numerals have the same function as those illustrated in FIG. 1a. The dotted line extending between ion inlet 18 and ion outlet 20 represents one possible average ion flow path around the inner electrode 12. An average ion flow path is defined as the net trajectory of an ion as a result of a carrier gas flow through the analyzer region, although the individual ion also experiences an oscillatory motion between the electrodes as a result of the applied asymmetric waveform voltage. In particular, the dotted line represents one of two shortest average ion flow paths through the analyzer region 16, one shortest average ion flow path extending in each direction around the inner electrode 12. Of course, when many like-charged ions are present within the analyzer region, ion-ion repulsion forces tend to cause the ions to spread out slightly along the length of the inner electrode 12. Accordingly, some selectively transmitted ions migrate into portions of the analyzer region where the gas flow rate is low or stagnant, making their extraction from the analyzer region difficult.

Figure 2A:
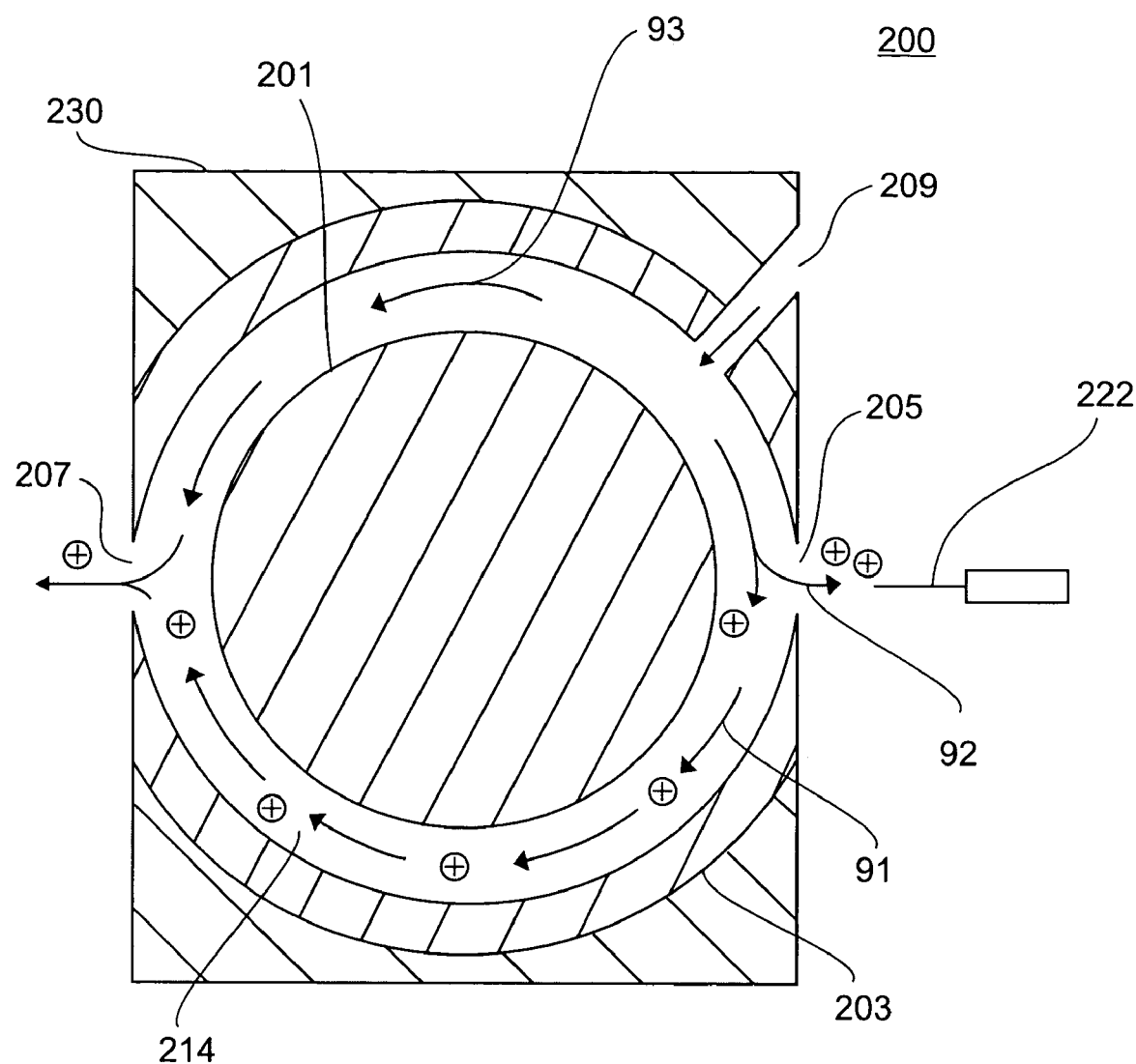
FIG. 2a shows a simplified cross sectional end view of a FAIMS device without a separate desolvation chamber and having a gas inlet positioned in close proximity to an ion inlet.

Referring now to FIG. 2a, shown is a simplified cross sectional end view of FAIMS device without a separate desolvation chamber and having a gas inlet positioned in close proximity to an ion inlet. A FAIMS device 200 includes an inner electrode 201, and outer electrode 203, an ion inlet 205 as well as an ion outlet 207. The inner and outer electrodes are for example provided as a solid cylinder and a cylindrical pipe, respectively. In general, the inner electrode has a length and an outer circumference, whereas the outer electrode has a length and an inner circumference. The ion inlet and ion outlet are for example provided in the form of one of an orifice and a slit. The components of the FAIMS device are embedded in an insulating material 230 such as polyetheretherketone (PEEK), which is used for maintaining the relative position of the electrodes one to the other. Typically, the FAIMS device 200 is in fluid communication with another device, for instance one of a pump and a not illustrated mass spectrometer detector, so that a gas flow is pulled through the FAIMS device 200 and out of the outlet 207.

Referring still to FIG. 2a, the FAIMS device 200 comprises a second inlet, that is a port for a gas inlet 209 through the wall of outer electrode 203 in the vicinity of the ion inlet 205. Arrows illustrate the gas flows in this first embodiment of the instant invention, the lengths of which are indicative of the difference in the velocity of gas flow rates around the inner electrode 201. A fine-tipped electrospray needle 222 that is held at high voltage (power supply not shown), is one component of the ionization source shown at FIG. 2a. Of course, any other suitable ionization source is used optionally in place of the electrospray ionization source. The gas introduced via the gas inlet 209 into the FAIMS device splits into two flows. One of the flows, the extra gas flow 93 travels around one side of the inner electrode toward the ion outlet 207. The other gas flow, comprising both the desolvation gas flow 92 and the carrier gas flow 91, travels in a direction around the other side of the inner electrode toward the ion inlet 205. In a region near the ion inlet 205 the other gas flow further splits into two flows, the desolvation gas flow 92 and the carrier gas flow 91. The desolvation gas flow 92 functions to desolvate the electrosprayed ions as they travel through the ion inlet 205 toward the analyzer region 214. This desolvation process reduces the amount of solvent and other contaminants that enter the FAIMS analyzer region and eliminates the need for a curtain plate assembly.

Ions are able to pass through the counter-current flow of desolvation gas 92 and into the FAIMS analyzer region 214 because of the electric field produced by the high voltage that is applied to the ionization source. The high voltage applied to the electrospray needle 222, in addition to producing an intensely strong electric field that creates conditions necessary to ionize the components of a liquid sample, also results in a strong electric field that directs electrosprayed ions of the appropriate charge polarity away from the electrospray needle 222 and toward the outer electrode 203 that serves as the counter electrode for the electrospray needle 222. Some of the ions pass through the ion inlet 205 of the FAIMS device. The carrier gas flow 91 transports ions around the inner electrode 201 and toward the ion outlet 207. Those ions which are selectively transmitted through the analyzer region 214, for the particular combination of DV and CV that is applied to the FAIMS electrodes, are extracted from the analyzer region 214 via the ion outlet 207.

In the FAIMS device 200 shown at FIG. 2a, ions passing through the ion inlet 205 and entering the analyzer region 214 travel around only one side of the inner electrode 201. The gas flow entering the FAIMS device through the gas inlet 209 and flowing in a direction toward the ion inlet 205 substantially prevents a flow of ions from traveling in a direction from the ion inlet 205 toward the gas inlet 209. In addition, the total volume of gas flow through the ion outlet 207 is equal to the sum of carrier gas flow 91 and extra gas flow 93. The distance between the gas inlet 209, and the ion outlet 207 is shorter in one direction (counter clockwise in the example of FIG. 2a) than in the other (clockwise in the example of FIG. 2a). That is the distance that the extra gas flow 93 travels from the gas inlet 209 to the ion outlet 207 is shorter than the distance that the carrier gas flow 91 travels from the gas inlet 209 to the ion outlet 207. Thus, a velocity of the extra gas flow 93 is higher than a velocity of the carrier gas flow 91. A low carrier gas flow rate translates into a longer transmission time of ions through the analyzer region 214. This in turn leads to an increase in ion loss due to processes such as diffusion and space charge repulsion, both of which are time dependent and therefore, possibly lower ion transmission through the FAIMS device 200.

Figure 2B:
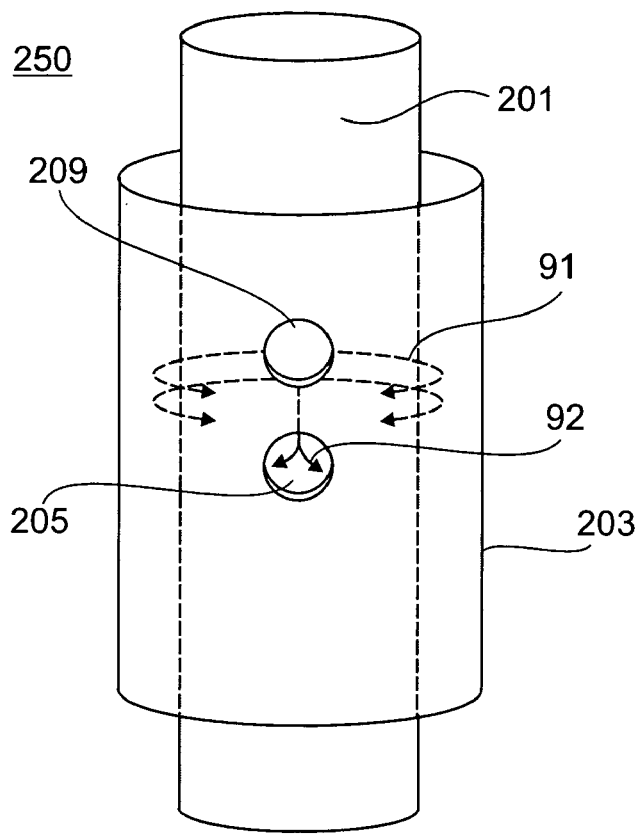
FIG. 2b shows a side elevational view of a side-to-side FAIMS device without separate desolvation region having a gas inlet and an ion inlet both positioned opposite to an ion outlet.
Figure 2C:
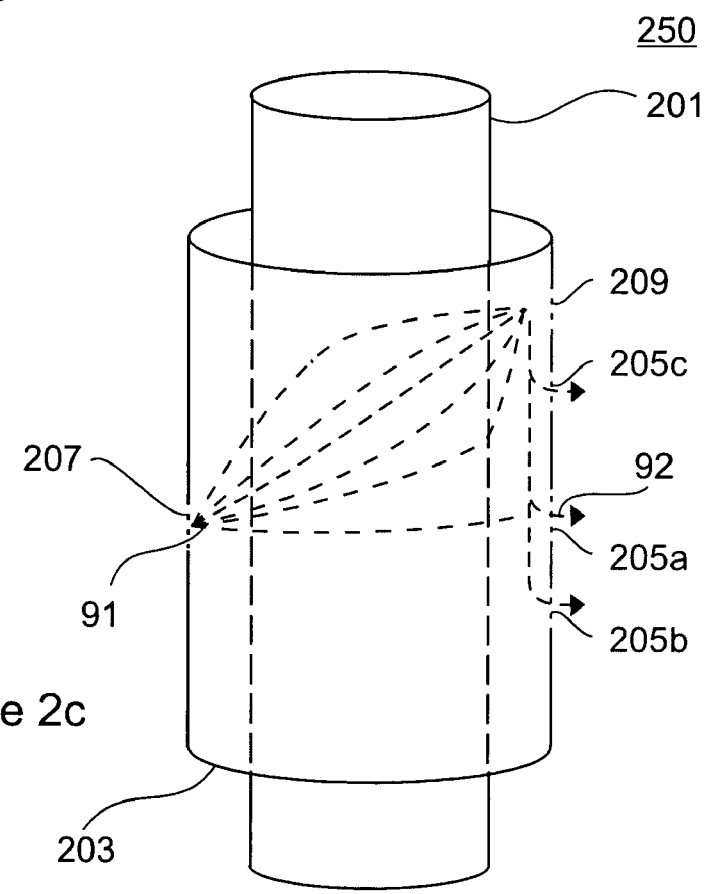
FIG. 2c shows a side elevational view of a side-to-side FAIMS device indicating different positions of an ion inlet relative to a gas inlet and an ion outlet.

Referring now to FIG. 2b, shown is a side elevational view of a side-to-side FAIMS device without separate desolvation region and having a gas inlet and an ion inlet both positioned opposite to an ion outlet. In the FAIMS device shown generally at 250, the gas inlet 209 and the ion inlet 205 are positioned at 180° from the ion outlet (not shown). The ion inlet 205 and the gas inlet 209 are adjacent to each other, but rather than being adjacent along a circumference of a cylindrical outer electrode 203 as in FIG. 2a, the ion inlet 205 and the gas inlet 209 are adjacent to each other along a longitudinal length of the outer electrode 203. This positioning of the inlets supports a carrier gas flow 91 around both sides of an inner electrode 201, with an approximately same carrier gas flow rate in both directions around the inner electrode 201 in a direction toward the not illustrated ion outlet. In FIG. 2c, shown are three possible locations 205a, 205b, and 205c for an ion inlet 205. Since the gas inlet 209 is not placed at the same location along the length of the outer electrode 205 as the ion outlet 207, gas exiting the FAIMS device 250 at the ion outlet 207 will travel around the inner electrode 201 as is shown schematically in FIG. 2c. The preferred gas flow path depends on variables such as gas flow rates exiting the analyzer region via the ion inlet and the ion outlet. When the ion inlet 205 is not positioned between the ion outlet 207 and the gas inlet 209 with reference to the main axis, for example at ion inlet position 205b, ions that have entered the FAIMS device 250 experience only a counter-flow of gas which prevents the ions from traveling around the inner electrode to the ion outlet. When the ion inlet 205 is placed between the ion outlet 207 and the gas inlet 209 with reference to the main axis, i.e. at ion inlet position 205c, ions that enter the FAIMS device become entrained in the carrier gas flow and are transported by the carrier gas around the inner electrode 201 and through the ion outlet 207. Optionally, the gas inlet 209 and the ion inlet 205 are of different size and or shape.

Of course, the figures that are referred to throughout the detailed description are greatly simplified so as to facilitate an understanding of the instant invention. A reader skilled in the art will appreciate that the gas enters and exits the space between the inner and outer electrodes mostly through the ion and gas inlets and outlets.

Figure 3:
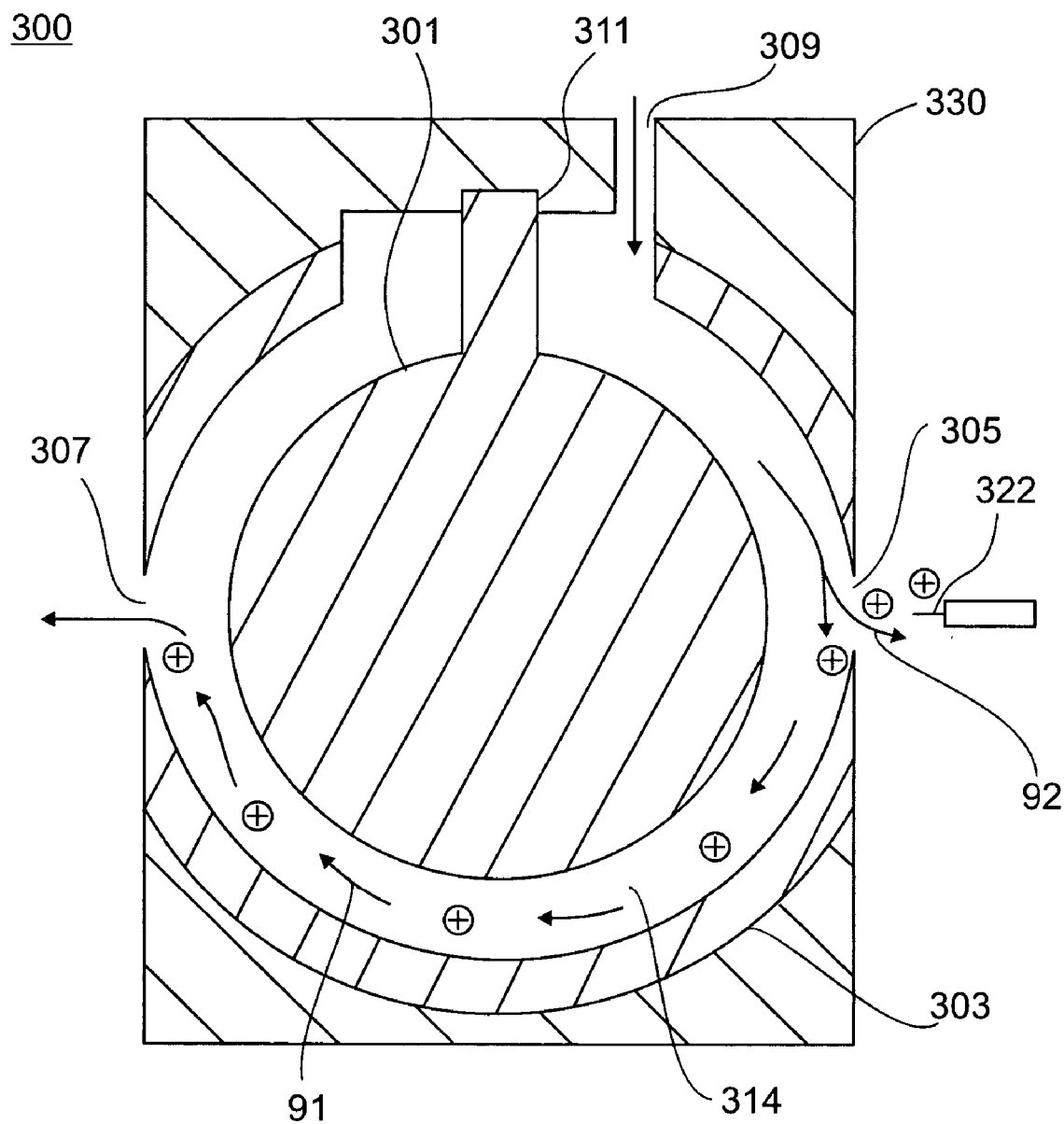
FIG. 3 shows a simplified cross sectional end view of a side-to-side FAIMS device having a protruding gas barrier.

Referring now to FIG. 3, shown is an end view of another FAIMS device without a separate desolvation chamber and having a gas inlet positioned in close proximity to an ion inlet. A FAIMS device 300 includes an inner electrode 301, and outer electrode 303 having an ion inlet 305 and an ion outlet 307. The inner electrode 301 and the outer electrode 303 are supported by an electrically insulating material 330 in an overlapping spaced-apart configuration. Each of the ion inlet and the ion outlet are for example provided in the form of one of an orifice and a slit. Typically, the FAIMS device 300 is coupled to another device, for instance one of a pump and a not illustrated mass spectrometer detector, so that a gas flow is pulled through the FAIMS device 300 and out of the ion outlet 307.

In addition, the FAIMS device 300 comprises a second inlet, that is a port for a gas inlet 309 through the wall of the outer electrode 303 in the vicinity of the ion inlet 305. Further, part of the outer electrode 303 has been cut away to enable a protruding part 311 of the inner electrode 301 to extend into the insulating material 330. Enough of the outer electrode 303 is cut away to leave a wide enough physical space between the electrodes so as to prevent electrical discharge between the inner electrode 301 and the outer electrode 303. The shape of the protruding part 311 is optionally varied. Further optionally, the inner electrode is provided as cylindrical electrode, and the protruding part is provided by a protruding segment of the electrically insulating material 330.

The protruding part 311 of the inner electrode 301 forms an approximately gas tight seal with the electrically insulating material 330 to form a physical barrier which forces the gas flow, which is represented in the figure by a series of closed headed arrows, around one side of the inner electrode 301. Gas entering the FAIMS device 300 through the gas inlet 309 is forced to flow in one direction, the direction toward the ion inlet 305. Unlike the FAIMS device 200 described with reference to FIG. 2a, no extra gas flow is produced in the instant embodiment. Accordingly, the total gas flow exiting at the ion outlet 307 is equal to the carrier gas flow 91. Near the ion inlet 305, the gas flow splits with a portion of the gas going out toward the electrospray needle 322 and constituting the desolvation gas flow 92. The other portion, the carrier gas flow 91, continues through the FAIMS analyzer region 314, around the inner electrode 301, and transports entrained ions to the ion outlet 307.

Optionally the protruding part provides a small gas channel that results in a small controlled extra gas flow traveling towards the ion outlet around the portion of the inner electrode that is not in communication with the ion inlet.

The blockage of flow by the modification of the inner and outer electrodes 301 and 303, respectively, results in changes in the electric fields near the modified region, causing suboptimal conditions for transmission of ions. Therefore, the blockage is advantageously located in a region away from the ion path through the FAIMS device 300 so that the changes in the electric fields caused by the protruding part 311 induce a minimal effect upon the electric fields that ions experience during their transit from the ion inlet 305 to the ion outlet 307.

The presence of the protruding part 311 not only increases carrier gas flow velocities by maintaining a single gas flow stream between the FAIMS electrodes, but also increases an intensity of an ion stream exiting the FAIMS device at the outlet 307. Advantageously, FAIMS device 300, although more elaborate and intricate in its construction than the FAIMS device 200 shown at FIG. 2a, supports analysis of an ion beam having initially a low ion concentration.

Figure 4:
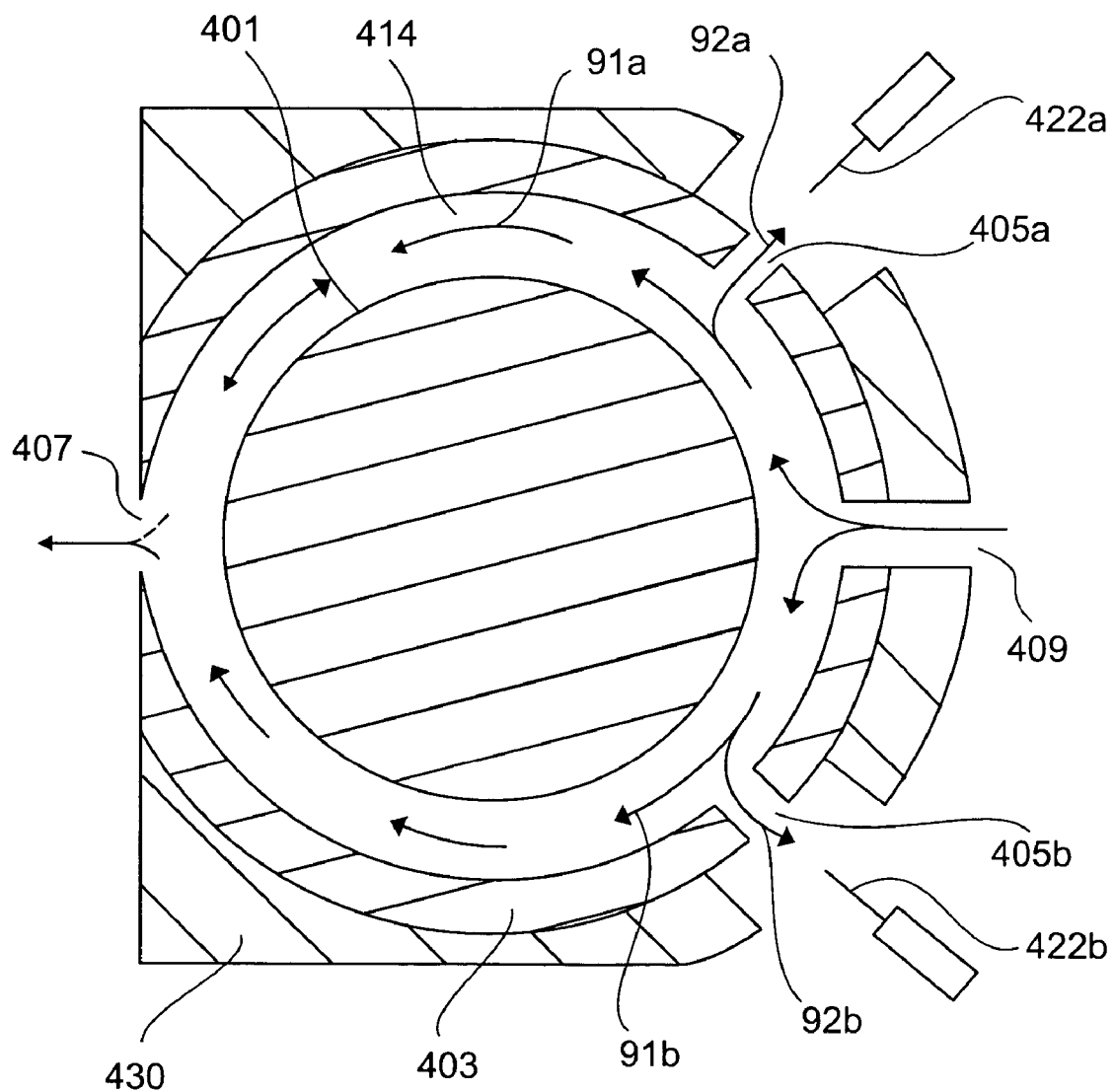
FIG. 4 shows a simplified cross sectional end view of a side-to-side FAIMS device without a separate desolvation chamber and having a gas inlet positioned in close vicinity to two ion inlets.

The concepts for the design of a FAIMS device with a plurality of inlets as outlined above are now applied to FAIMS devices having a plurality of ion inlets. Referring now to FIG. 4, shown is an end view of a first embodiment of the instant invention. A FAIMS device 400 comprises a plurality of ion inlets, each ion inlet of the plurality of ion inlets for being disposed adjacent to a different ion source. More particularly, the FAIMS device 400 includes an inner electrode 401, an outer electrode 403, two ion inlets 405a and 405b, as well as an ion outlet 407. The inner and outer electrodes are for example provided as a solid cylinder and a cylindrical pipe, respectively. In general, the inner electrode 401 has a length and an outer circumference, whereas the outer electrode 403 has a length and an inner circumference. The inner electrode 401 and the outer electrode 403 are supported by an electrically insulating material 430 in an overlapping spaced-apart configuration. Each of the ion inlet and the ion outlet are for example provided in the form of one of an orifice and a slit. Typically, the FAIMS device 400 is coupled to another device, such as for instance one of a pump and a not illustrated mass spectrometer detector, so that a gas flow is pulled through the FAIMS device 400 and out of the ion outlet 407.

In addition, the FAIMS device 400 comprises a third inlet, namely a port for a gas inlet 409. The gas inlet 409 is positioned such that a flow of gas is introduced at 180° from the ion outlet 407. Gas flows are substantially equal around the two sides of the inner electrode 401. The gas inlet 409, the two ion inlets 405a and 405b, and the ion outlet 407 are all located on the circumference of the outer electrode 403 at one location along the length of the outer electrode 403. The fine-tipped electrospray needles 422a and 422b that are held at high voltage (power supply not shown), each comprise one component of the separate ion sources shown at FIG. 4. The fine-tipped electrospray needles 422a and 422b are positioned in close vicinity to the inlets 405a and 405b, respectively. The ion inlets 405a and 405b are positioned in a way that the gas inlet 409 is located at an approximately intermediate position between the two ion inlets.

Ions produced by an electrospray ionization source are directed toward the corresponding ion inlet by a strong electric field that exists between the electrospray needle tip and the outer electrode. A gas flow entering the gas inlet 409 splits approximately equally into two flows, since the distances to the ion outlet 407 along the two directions around the inner electrode 401 are approximately equal. When the total volume of the gas flow entering the gas inlet 409 exceeds the volume of gas flow out of the ion outlet 407, then a first portion of the excess flow exits outwardly through ion inlet 405a to provide a desolvation gas flow 92a, and a second portion of the excess flow exits outwardly through ion inlet 405b to provide a desolvation gas flow 92b. Provided that the areas of the two ion inlets 405a and 405b are approximately equal, then the volumes of the desolvation gas flow 92a and the desolvation gas flow 92b are approximately equal. The ions that are entering the FAIMS analyzer 414 through ion inlet 405a and 405b therefore pass through a counter-current flow of gas, and are desolvated. Ions that have successfully entered the analyzer region 414 are carried by the carrier gas flows 91a and 91b around the circumference of the inner electrode 401.

The following non-limiting example illustrates a balanced gas flow mode of operation of FAIMS device 400. It is assumed in the instant example that the FAIMS device 400 is coupled to another device causing a flow of gas through the analyzer region 414 and out of the ion outlet 407. If the gas flow out of the outlet 407 is 400 mL/minute, and a flow of approximately 600 mL/minute is pushed into the gas inlet 409, then it is expected that a desolvation gas flow 92a of approximately 100 mL/minute flows out of ion inlet 405a and a desolvation gas flow 92b of approximately 100 mL/minute flows out of ion inlet 405b. In addition, a carrier gas flow 91a of approximately 200 mL/minute flows in the direction from ion inlet 405a towards the ion outlet 407, and a carrier gas flow 91b of approximately equal volume flows between ion inlet 405b and the ion outlet 407. The two flows of 200 mL/minute combine near the ion outlet 407, and a gas flow of 400 mL/minute exits through the ion outlet 407. The flow rates used in this example are illustrative of the operation of the FAIMS device 400. Optimum gas flow rates are possibly determined by experimentation.

The presence of two ion inlets allows for a more efficient use of the FAIMS device 400. When only one ion inlet is used, for example ion inlet 405b, and the other ion inlet 405a is blocked, probe preparation for feeding the electrospray needle 422a can take place, while electrospray needle 422b is producing ions. Once an experiment involving electrospray needle 422b is finished, the functionality of the ion inlets is switched, that is ion inlet 405b is blocked and ion inlet 405a is opened, such that the ions produced at electrospray needle 422a are analyzed. In this way, a continuous utilization of the FAIMS device is achieved, independent of delays relating to probe preparation, sample changes, and the like.

Figure 5A:
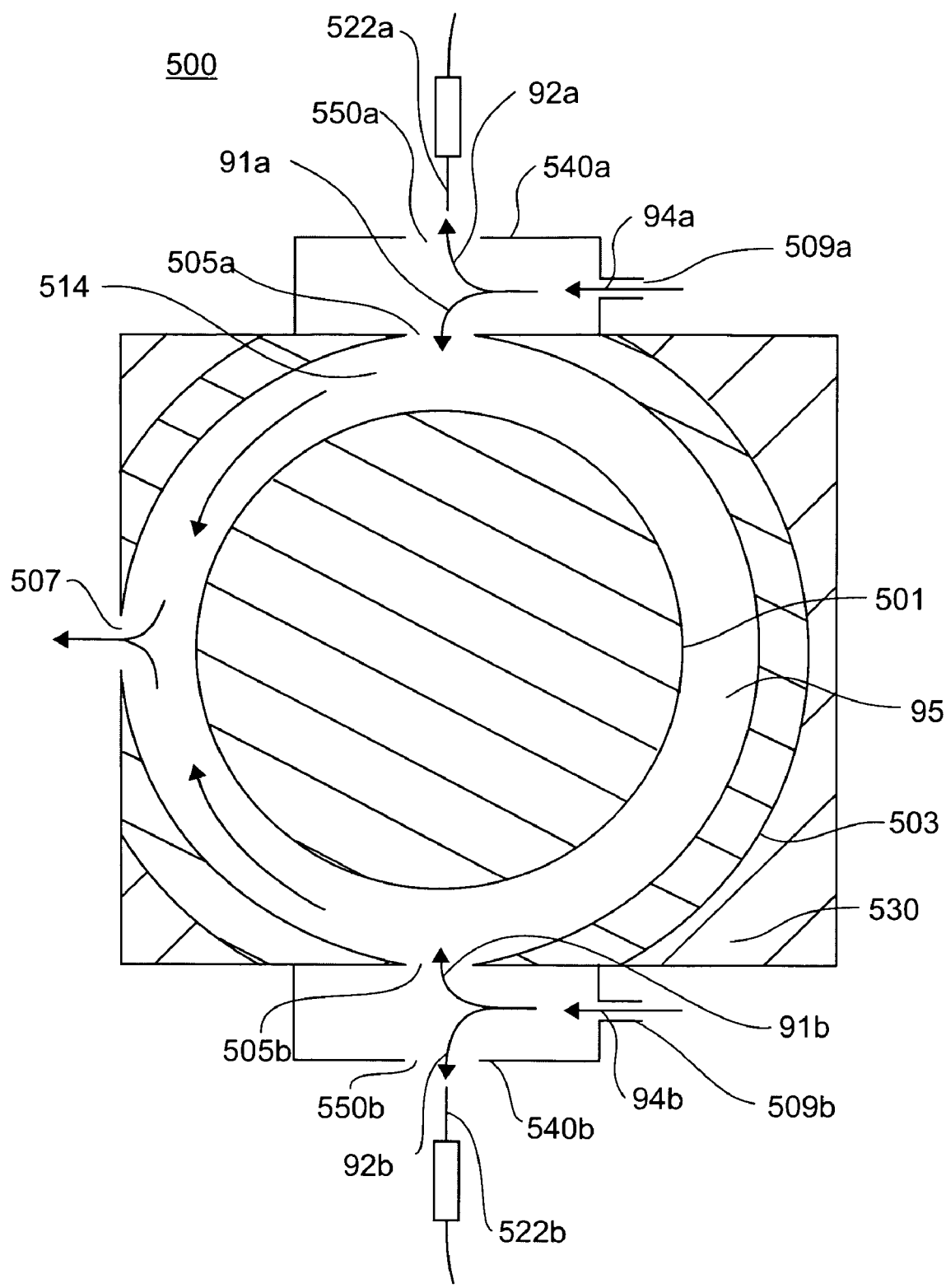
FIG. 5a shows a simplified cross sectional end view of a side-to-side FAIMS device having two ion inlets and two ion sources.

Referring now to FIG. 5a shown is an end view of a second embodiment of the instant invention. FAIMS device 500 comprises a plurality of ion inlets, each ion inlet of the plurality of ion inlets for being disposed adjacent to a different ion source. Some advantages indicated in connection with FAIMS device 400, such as the effective use of multiple ion inlets, are also fully realized in FAIMS device 500. More particularly, the FAIMS device 500 includes an inner electrode 501, an outer electrode 503, two ion inlets 505a and 505b, as well as an ion outlet 507. Preferably, the two ion inlets are positioned approximately at an angle of 180° relative to each other. The ion outlet 507 is preferably positioned in an intermediate position between the two ion inlets 505a and 505b. The inner and outer electrodes are for example provided as a solid cylinder and a cylindrical pipe, respectively. In general, the inner electrode 501 has a length and an outer circumference, whereas the outer electrode 503 has a length and an inner circumference. The inner electrode 501 and the outer electrode 503 are supported by an electrically insulating material 530 in an overlapping spaced-apart configuration. Each of the ion inlet and the ion outlet are for example provided in the form of one of an orifice and a slit. Typically, the FAIMS device 500 is coupled to another device, such as for instance one of a pump and a not illustrated mass spectrometer detector, so that a gas flow is pulled through the FAIMS device 500 and out of the outlet 507.

In front of ion inlets 505a and 505b are positioned curtain plate assemblies including curtain plates 540a and 540b, respectively. The curtain plate assemblies include gas inlets 509a and 509b for the introduction of curtain gas flows 94a and 94b, respectively, and for the introduction of ion streams produced by fine-tipped electrospray needles 522a and 522b through curtain plate orifices 550a and 550b, respectively. The curtain plates 540a and 540b serve as counter-electrodes for the fine-tipped electrospray needles 522a and 522b, respectively. Curtain gas flows 94a and 94b introduced into the curtain plate assemblies split into carrier gas flows 91a and 91b flowing through ion inlets 505a and 505b into an analyzer region 514 of FAIMS device 500, and into desolvation gas flows 92a and 92b flowing towards electrospray needles 522a and 522b, respectively, and desolvating ions produced by said electrospray needles. The region between the two ion inlets 505a and 505b that is substantially opposite to the ion outlet 507 comprises a region of stagnant gas 95. In a balanced gas flow mode of operation, very little gas flow takes place in the area occupied by stagnant gas.

If the flow rates of each one of the curtain gas flows 94a and 94b are approximately equal, and assuming that the two ion inlets are of approximately equal area, then gas flows through each ion inlet will also be approximately equal. These operating conditions are appropriate for simultaneous analysis of ions that are produced separately at the two ionization sources. If the rate of curtain gas flow 94a is higher than the rate of curtain gas flow 94b, then the carrier gas flow 91a entering through the ion inlet 505a into the analyzer region 514 will split into a gas flow exiting through the ion outlet 507 and into a gas flow being swept around the analyzer region and exiting through ion inlet 505b, thereby reducing a volume of the carrier gas flow 91b that enters the analyzer region. Consequently, when the rate of curtain gas flow 94a is significantly higher than the rate of curtain gas flow 94b, the FAIMS device 500 acts to analyze ions produced by electrospray needle 522a. On the other hand, when the rate of curtain gas flow 94a is less than the rate of curtain gas flow 94b, the FAIMS device 500 acts to analyze ions produced by electrospray needle 522b. Thus, an appropriate adjustment of the flow rates of the curtain gas flows supports a selective switching between different ion sources, or different combinations of ion sources, of a plurality of ion sources. Of course, the ions from both electrospray sources must have appropriate ion mobility properties for being transmitted through the analyzer region 514 with a same applied CV and DV. Optionally, the applied CV and DV are rapidly switched during a period of time approximately coinciding with the switching between one source and the other, so as to provide appropriate conditions for selectively transmitting an ion of interest produced at the selected source. Further optionally, one of the ionization sources is other than an electrospray source, such as for instance corona discharge, radioactive foil, photoionization source, laser source, to name just a few non-limiting examples.

Figure 5B:
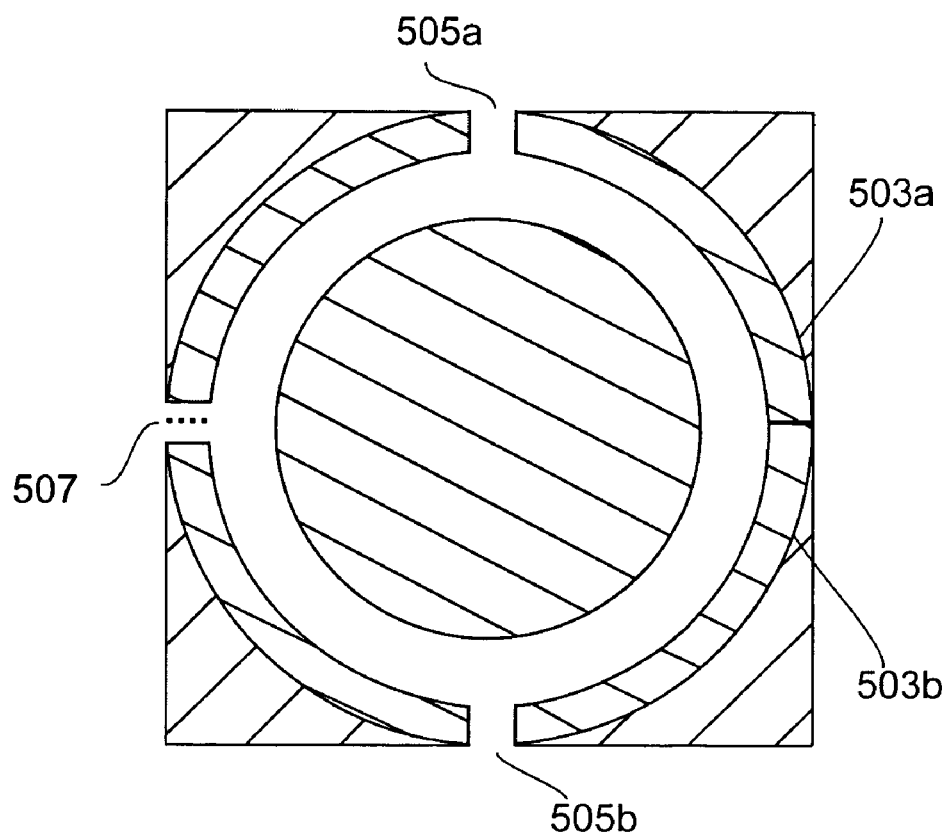
FIG. 5b shows a simplified cross sectional end view of side-to-side FAIMS device having a segmented outer electrode.

Referring to FIG. 5b, shown is a FAIMS device 550, in which the outer electrode is divided into two separate electrically isolated semi-electrodes 503a and 503b. Accordingly, different operating conditions may be imposed, for example by applying different voltages to the different semi-electrodes 503a and 503b, upon the ions traveling from the ion inlets 505a and 505b, respectively, to the ion outlet 507.

Figure 5C:
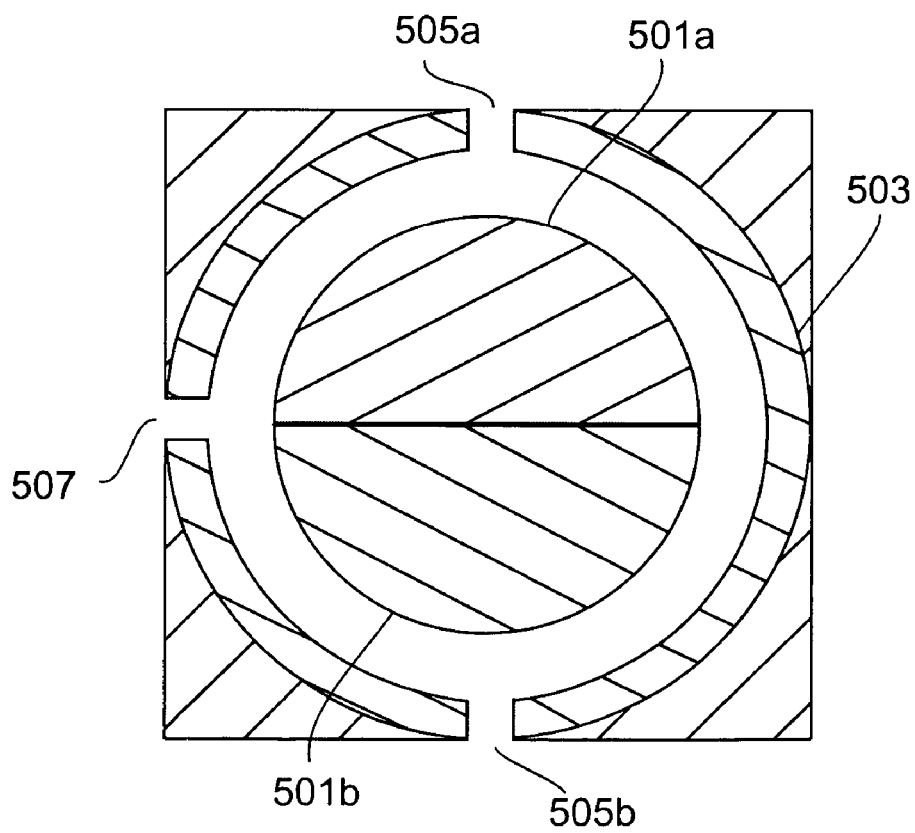
FIG. 5c shows a simplified cross sectional end view of side-to-side FAIMS device having a segmented inner electrode.

Referring now to FIG. 5c, shown is a FAIMS device 580, in which the inner electrode is divided into two separate electrically isolated semi-electrodes 501a and 501b. As was described with reference to FIG. 5b, different operating conditions may be imposed, for example by applying different voltages to the different semi-electrodes 501a and 501b, upon the ions traveling from the ion inlets 505a and 505b, respectively, to the ion outlet 507 Similar considerations apply to FAIMS device 400, shown at FIG. 4.

Figure 6A:
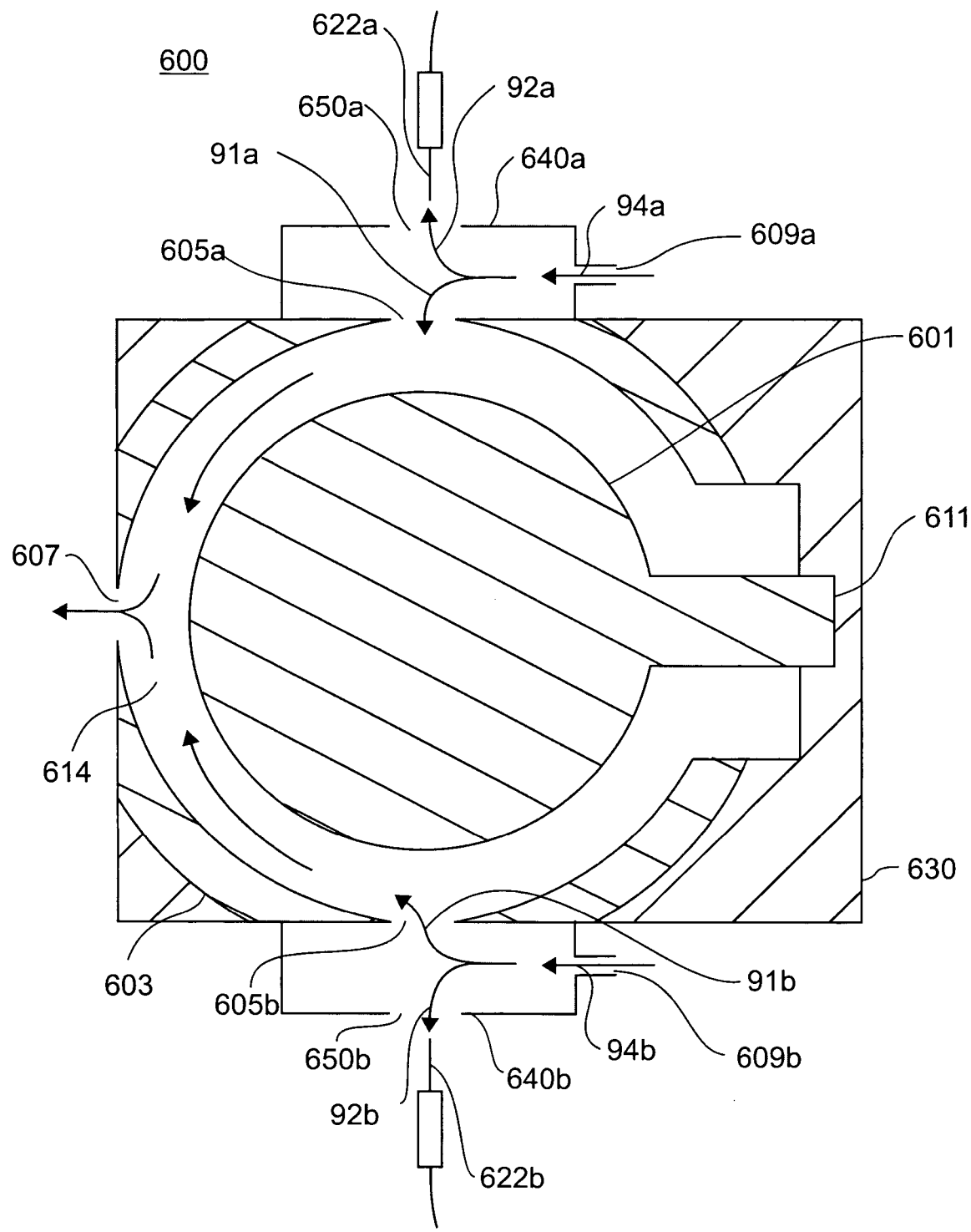
FIG. 6a shows a simplified cross sectional end view of a side-to-side FAIMS device having two ion inlets and two ion sources, and having a protruding gas barrier.

Referring now to FIG. 6a shown is an end view of another FAIMS device according to the instant invention. FAIMS device 600 comprises multiple inlets for ions and/or gases. More particularly, the FAIMS device 600 includes an inner electrode 601, an outer electrode 603, two ion inlets 605a and 605b, as well as an ion outlet 607. Preferably, the two ion inlets are positioned approximately at an angle of 180° relative to each other. The ion outlet 607 is preferably positioned in an intermediate position between the two ion inlets 605a and 605b. The inner and outer electrodes are for example provided as a solid cylinder and a cylindrical pipe. In general, the inner electrode 601 has a length and an outer circumference, whereas the outer electrode 603 has a length and an inner circumference. The inner electrode 601 and the outer electrode 603 are supported by an electrically insulating material 630 in an overlapping spaced-apart configuration. Each of the ion inlet and the ion outlet are for example provided in the form of one of an orifice and a slit. Typically, the FAIMS device 600 is coupled to another device, such as for instance one of a pump and a not illustrated mass spectrometer detector, so that a gas flow is pulled through the FAIMS device 600 and out of the outlet 607.

In front of ion inlets 605a and 605b are positioned curtain plate assemblies including curtain plates 640a and 640b, respectively. The curtain plate assemblies include gas inlets 609a and 609b for the introduction of curtain gas flows 94a and 94b, respectively, and curtain plate orifices 650a and 650b for the introduction of ion streams produced by fine-tipped electrospray needles 622a and 622b, respectively. The curtain plates 640a and 640b serve as counter-electrodes for the fine-tipped electrospray needles 622a and 622b, respectively. Curtain gas flows 94a and 94b introduced into the curtain plate assemblies split into carrier gas flows 91a and 91b flowing through ion inlets 605a and 605b into an analyzer region 614 of FAIMS device 600, and into desolvation gas flows 92a and 92b flowing towards electrospray needles 622a and 622b through curtain plate orifices 650a and 650b, respectively, and desolvating ions produced by said electrospray needles.

Further, part of the outer electrode 603 has been cut away to enable a protruding part 611 of the inner electrode 601 to extend into the insulating material 630 at a position opposite the ion outlet 607. Enough of the outer electrode is cut away to leave a wide enough physical space between the electrodes so as to prevent electrical discharge between the inner and outer electrodes. Optionally, the inner electrode is provided as a cylindrical electrode, and the protruding part is provided as a protruding segment of the electrically insulating material.

Figure 6B:
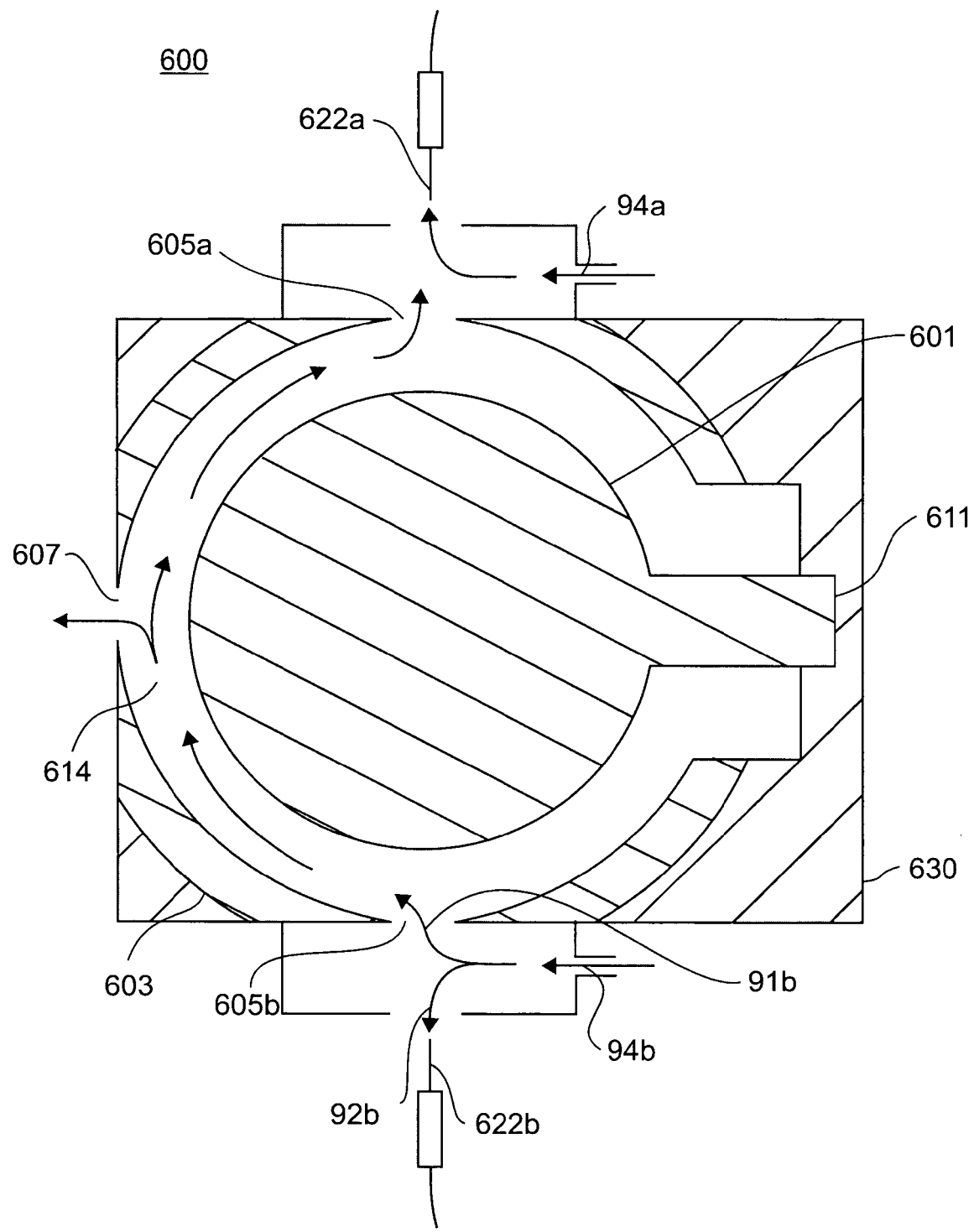
FIG. 6b shows the FAIMS device of FIG. 6a when operating in a different mode.

Referring now to FIG. 6b, it is shown that the FAIMS device 600 also supports a selective switching between different ion sources, in a manner similar to that of the FAIMS device 500. In the mode of operation that is illustrated at FIG. 6b, curtain gas flow 94b significantly exceeds curtain gas flow 94a. As a result, the direction of gas flow through the ion inlet 605a is reversed compared to that of the balanced flow mode of operation, which is illustrated at FIG. 6a. Hence, ions produced at electrospray needle 622b are carried into the analyzer region 614, whereas ions produced at electrospray needle 622a that are able to enter the analyzer region 614 immediately encounter a gas flow in a direction from the ion outlet 607 toward the ion inlet 605a, which prevents the ions from being transmitted through the analyzer region 614 toward the ion outlet 607.

Of course, the ions from both electrospray sources, which have appropriate ion mobility properties, are transmitted through the analyzer region 614 with a same applied CV and DV. Optionally, the applied CV and DV are rapidly switched during a period of time approximately coinciding with the switching between one source and the other, so as to provide appropriate conditions for selectively transmitting an ion of interest produced at the selected source. Further optionally, one of the ionization sources is other than an electrospray source, such as for instance corona discharge, radioactive foil, photoionization source, laser source, to name just a few non-limiting examples.

Optionally, at least one of the inner and outer electrodes is provided as two electrically isolated halves, such that different operating conditions may be provided for ions traveling from the ion source 622a to the ion outlet 607, and for ions traveling from the ion source 622b to the ion outlet 607. This optional embodiment supports a use of different gases within each half during a same period of operation, since significant mixing would only likely occur near the outlet.

In general, multiple ion inlets may support a mode of operation in which different gases are provided for transmitting ions through different portions of an analyzer region. In the above-mentioned examples, ions from a first ionization source are transmitted around a portion of a first side of the inner electrode by a first type of gas, whilst ions from a second ionization source are transmitted around a portion of a second side of the inner electrode by a second type of gas. Likely, a different combination of CV and DV is required to transmit ions produced at each ionization source, depending upon the mobility properties of the ions, the composition of the gas provided for transmitting the ions, the temperature of the gas, etc. Accordingly, the CV and DV that is applied between the inner electrode and the outer electrode is switched between at least two combinations, so as to analyze ions produced at the two ionization sources during different, non-overlapping periods of time. Optionally, segmented electrodes are provided so as to support the application of different combinations of CV and DV within different portions of the analyzer region during a same overlapping period of time.

Figure 7A:
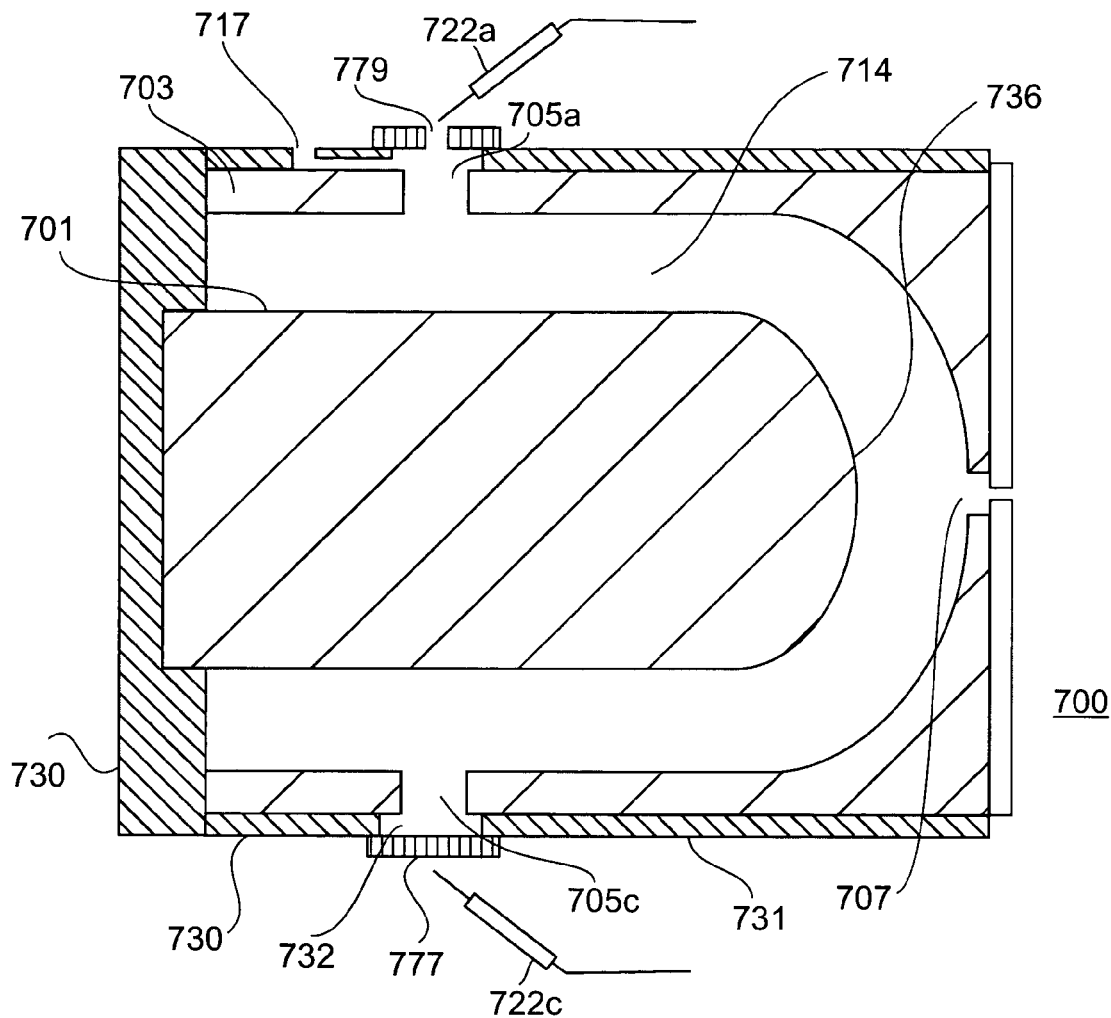
FIG. 7a shows a cross sectional side view of a FAIMS device including an ionization source selecting electrode.

The ideas that have been described supra in conjunction with the disclosed embodiments of the instant invention may also be applied to other type of FAIMS geometries, for example to a domed-FAIMS analyzer. Referring now to FIG. 7a, shown is cross sectional side view of a domed-FAIMS device 700 according to the instant invention. The domed FAIMS device 700 comprises an outer electrode 703, which generally has the shape of a cylindrical pipe open at one end and closed on the other end by means of a curved surface closure, in which there is disposed an ion outlet 707. Further, there are disposed four ion inlets 705a, 705c, 705b and 705d (the latter two not shown in FIG. 7a) in the outer electrode 703. In the preferred embodiment, the four ion inlets 705a, 705c, 705b and 705d are spaced at approximately 90° increments around the circumference of the outer electrode 703. Each ion inlet is separately in communication with one of four electrospray ionization sources 722a, 722c, 722b, and 722d (the latter two not shown in FIG. 7a). Furthermore, the domed-FAIMS device 700 includes a cylindrical inner electrode 701 having a curved surface terminus 736 proximate the ion outlet 707 of the outer electrode 703. The curved surface terminus 736 is substantially continuous with the cylindrical shape of the inner electrode and is aligned co-axially with the ion outlet 707. Two separate supporting sleeves 730 and 731, which are fabricated using an electrically insulating material, surround the outer electrode 703; each sleeve being fixed in place relative to the outer electrode. As shown in FIG. 7a, the two supporting sleeves 730 and 731 are mounted so as to leave a longitudinal gap 732 therebetween. The gap 732 is aligned with a region of the outer electrode 703 which includes the ion inlets 705a, 705c, 705b and 705d. Preferably, the gap 732 is of approximately uniform width around the circumference of the outer electrode 703.

An ion source selector comprising a conductive cover cylinder of thin metal, herein referred to as a "rotating ring" 777, covers the gap 732 between the supporting sleeves 730 and 731. The rotating ring 777 has an orifice shown as aperture 779, optionally located, by rotation of the rotating ring, adjacent to an ion inlet. The location of the aperture 779 in the rotating ring 777 is not restricted and therefore is placed for optimal sampling efficiency of ions into an ion inlet. The rotating ring 777 is made in a way that it fits snuggly across the gap 732 between the two supporting sleeves 730 and 731. The fit is not so snug, however, as to prevent a motor (not shown) from being able to rotate the ring 777. A curtain gas inlet 717 is provided through the supporting sleeve 730 for providing fluid communication with the gap 732.

Figure 7B:
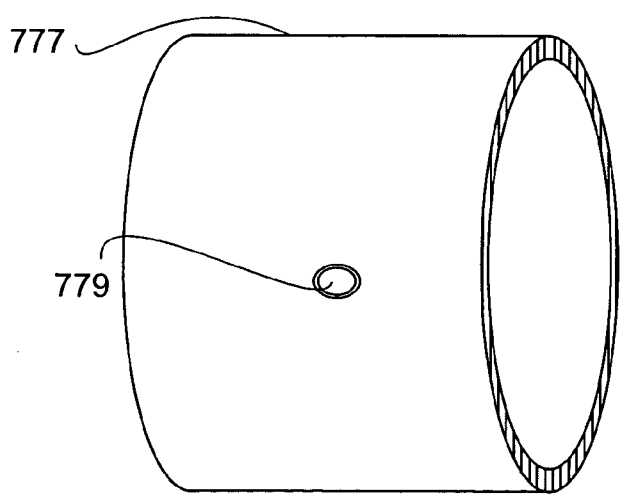
FIG. 7b shows a side view of the ionization source selecting electrode in the form of a rotating ring having an opening.
Figure 7C:
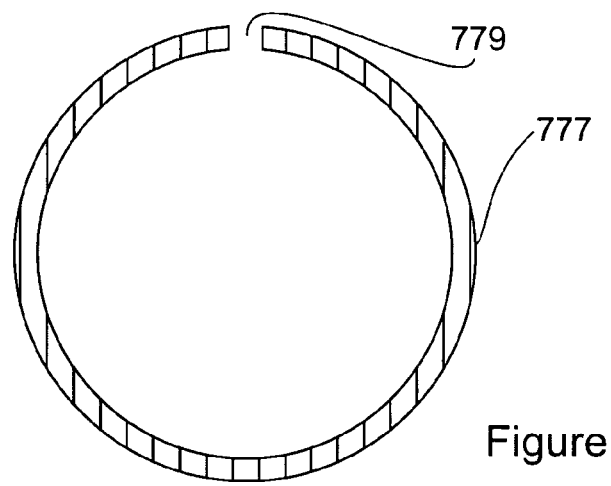
FIG. 7c shows an end view of the rotating ring having an opening.

Optionally, at least a portion of the rotating ring 777 engages a groove that is formed within one of the supporting sleeves 730 and 731, so as to prevent movement of the rotating ring 777 along the length of the outer electrode 703. Optionally, the rotating ring 777 is fabricated from an insulating material with a conductive surface. In FIG. 7b, a side view of the rotating ring 777 is shown, displaying the aperture 779, and in FIG. 7c, an end view of the rotating ring is shown.

Figure 7D:
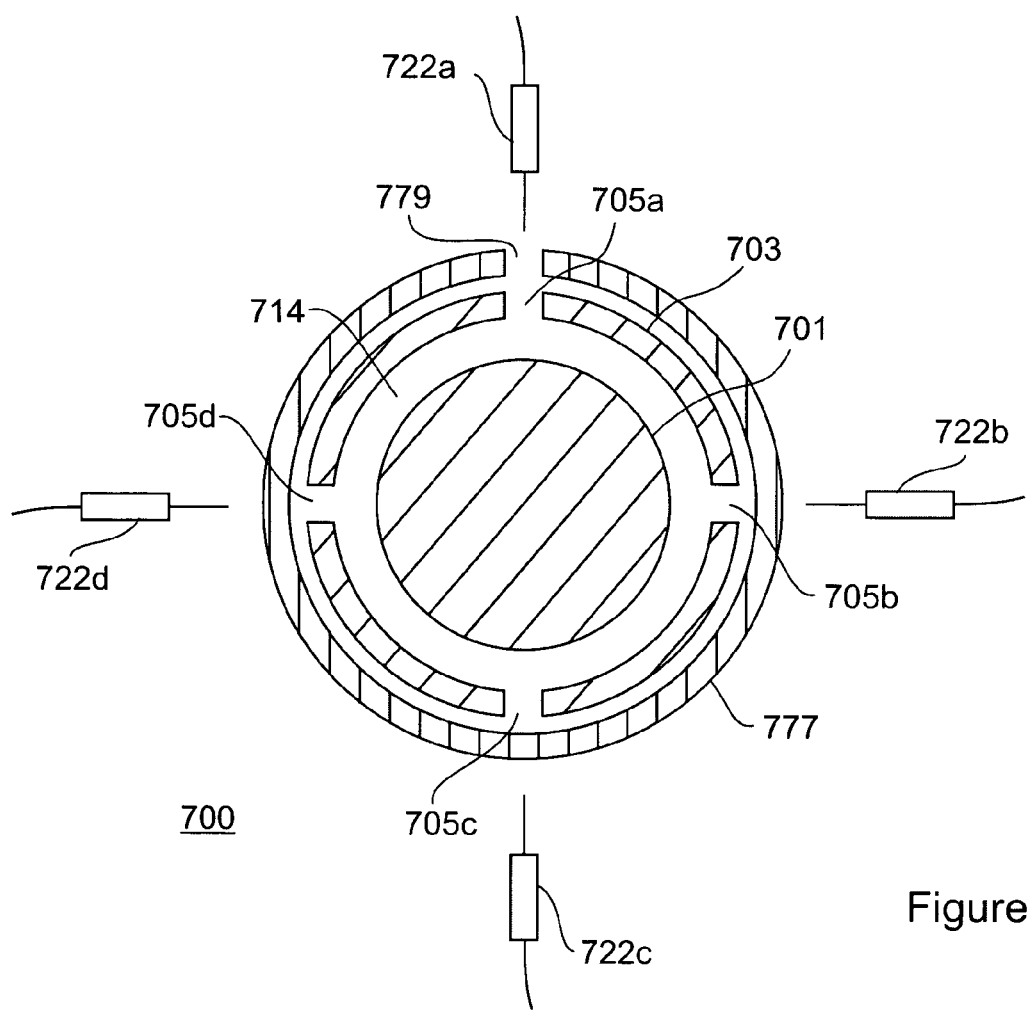

Referring now to FIG. 7d, a cross sectional view of FAIMS device 700 shows the inner electrode 701, the outer electrode 703, the rotating ring 777, the four ion inlets 705a, 705b, 705c, and 705d, as well as the four electrospray ionization sources 722a, 722b, 722c, and 722d. When in operation, all four electrospray ionization sources can spray continuously without interruption since the rotating ring provides a conductive counter electrode necessary for a stable spray. By having only one aperture 779, the rotating ring 777 selectively allows ions from one of the four electrospray ionization sources to pass into the FAIMS device. For example, still referring to FIG. 7d, the aperture 779 is aligned with ion inlet 705a and allows ions produced by electrospray ionization source 722a to enter the analyzer region 714.

Referring to FIGS. 7e, 7f, 7g, and 7h shown is the rotating ring 777 in positions to select ions from each of the various electrospray ionization sources 722a, 722b, 722c, and 722d, respectively. When the aperture 779 in the rotating ring 777 is adjacent to a particular electrospray ionization source, curtain gas that is pumped into the curtain gas inlet 717 as shown in FIG. 7a, exits in part through the aperture 779 in the rotating ring 777 to assist in desolvating ions being produced by the selected electrospray ionization source. Since the other electrospray needles are adjacent to a part of the rotating ring that does not have an aperture therethrough, no desolvation gas is available nor is any desolvation gas needed.

Referring again to FIG. 7a, the curtain gas introduced into curtain gas inlet 717, and thus into the gap 732 between supporting sleeves 730 and 731, is able to flow freely in a circumferential direction within the annular channel that is defined between the gap 732 and the rotating ring 777. This curtain gas flow splits so that a portion of the gas flows toward an electrospray ionization source 722a through the aperture 779 and the remaining portion of the gas flows through the four ion inlets 705a, 705b, 705c, and 705d into the analyzer region 714. Gas flowing through ion inlet 705a transports ions from the electrospray ionization source 722a into the FAIMS device and toward the ion outlet 707.

Still referring to FIG. 7a, optionally the other three ion inlets 705b, 705c, and 705d through the outer wall of the outer electrode 703 are plugged so as to prevent gas from entering the analyzer region therethrough. For example, the rotating ring 777 comprises plugs that are attached to the inner surface of the rotating ring 777, and located appropriately for covering three ion inlets in the outer electrode 703, when the aperture 779 is positioned adjacent to the fourth ion inlet. In operation, the plugs move together with the rotating ring 777. The plugs are preferably made from an electrically insulating material so as to isolate the conductive surface of the rotating ring 777 from the outer electrode.

Figure 7E:
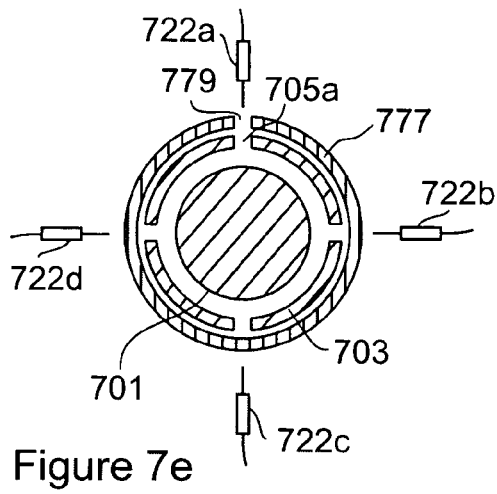
FIG. 7e shows a cross sectional end view of the FAIMS device of FIG. 7a with the opening in the rotating ring in alignment with a first ionization source.
Figure 7F:
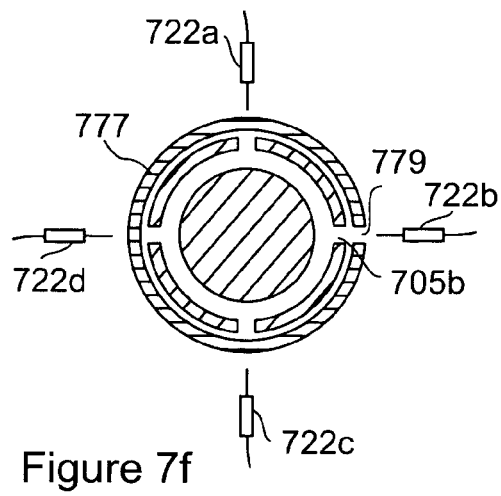
FIG. 7f shows a cross sectional end view of the FAIMS device of FIG. 7a with the opening in the rotating ring in alignment with a second ionization source.
Figure 7G:
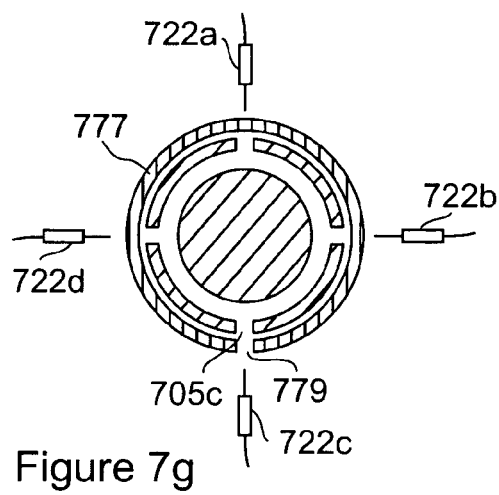
FIG. 7g shows a cross sectional end view of the FAIMS device of FIG. 7a with the opening in the rotating ring in alignment with a third ionization source.
Figure 7H:
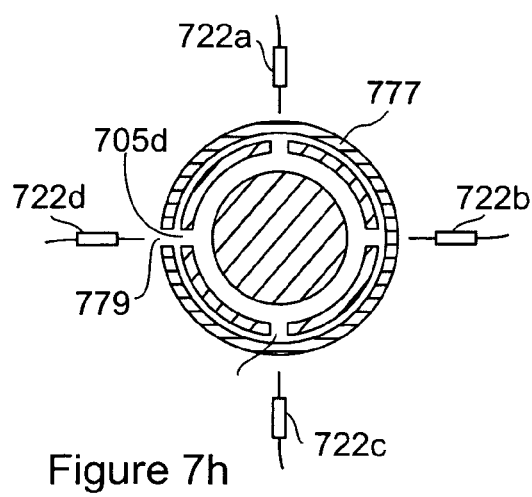
FIG. 7h shows a cross sectional end view of the FAIMS device of FIG. 7a with the opening in the rotating ring in alignment with a fourth ionization source.

To analyze samples from four ionization sources with the FAIMS device 700, the aperture 779 of the rotating ring 777 is rotated in increments of approximately 90° each, stopping for a predetermined period of time in front of each one of the four ionization sources. Referring again to FIGS. 7e, 7f, 7g, and 7h, one specific and non-limiting example is described for analyzing four samples. At time t=0 ms (milliseconds), ions from electrospray ionization source 722a are analyzed (FIG. 7e). After a period of time for analysis, for example 300 ms, the rotating ring 777 is rotated to align aperture 779 with ion inlet 705b, and ions from electrospray ionization source 722b are analyzed (FIG. 7f). There is a delay between the time the ring starts to rotate and the time when ions from electrospray ionization source 722b are extracted through ion outlet 707 (not shown). This delay time consists of the time required for the ring to rotate, the time required for the gas flow to equilibrate, and the time required for the ions to transmit through the FAIMS device. A typical delay time is approximately 200 ms. It follows that in the given example ions from electrospray ionization source 522b are analyzed starting at t=500 ms. After another 300 ms of analysis time and another 200 ms of delay time, ions from electrospray ionization source 522c are analyzed starting at t=1000 ms. Similarly, ions from electrospray ionization source 522d are analyzed starting at t=1500 ms. The process of sampling from each of the ionization sources starts over at t=2000 ms. In this example, data from a given electrospray source is collected each 2000 ms (2 sec). Although the present example uses four electrospray ionization sources, the process of analyzing ion beams stemming from a plurality of electrospray ionization sources works equally as well for an embodiments including more than, or less than four electrospray ionization sources. Furthermore, different ionization source technologies are optionally used at different ion inlets. Other suitable ionization source technologies include but are not limited to: corona discharge; radioactive foil; photoionization; and, laser ionization. Further still, a flow of a different gas, or mixtures of gases, is optionally provided at each inlet. A person of skill in the art will easily envision additional variations and applications for such a FAIMS device having multiple ion inlets.

Optionally, an outer electrode is provided having a single ion inlet, and at least a portion of the outer electrode including the single ion inlet is rotatable for selectively aligning the single ion inlet with one of a plurality of different ion sources disposed at intervals around the outer electrode. In the instant embodiment, the at least a portion of the outer electrode functions as an ion source selector.

Figure 8A:
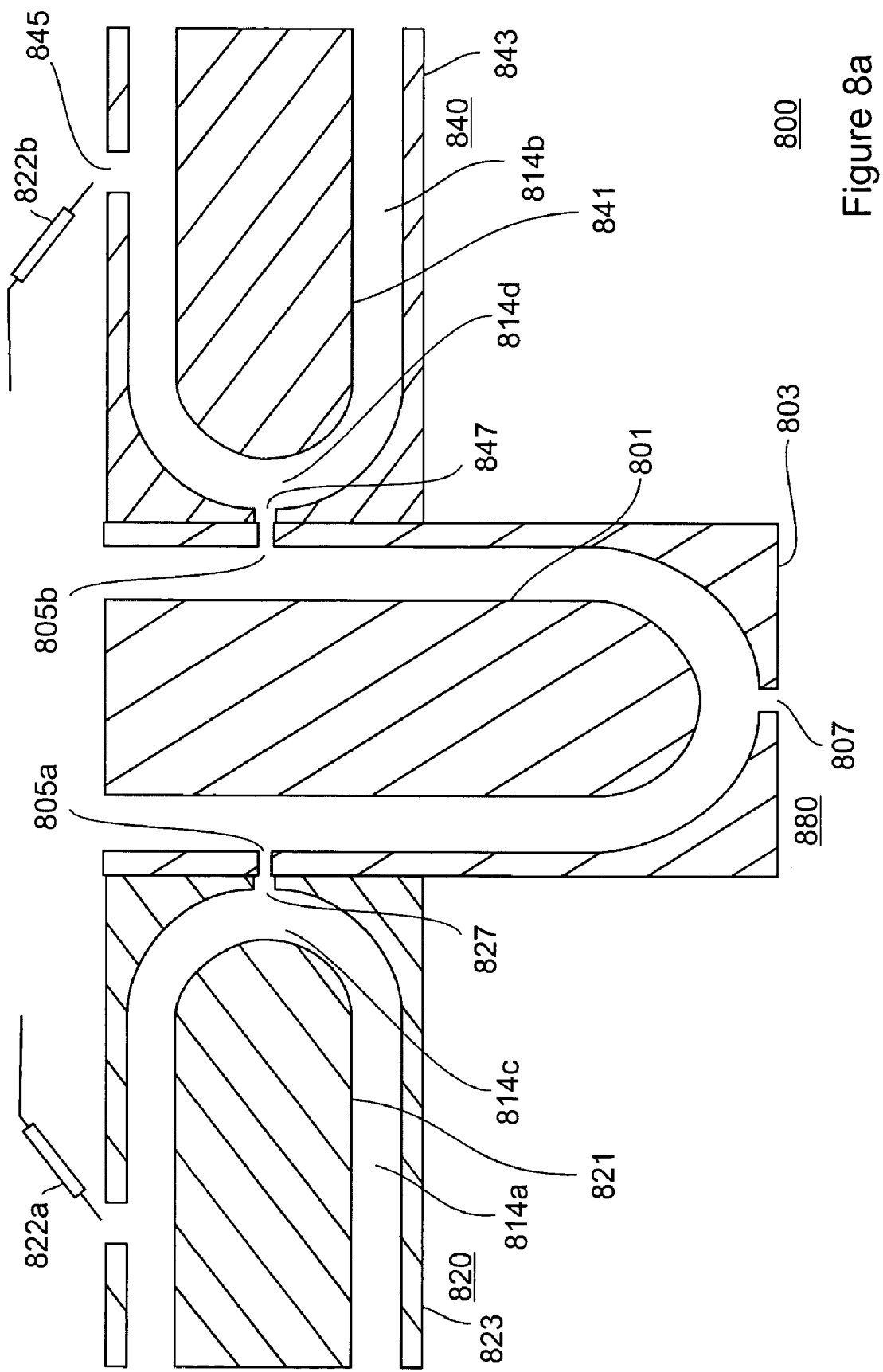
FIG. 8a shows a cross sectional side view of a multiple FAIMS device, including two trapping FAIMS devices that are aligned one each with ion inlets into another FAIMS device.

A FAIMS device including multiple ion inlets optionally supports multiple tandem FAIMS analysis of ions. For example, a first FAIMS device is optionally used as an ion trap, in which ions are stored and subsequently extracted into a second FAIMS device. Conditions for operating a trapping FAIMS device, or tFAIMS, are described. Referring now to FIG. 8a, shown is a cross-sectional view of a multiple FAIMS device according to the instant invention. A multiple FAIMS analyzer 800 comprises two domed tFAIMS 820 and 840, coupled to a third FAIMS 880. The domed tFAIMS 820 and 840 comprise inner electrodes 821 and 841, respectively. Ion outlets 827 and 847 of tFAIMS 820 and 840, respectively, are in communication with ion inlets 805a and 805b of FAIMS 880. An outlet 807 of FAIMS 880 is optionally coupled to a detector or an ion-analyzing device, such as a mass spectrometer. Two ionization sources 822a and 822b provide ions to the tFAIMS 820 and 840, respectively. The functionality of FAIMS 880 is similar to that of other FAIMS devices including multiple ion inlets, herein described previously.

A mode of selectively analyzing ions from the two ionization sources feeding the multiple FAIMS device 800 is described by way of the following non-limiting example. By changing conditions in each trapping tFAIMS device 820 and 840, the respective device is set either to accumulate trapped ions, or to extract trapped ions, the extracted ions being provided into FAIMS device 880. The ionization sources 822a and 822b are operated continuously so that ions produced by ionization source 822a continually enter tFAIMS 820 and ions produced by ionization source 822b continually enter tFAIMS 840. Initially, FAIMS operating parameters of gas flows and voltages are selected in tFAIMS 820 and tFAIMS 840 so that the ions of interest from ionization sources 822a and 822b are accumulated near the hemispherical tips of inner electrodes of tFAIMS 820 and tFAIMS 840, respectively. After a predetermined period of time, referred to as the accumulation time, ions are extracted from a trapping region 814c of tFAIMS 820 into FAIMS 880 by changing the conditions from trapping to extraction conditions. For example, the application of a pulsed DC offset voltage to the inner electrode 821 of tFAIMS 820 pushes ions that have been trapped in the vicinity of the tip of hemispherical inner electrode 821 of tFAIMS 820 towards the ion outlet 827. During the extraction of ions from tFAIMS 820, ions from electrospray ionization source 822b are still accumulating in the trapping region 814d of tFAIMS 840. Ions are extracted from tFAIMS 820 through ion outlet 827 into FAIMS 880 via ion inlet 805a, and are transported along the analyzer region of FAIMS 880. Conditions in FAIMS 880 are set so that ions of interest produced at ionization source 822a are selectively transmitted. The ions are transported toward the ion outlet 807, which is optionally coupled to one of a detector and an analyzing device. For example, ion outlet 807 is adjacent to an orifice leading to a vacuum chamber of a mass spectrometer (not shown). After ions have been extracted from tFAIMS 820, trapping conditions are restored for tFAIMS 820 and the process of accumulating ions, which are generated by electrospray ionization source 822a, in the trapping region of tFAIMS 820 starts again. At a predetermined time, ions from electrospray ionization source 822b are extracted from tFAIMS 840 in a similar manner as described above for tFAIMS 820, while ions from electrospray ionization source 822a are allowed to accumulate in the trapping region 814c of tFAIMS 820. During this extraction process, conditions in FAIMS 880 are such that ions of interest produced at ionization source 822b are selectively transmitted.

Still referring to FIG. 8a, the conductive outer electrodes 823, 843, and 803 of tFAIMS 820, tFAIMS 840, and FAIMS 880 are shown to be in direct mechanical and electrical contact. Optionally, a narrow insulator separates the three FAIMS devices; however, a gas-tight seal is maintained between the devices to efficiently transmit ions from each of the tFAIMS 820 and 840 into the analyzer region of FAIMS 880. Optionally, transfer between the tFAIMS 820 and 840, and FAIMS 880 is optimized by minimizing a mechanical depth of the ion outlets 827 and 847 to produce a very narrow sharp edged orifice between the devices.

Figure 8B:
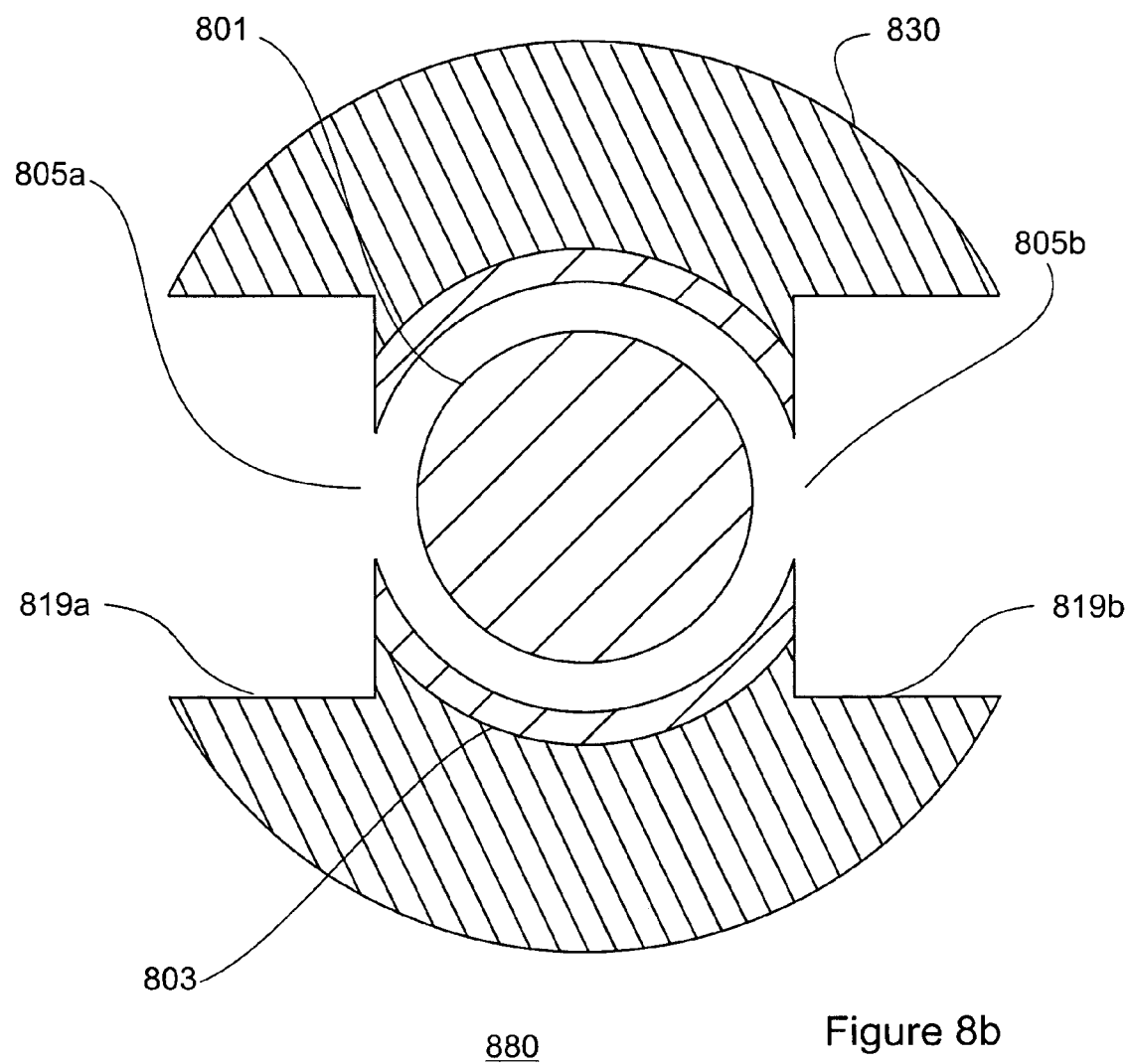
FIG. 8b shows a cross section of the multiple FAIMS device of FIG. 8a taken in isolation at a point where the trapping FAIMS devices align with the ion inlets of the other FAIMS device.

FIG. 8b shows a cross section of FAIMS 880 taken in isolation at a point where tFAIMS 820 and 840 align with ion inlets 805a and 805b of the FAIMS 880. A supporting sleeve 830 made of an electrically insulating material is modified so that the tFAIMS devices 820 and 840 can be fitted into the supporting sleeve. The wall of the outer electrode 803 near the ion inlets 805a and 805b is very thin. Two cylindrical cavity wells 819a and 819b are drilled into the supporting sleeve 830. The cylindrical cavity wells 819a and 819b are drilled sufficiently deeply that a cut is made into the material of the outer electrode 803, thereby forming a pair of sharp edged openings in the outer electrode 803 that serve as the ion inlets 805a and 805b.

Figure 8C:
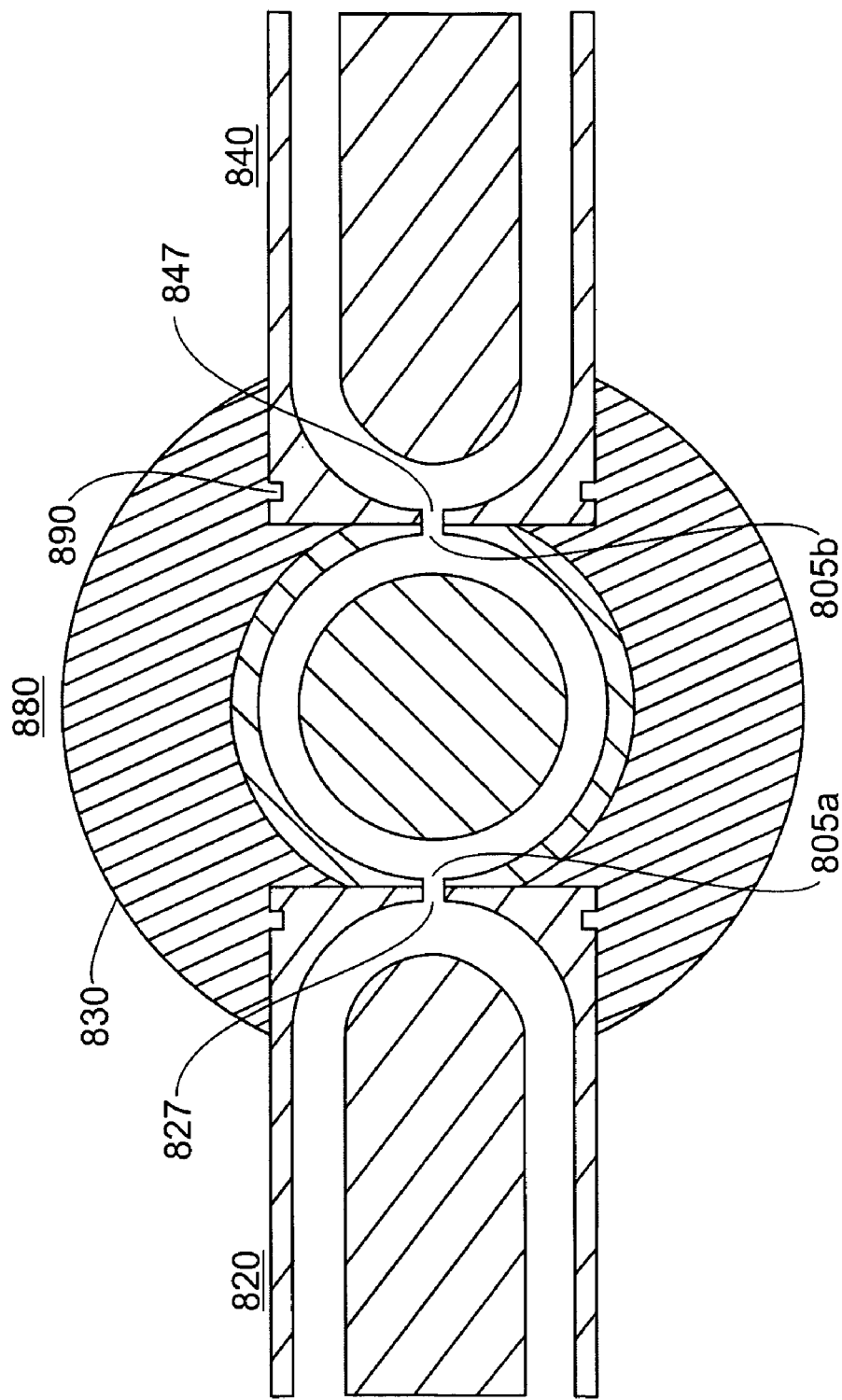
FIG. 8c shows is a simplified cross sectional view of the multiple FAIMS device of FIG. 8a, and illustrating the manner in which the two trapping FAIMS devices are mounted relative to the other FAIMS device.

Referring to FIG. 8c, shown is a simplified cross sectional view of multiple FAIMS device 800, illustrating how the tFAIMS 820 and tFAIMS 840 are inserted into the supporting sleeve 830. By placing a small O-ring in an O-ring groove on the outer surface of the outer electrode of each tFAIMS device, a gas tight connection between each tFAIMS and the FAIMS 880 is established while maintaining electrical isolation. If an inlet into FAIMS 880 is in the form of a slit, the O-ring groove is located in position 890. In this case, separate means (not shown) for insulating the FAIMS devices 820 and 840 from FAIMS 880 may be required.

Figure 9A:
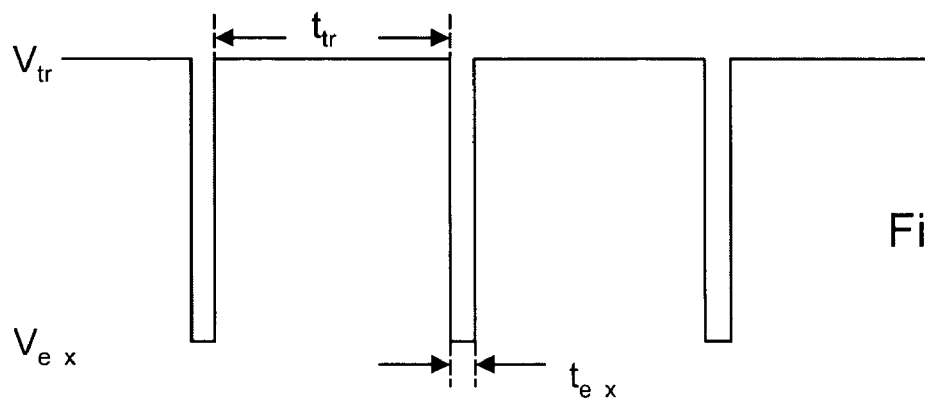
Figure 9B:
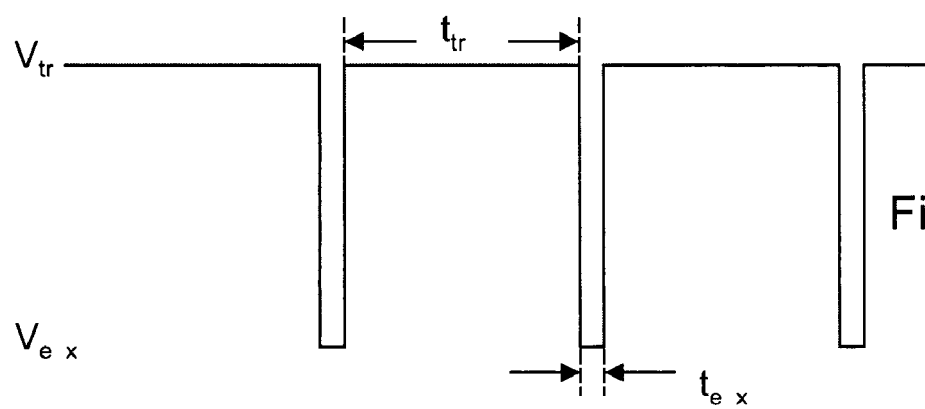
Figure 9C:
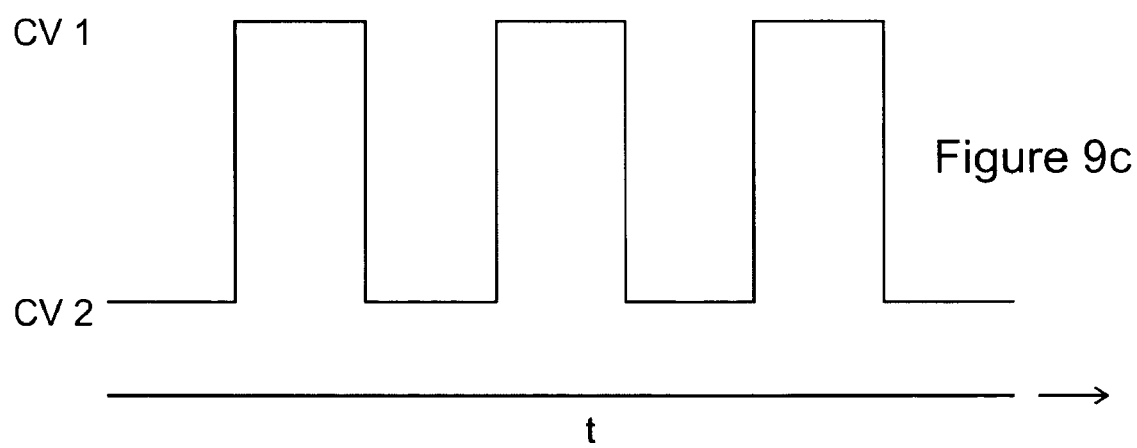

Referring now to FIGS. 9a through 9c, shown are time-potential profiles used in the operation of the multiple FAIMS device 800 for separately transmitting ions from each ion source. Relevant times are ion injection time $t_{tr}$, during which ions are trapped in a tFAIMS, and ion extraction time $t_{ex}$, during which ions are extracted from a tFAIMS. Referring to FIG. 9a, shown is a time-profile of the $V_{tF1}$ voltage applied to the inner electrode 821 of tFAIMS 820. A short period in time $t_{ex}$, during which an extraction voltage $V_{ex}$ is applied to the inner electrode 821, is followed by a longer period in time $t_{tr}$, during which a trapping voltage $V_{tr}$ is applied to the inner electrode 821. Referring to FIG. 9b, shown is a time-profile of the $V_{tF2}$ voltage applied to the inner electrode 841 of tFAIMS 840. The extraction pulses applied to tFAIMS 840 are offset in time compared to the extraction pulses applied to tFAIMS 820. Referring to FIG. 9c, shown is a time-profile for the CV applied to the inner electrode 801 of FAIMS 880. A different voltage is applied for transmission of ions from FAIMS 820 than is applied for transmission of ions from FAIMS 840, referred to as CV1 and CV2, respectively. Optionally, if a same ion of interest from tFAIMS 820 and tFAIMS 840 is desired, the CV of FAIMS 880 is not changed. Not shown in FIGS. 9a through 9c are the asymmetric waveform voltages (DV) applied to the inner electrodes of the three FAIMS. The polarity and the magnitude of pulses shown in FIGS. 9a through 9c are only illustrative of the timing, and the voltage and polarity of the pulses will depend on the experimental parameters including, but not limited to, the polarity of the charge on the ion of interest, the electrode to which the voltage is applied, the type of ion response to strong electric fields, gas temperature, gas pressure, and other appropriate parameters. The asymmetric waveforms applied to tFAIMS 820 and 840, and to FAIMS 880, are not necessarily identical, but it is understood that electrical parameters are selected that are suitable for the transmission of ions of interest. Optionally, the outer electrodes of tFAIMS 820 and 840, and of FAIMS 880 are held at a same applied dc voltage.

The multiple FAIMS device 800 is capable of collecting data from two independent ion streams flowing from ionization sources tFAIMS 820 and tFAIMS 840 into ion inlets 805a and 805b, respectively, of FAIMS 880. During the portion of the cycle, in which ions are extracted from ionization source tFAIMS 820 and are passing through FAIMS 880, a second stream of ions is being readied by trapping within ionization source tFAIMS 840. During the second portion of a cycle, ions are extracted from tFAIMS 840 and are passing through FAIMS 880 while a new stream of ions is being readied by trapping in tFAIMS 820. In this mode of operation the analyzing device coupled to the ion outlet 807, such as a mass spectrometer, is being used efficiently. A person of skill in the art will recognize that the principles illustrated for two ionization sources are readily extended to apply to more than two ionization sources.

The embodiment disclosed in FIG. 8a is optionally modified to decrease ion loss for some applications. For example, when either the inner electrode 841 or the outer electrode 843 of tFAIMS 840 is pulsed to extract ions into FAIMS 880, the ions collected in a trapping region 814d at the tip of the inner electrode 841 are pushed by the newly modified electric fields towards the ion outlet 847. The change of the applied voltage also disturbs equilibrium conditions that existed in the analyzer region 814b of FAIMS device 840, and the ions that were stable in the analyzer region 814b are lost to the walls. Depending on variables such as gas flow rate through tFAIMS 840 and length of the analyzer region, there will be a finite amount of time, for example, 50 to 100 ms, during which ions make their way from ion inlet 845, along the analyzer region 814b, and to the trapping region 814d of tFAIMS 840. A short path length from the ion inlet 845 to the trapping region of tFAIMS 840 will reduce ion loss and the "dead time" before ions begin to accumulate under the equilibrium conditions.

One option for further improving the efficiency of a multiple FAIMS device through the elimination of the "dead time" is to provide a disc electrode intermediate the ion outlet of a first FAIMS analyzer and the ion inlet of a second FAIMS analyzer. Referring now to FIG. 10a, shown is a simplified cross sectional view of a multiple FAIMS device according to the instant invention, in which the outer electrode 823 of FAIMS 820 is segmented into two electrically isolated segments, modified outer electrode 823m and a disk electrode 899. The analyzer region of the tFAIMS 820m is formed by the segmented outer electrode that has been divided into separate mechanically and electrically isolated components. If the two segments 823m and 899 of the outer electrode are connected electrically, or if a same voltage is applied to each segment, then the two segments 823m and 899 behave substantially as a single, non-segmented outer electrode. Referring now to FIG. 10b, which is an enlarged view of the segmented outer electrode of tFAIMS 820m, disc electrode 899 has a smaller opening than outer electrode 823m. Thus, when voltages are applied to the disc electrode 899, that differ from voltages applied to the outer electrode 823m, the disk electrode 899 modifies trapping fields in tFAIMS 820m. The ions are ejected from the trapping region 814c of tFAIMS 820m by stepwise changing the voltage applied to disc electrode 899. The advantage of this approach is that the portion of the analyzer region of FAIMS 820m that is disturbed by changes in electric fields is limited to the immediate vicinity of disc electrode 899. Electric fields present elsewhere in the analyzer region 814a are not substantially disturbed so that ions being carried by a gas flow along through the analyzer region 814a are not lost during application of an extraction pulse to the disc electrode 899. The extraction pulse removes only the ions in the trapping region, thereby causing minimal dead time between the extraction of one set of trapped ions and the onset of trapping of newly arriving ions.

Of course, at the time during which ions are being extracted from the trapping region 814c of FAIMS 820m, ions transmitted through the analyzer region 814b of FAIMS 840m are optionally being accumulated in the trapping region 814d. This is the operating condition illustrated at FIG. 10a. The alternating accumulation, or trapping, and extraction of ions from FAIMS 820m and FAIMS 840m is a very efficient operating mode for delivering ions from two independent ionization sources to a single detector or analyzer, for example a not shown mass spectrometer coupled to the ion outlet of FAIMS 880.

Further advantages associated with multiple FAIMS device 800 include the use of different carries gases in tFAIMS 820 and 840, as well as different operating temperatures. Also, irradiation sources possibly introduced at the interface between tFAIMS 820 or 840 and FAIMS 880 hold a potential to further manipulate the ion characteristics of ions introduced into FAIMS 880.

Figure 11:
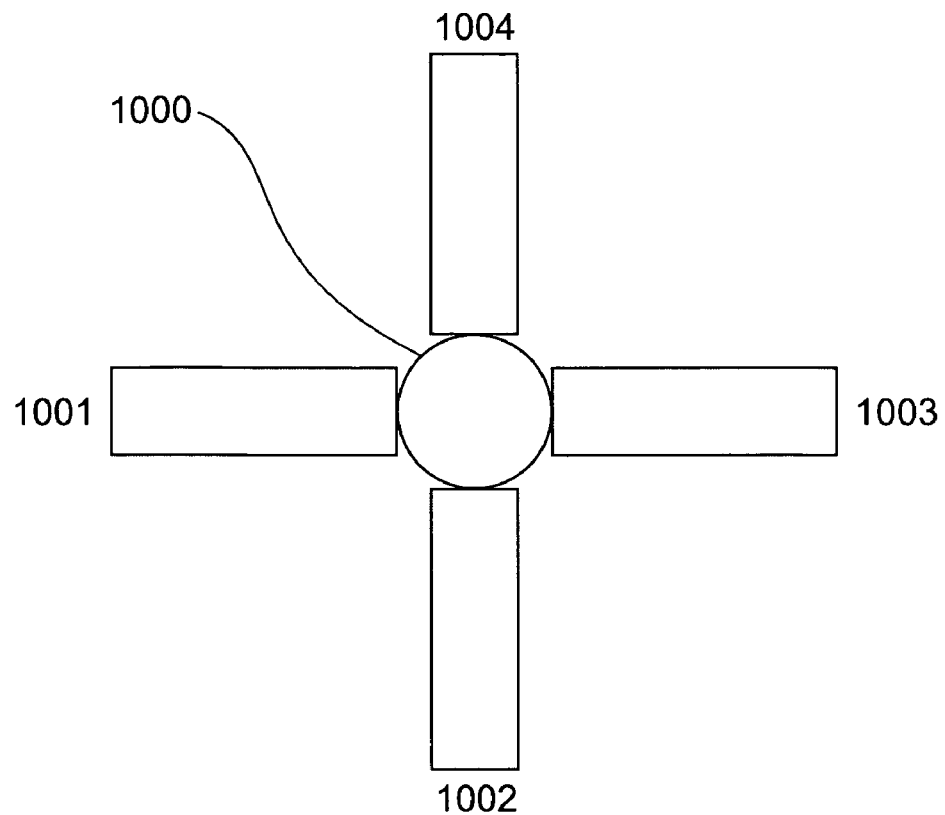
FIG. 11 shows a simplified block diagram of another multiple FAIMS device having four tFAIMS devices.
Figure 12:
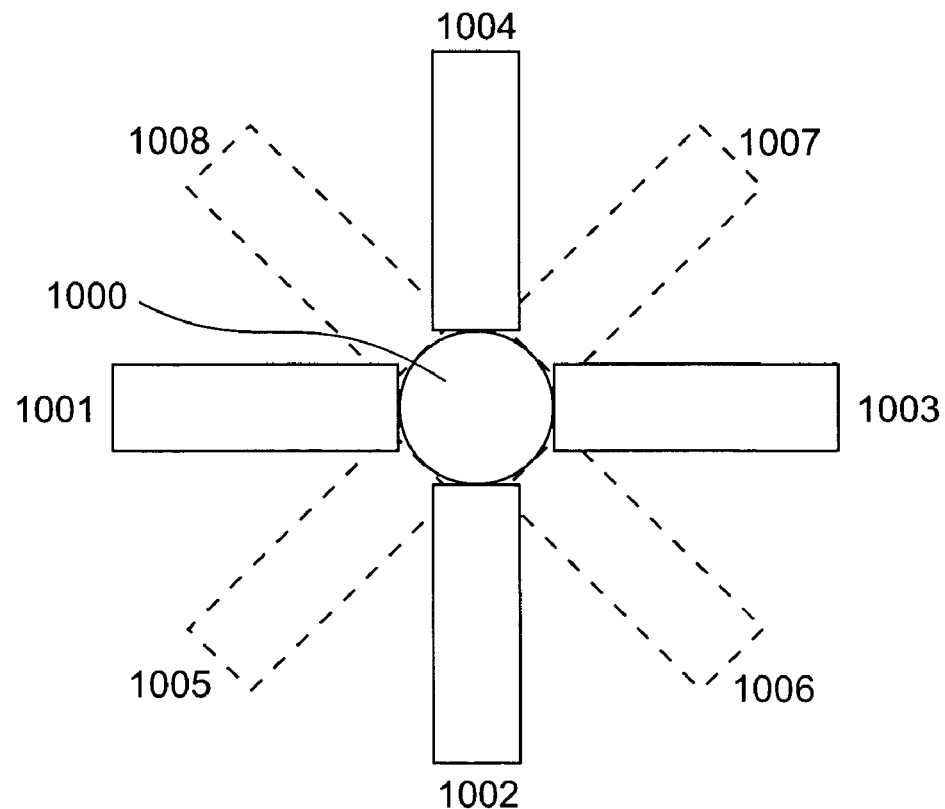
FIG. 12 shows a simplified block diagram of a multiple FAIMS device having eight tFAIMS devices.

The embodiments for a multiple FAIMS are not restricted to include two tFAIMS only. Referring now to FIG. 11, shown is a schematic view of a multiple FAIMS device, combining a FAIMS analyzer 1000 having multiple ion inlets coupled with four tFAIMS devices 1001, 1002, 1003, and 1004. In FIG. 12, shown is a schematic view of a multiple FAIMS device, combining a FAIMS analyzer 1000 having multiple ion inlets coupled with eight tFAIMS devices 1001–1008.

The number of tFAIMS devices combined with a single FAIMS operating in continuous mode is limited. Besides size constraints that physically restrict the number of tFAIMS devices mounted to the exterior of a multiple inlet FAIMS analyzer, there is also the issue of the time required for the ions to travel from a tFAIMS, through a continuous flow FAIMS wherein the multiple FAIMS device is coupled to an analyzer such as a mass spectrometer. Since the gas flow rate through the continuous flow FAIMS is controlled by the flow rate $R_m$ into the mass spectrometer, the gas flow rate through each of n tFAIMS devices is approximately $R_m/n$. At non-optimal flow rates, ion losses in each of the n tFAIMS devices increase. The problem is circumvented by allowing a portion of the carrier gas or gases to exit the continuous flow FAIMS or any of the tFAIMS other than through an ion outlet in communication with the analyzing device.

Figure 13:
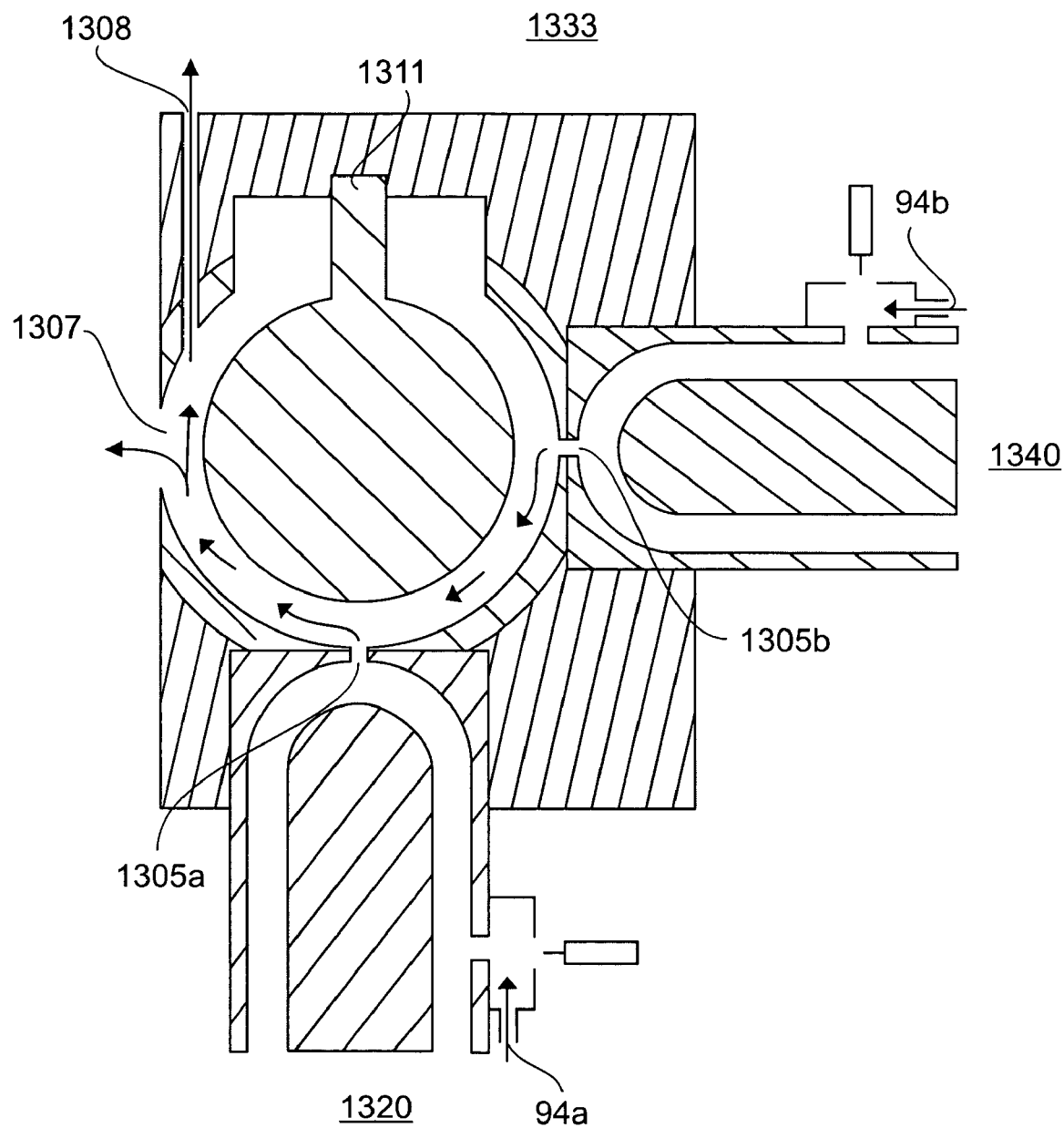
FIG. 13 shows a cross sectional side view of yet another multiple FAIMS device.

Referring now to FIG. 13, shown is a cross sectional side view of a multiple FAIMS device according to the instant invention. The multiple FAIMS device 1300 includes two trapping tFAIMS devices 1320 and 1340 attached to one side-to-side FAIMS device sFAIMS 1333 sFAIMS 1333 comprises a barrier in the form of a protrusion 1311 so that gas flows only in one direction through sFAIMS 1333, illustrated in FIG. 13 by a series of closed-headed arrows. A gas outlet 1308 is disposed near an ion outlet 1307, so that gas near the ion outlet 1307 splits into a flow exiting through the ion outlet 1307 and a flow exiting through the gas outlet 1308. Rates of curtain gas flows 94a and 94b into each of the tFAIMS devices 1320 and 1340 are important variables, since ions extracted into sFAIMS 1333 have different path lengths to the ion outlet 1307, depending on whether the ions enter at ion inlet 1305a or ion inlet 1305b. For example, if curtain gas flow 94a is significantly higher than curtain gas flow 94b, then all of a gas flow through the ion outlet 1307 originates from the gas flow through ion inlet 1305a. In this instance, the gas flow between ion inlet 1305a and ion inlet 1305b, as well as through ion inlet 1305b, is possibly reversed in direction, making it other than possible to transport ions from ion inlet 1305b to the ion outlet 1307.

The embodiments previously discussed using tandem FAIMS devices provide a means for efficiently sampling ions of interest, making improved detection possible. In the embodiments which follow, multiple ion inlets are advantageously provided for introducing ions produced at a single ion source into a FAIMS analyzer region. For instance, several types of atmospheric pressure ionization sources produce a wide ion dispersion plume. Accordingly, when using an electrospray ionization source, for example, ions and charged droplets travel along an electric field gradient in a direction away from a tip of a needle and towards a counter electrode. Unfortunately, a diverging cloud of ions is not efficiently sampled by a single small opening of the type that is commonly provided within the counter electrode of a prior art FAIMS device. A simple solution to this problem would seem to include providing a larger opening for sampling the ion plume from the ionization source. In fact, as the opening size is increased, some improvement is observed. However, in an experiment with singly charged ions of leucine enkephalin, when a 2 mm opening is compared to a 1 mm opening, only a 35% increase in absolute signal intensity is observed, compared to a 300% increase in the area of the opening. It is likely that the signal intensity does not increase in proportion to the increase to the area of the opening because the resulting changes to gas flows and electric fields in the region near an ion inlet affect the efficiency of transfer of ions into a FAIMS analyzer region. For example, a strong electric field between the inner and outer electrode of a FAIMS device that is necessary for its operation decreases significantly if there is a discontinuity in either the inner or outer electrodes, such as a hole in the outer electrode. If the hole is small, and if its diameter is less than a spacing between inner and outer electrodes, electric fields in the region between the hole and the inner electrode remain similar to fields elsewhere between the inner and outer electrode. However, if the hole is large, its diameter being for example twice the spacing between the inner and outer electrodes, electric fields decrease in strength between the hole and the inner electrode. Ions, which would otherwise have been focused under the operating conditions of CV and DV, will hit one of the inner and outer electrodes and be lost. Therefore, further increases in size of an ion inlet are not expected to give significantly improved results.

Figure 14A:
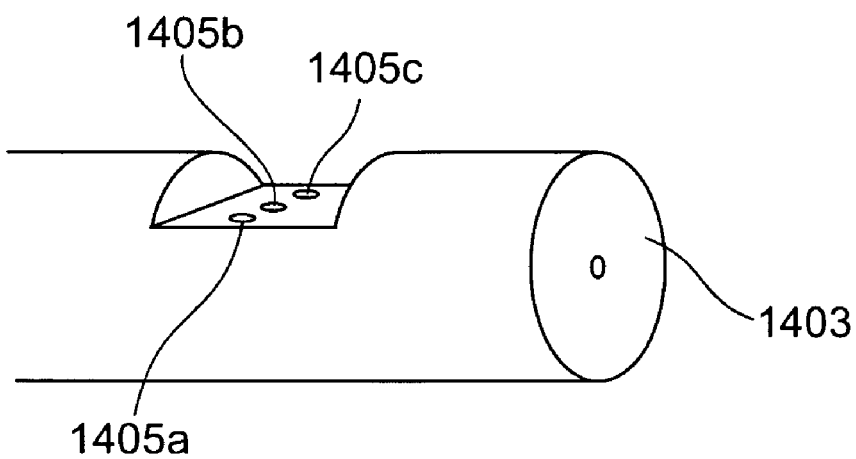
FIG. 14a shows a schematic view of a FAIMS outer electrode having a first ion inlet grouping.
Figure 14B:
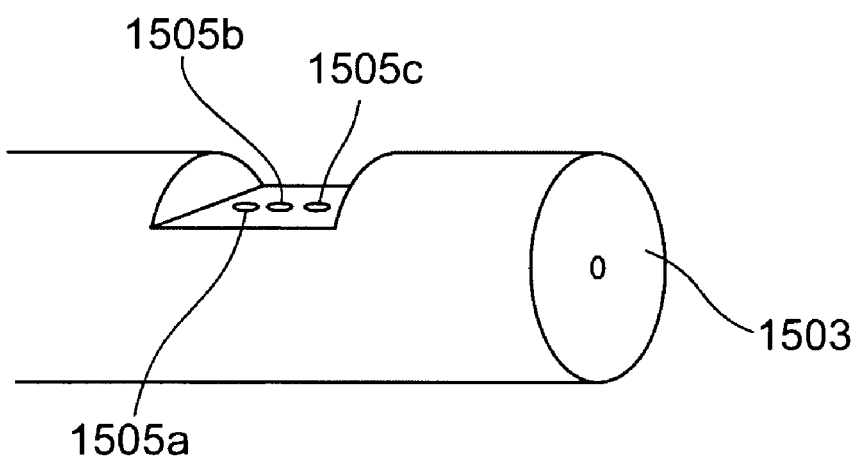
FIG. 14b shows a schematic view of a FAIMS outer electrode having a second ion inlet grouping.
Figure 14C:
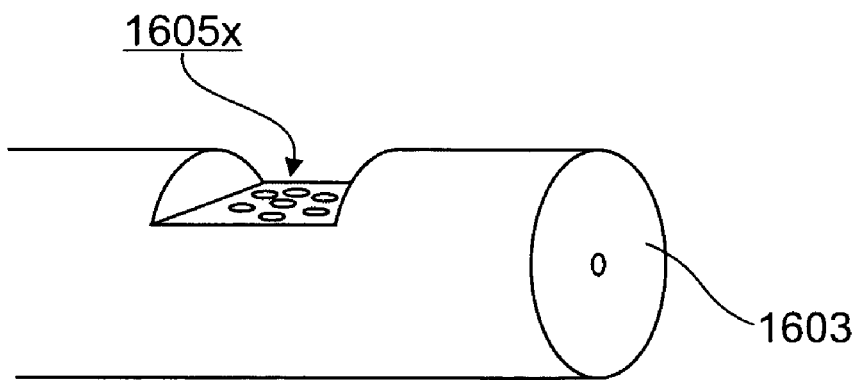
FIG. 14c shows a schematic view of a FAIMS outer electrode having a third ion inlet grouping

Increased sample introduction is achieved by providing several openings in the outer electrode of a FAIMS device, such as is illustrated at FIGS. 14a–c. The multiple ion inlet groupings that are shown at FIGS. 14a–c result in a significant improvement in the observed signal intensity relative to a device with a single small opening. In FAIMS devices having a separate desolvation chamber, a counter electrode or curtain plate is located in front of the ion inlet. Therefore, provision is made for the curtain plate to have openings of at least the same size, and in the same position, as the openings in the ion inlet groupings of the outer electrode. Preferably, the openings in the curtain plate are somewhat larger to allow for maximal ion transmission through the curtain plate, while at the same time satisfying the condition of an area of holes that does not become so large as to prevent efficient desolvation. If the holes are large, the gas flow velocity is not constant across the diameter of the hole. If there are several such holes, flow through one hole may exceed flow though other holes, and if flow velocity or flow volume is decreased, an inefficient desolvation of ions may result. Poor desolvation reduces an effectiveness of ion separation in the analyzer region of a FAIMS device, and if neutral solvent vapours contaminate gas flowing into a FAIMS analyzer, the FAIMS device is likely to fail. For the use of several ion inlets, a reduction in the size of each ion inlet is advisable to allow for efficient desolvation. In FAIMS devices not having a separate desolvation chamber, the ion inlets are of a suitable size for maintaining sufficient velocity of gas flowing out of the analyzer region through the ion inlets for desolvation to occur. Numerous configurations of multiple ion inlet groupings are possible and the ion inlet groupings shown at FIG. 14 should not be considered an exclusive list of possible configurations. In addition, as long as the total area of the ion inlet does not become too large for ion desolvation, the ion inlet size is not restricted to a particular dimension, nor does the size of each ion inlet need to be kept equal. The location of an ion inlet grouping or of multiple ion inlet groupings on an outer electrode is variable. With a domed FAIMS device, ion inlets are to be placed at any location around the circumference of the outer electrode at a same distance from an ion outlet. A location of an ion inlet is also adjustable along a length of an outer electrode. Moving the ion inlet farther away from the an ion outlet increases ion transit time, possibly causing a reduction in signal intensity due to loss mechanisms such as diffusion and space charge repulsion. Moving the ion inlet closer toward an ion outlet possibly improves sensitivity due to reduced ion transit time. However, if the ion inlet is placed too close to the ion outlet, insufficient time for ion separation results in a reduction of peak separation capabilities of a FAIMS device.

Referring specifically to FIG. 14a, shown is a schematic view of a FAIMS outer electrode having a first ion inlet grouping according to the instant invention. A FAIMS device comprises an outer electrode 1403 having a length. In the outer electrode 1403, disposed are three circular ion inlets 1405a–c, the ion inlets 1405a–c positioned on a line substantially perpendicular to the length of the outer electrode.

Referring specifically to FIG. 14b, shown is a schematic view of a FAIMS outer electrode having a second ion inlet grouping according to the instant invention. A FAIMS device comprises an outer electrode 1503 having a length. In the outer electrode 1503, disposed are three circular ion inlets 1505a–c, the ion inlets 1505a–c positioned on a line substantially parallel to the length of the outer electrode.

Referring specifically to FIG. 14c, shown is a schematic view of a FAIMS outer electrode having a third ion inlet grouping according to the instant invention. A FAIMS device comprises an outer electrode 1603 having a length. In the outer electrode 1603, disposed is a plurality of essentially circular ion inlets, shown generally at 1605x, the plurality of ion inlets 1605x positioned so as to adopt a two-dimensional closest packing of circles.

Figure 15A:
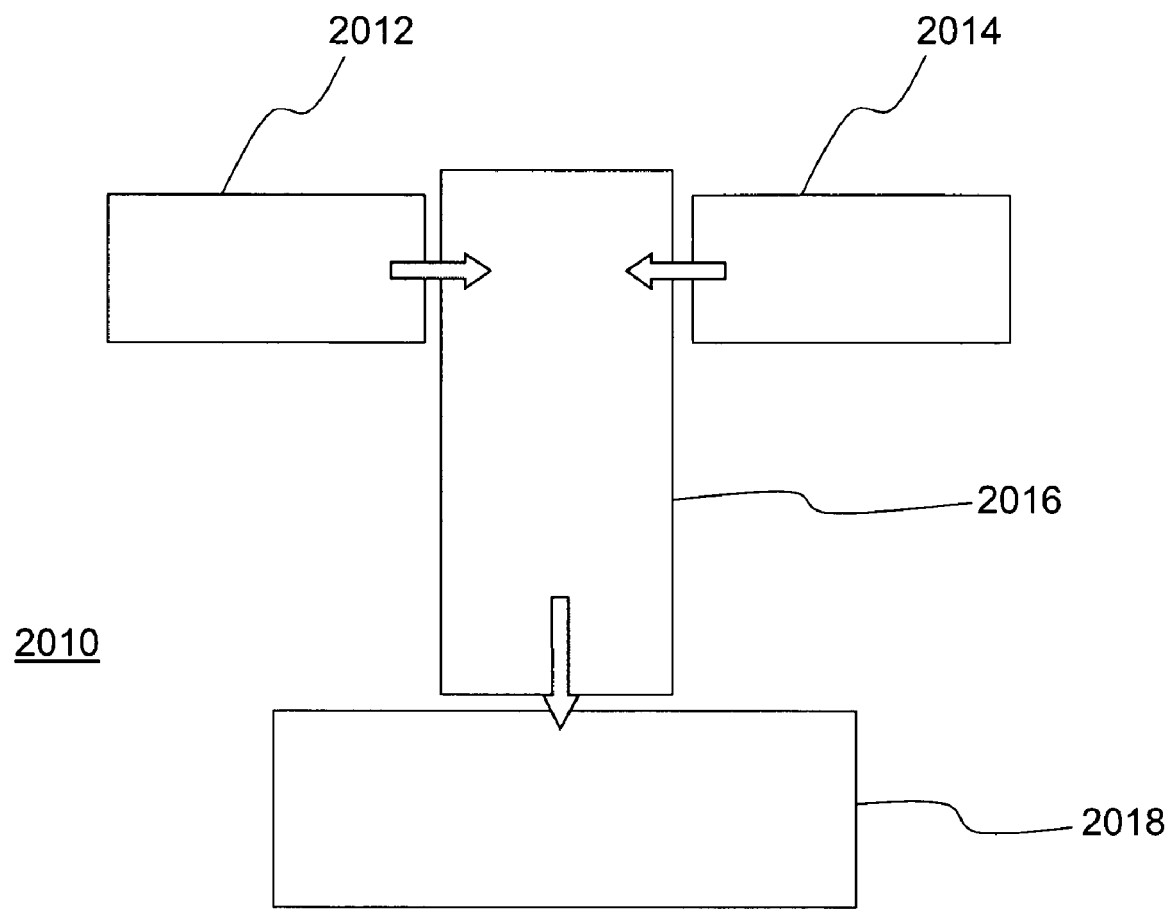
FIG. 15a is a simplified block diagram of an apparatus for providing ions from a plurality of ionization sources to a same mass spectrometer inlet orifice.
Figure 15B:
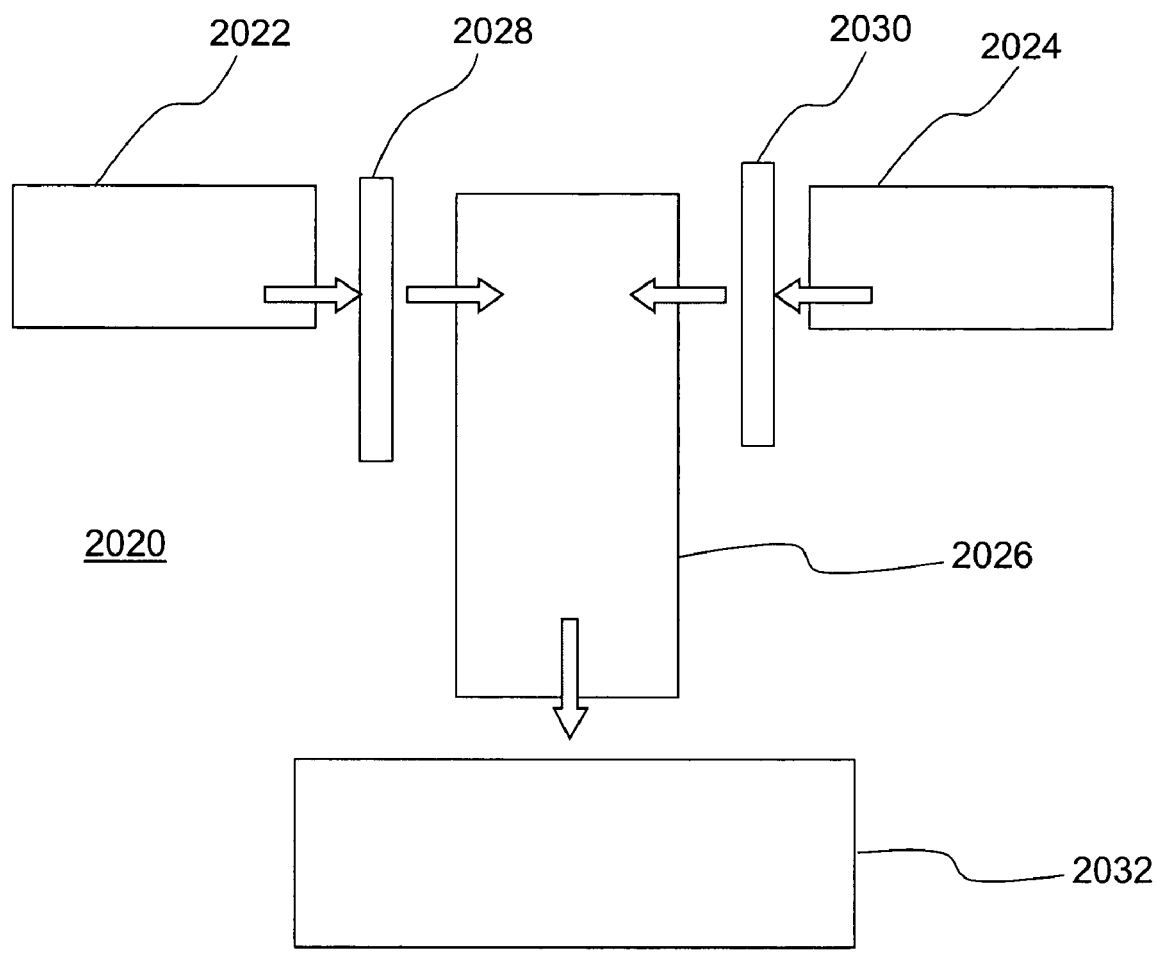
FIG. 15b is a simplified block diagram of another apparatus for providing ions from a plurality of ionization sources to a same mass spectrometer inlet orifice.

Referring now to FIGS. 15a and 15b, shown are simplified block diagrams of two systems for multiplexing plural flows of ions into one stream of ions for subsequent delivery to an orifice leading into a vacuum chamber of a mass spectrometer, or for delivery to some other suitable ion detecting device. In the instant example, which is not intended to be limiting in any way, two separate ionization sources are operated independently in time and may optionally represent more than one type of ionization source including, but not limited to, electrospray ionization (ESI), photoionization, chemical ionization, matrix assisted laser desorption ionization (MALDI), etc. Combining ion streams "post-source" using FAIMS has several advantages including: (1) rapid switching of streams, (2) minimum memory of ions originating in other streams, (3) no solvent compatibility or mixing considerations, (4) incompatible ionization sources can be run independently in parallel, and (5) minimum ion-ion or ionic charge-exchange reactions to change the relative abundances of species. In contrast, those approaches that involve mixing of liquid streams prior to ionization suffer from many limitations, most of which are eliminated using one of the systems shown in FIG. 15a and 15b.

Referring specifically to FIG. 15a, illustrated is a system 2010 including two ionization sources 2012 and 2014. The system 2010 shown at FIG. 15a is similar to the systems that are shown at FIG. 4, FIGS. 5a–5c, and FIGS. 6a–6b. During use, ions that are produced separately at the two ionization sources 2012 and 2014 are introduced into collector FAIMS 2016 through a conventional desolvation transport system (not illustrated), a curtain plate for example, without modification of the streams of ions.

The system 2010 comprises two or more ionization sources 2012 and 2014, each ionization source 2012 and 2014 being in fluid communication with a separate ion inlet (not illustrated) of a plurality of ion inlets of collector FAIMS 2016. The conventional ionization sources 2012 and 2014 are optionally of a same type, or alternatively the conventional ionization sources 2012 and 2014 are of different types. For example both ionization sources 2012 and 2014 are electrospray ionization (ESI) sources, or both ionization sources 2012 and 2014 photoionization sources, or one ionization source 2012 is an ESI source whilst the other ionization source 2014 is a photoionization source. Of course, other combinations of ionization source types will be apparent to one of skill in the art.

The main advantage of system 2010 shown in FIG. 15a is its mechanical simplicity and capability to maintain separate liquid or gas streams carrying sample for ionization. This eliminates the many problems discussed earlier relating to the mixing of liquid streams. Each ionization source is selected independently of the other and is operable at its optimum conditions independent of the other. Optional methods of cutting off one or more ion streams using gas flows, or changes to voltages on the curtain plate offer methods of expanding the utility of the single-FAIMS ion stream multiplexer shown at FIG. 15a.

However, the system shown at FIG. 15a has some limitations. Since only one collector FAIMS 2016 is provided, the ions from both ionization sources 2012 and 2014 are delivered to a mass spectrometer 2018 if both ionization sources 2012 and 2014 produce ions that are transmitted at the particular operating conditions of CV, DV, gas type, pressure, temperature, electrode spacing, etc. of the collector FAIMS 2016. For example, assume that the ionization source 2012 produces a reference ion (alternatively referred to as ions of a calibration species) for calibration of the mass scale and that the other source 2014 is in fluid communication with a reservoir of a sample solution. Assume also that the mass calibration ion is transmitted at CV=−10 volts. In operation, at various times the collector FAIMS 2016 is set to this CV to deliver the reference ions to the mass spectrometer 2018. Clearly, any ions that are also transmitted at CV=−10 volts from the sample source 2014 are simultaneously delivered to the mass spectrometer 2018. This is not a problem unless the sample solution contains ions that interfere with the mass calibration reference ions, by appearing at very similar mass. Even then, this problem may be compensated for, since the calibration solution may be prepared with the reference compound at high concentration.

Similarly, if ions of interest from the sample are transmitted at CV=−15 volts, any ions originating from the calibration solution that are transmitted at CV=−15 volts are also delivered to the mass spectrometer 2018, and thus are superimposed upon the spectrum of the sample. This is not a severe problem since the reference ions are easily identified and ignored during data processing. However, if the ions are background ions, then these ions cannot be easily identified or ignored, and therefore they will contribute to background chemical noise.

Complete switching between ion streams requires the unambiguous elimination of the ion stream from the non-selected source. The source can be turned off or, alternately, isolated from the FAIMS analyzer by means such as those previously described in FIGS. 4 to 6. By way of example and still referring to FIG. 15a, if the ionization source 2012 is an electrospray ionization source, the curtain plate voltage can be set so as to prevent the flow of ions into the FAIMS device. Alternately, gas flows in the FAIMS system can be controlled.

Referring now to FIG. 15b, illustrated is a system 2020 including two ionization sources 2022 and 2024. The system 2020 shown at FIG. 15b is similar to the systems that are shown at FIGS. 7a–7h having an ion gate in the form of a rotating ion source selector electrode. Referring still to FIG. 15b, during use the ions that are produced separately at the two ionization sources 2022 and 2024 are introduced into collector FAIMS 2026 in a controllable and selective manner. In particular, a first electronic or mechanical ion gate 2028 associated with the first ionization source 2022 controllably introduces a first stream of ions produced at the first ionization source 2022, whilst a second electronic or mechanical ion gate 2030 associated with the second ionization source 2024 controllably introduces a second stream of ions produced at the second ionization source 2024. System 2020 supports two modes of operation, one mode in which only ions from a selected one of the two ionization sources 2022 and 2024 are detected by the mass spectrometer 2032 at a time, and another mode in which ions from both of the two ionization sources 2022 and 2024 are detected by the mass spectrometer 2032 at a time.

Although somewhat more complex compared to the system shown at FIG. 15a, nevertheless the system shown at FIG. 15b is a particularly suitable option for cases where it may be necessary to completely cut off one of the ion streams. The presence of an ion gate may cause a reduction in signal intensity.

Figure 16:
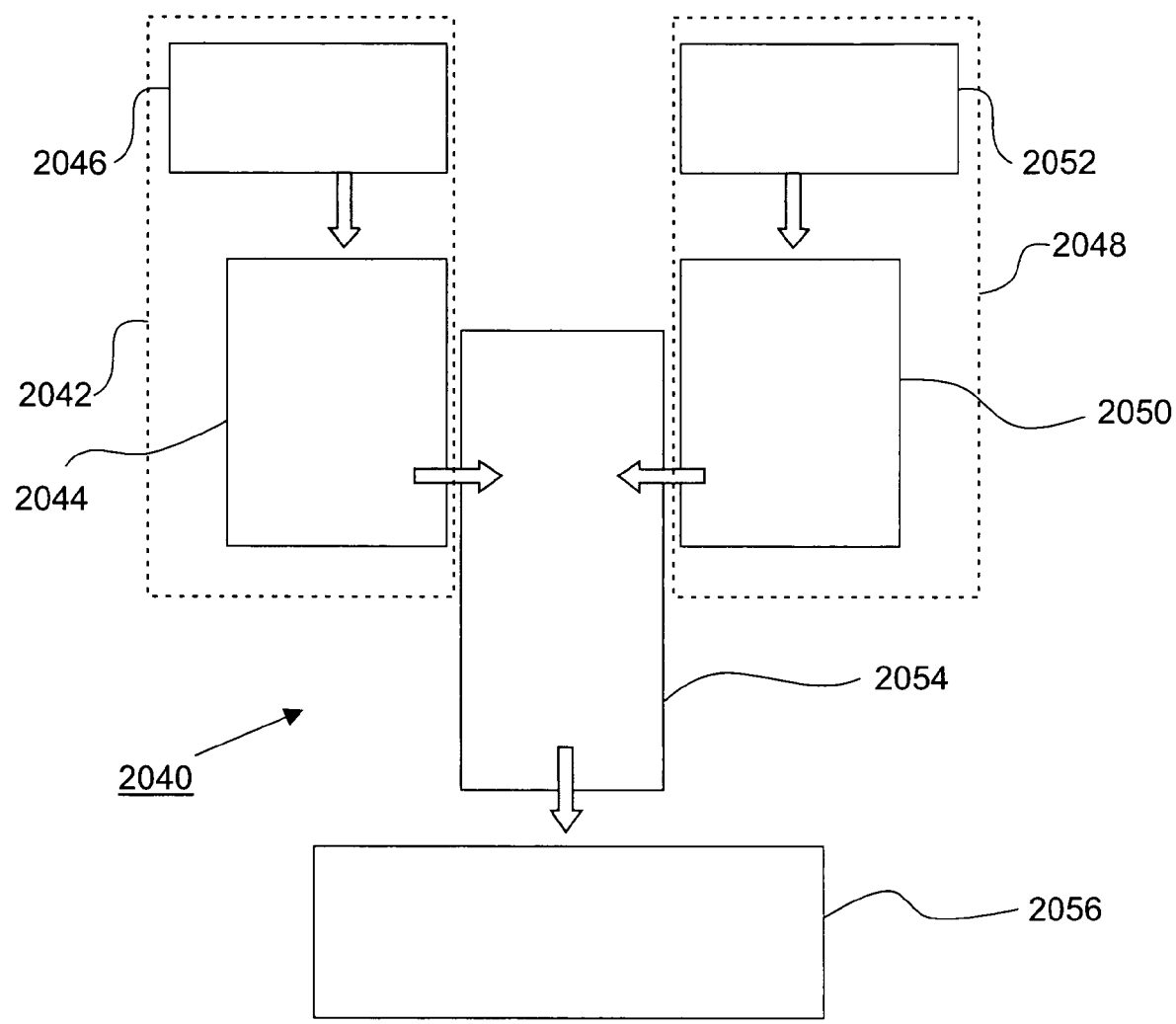
FIG. 16 is a simplified block diagram of still another apparatus for providing ions from a plurality of ionization sources to a same mass spectrometer inlet orifice.

Referring now to FIG. 16, shown is a simplified block diagram of a multi-source FAIMS system 2040, including a first tandem-source/FAIMS portion 2042 having a first FAIMS 2044 associated with a first ionization source 2046, and a second tandem-source/FAIMS portion 2048 having a second FAIMS 2050 associated with a second ionization source 2052. Separate ion streams from two or more such tandem-source/FAIMS portions 2042, 2048 are combined within a single collector FAIMS 2054, which subsequently provides the resulting combined ion stream via a not illustrated ion outlet therefrom and into a not illustrated ion inlet orifice of a mass spectrometer 2056.

Optionally, the system of FIG. 16 is operated in an ion-switching mode by ensuring that electrical field conditions within the FAIMS of a given tandem-source/FAIMS portion 2042 or 2048, and within the collector FAIMS 2054, are suitable for transmission of an ion of interest. At the same time, the non-active tandem-source/FAIMS portion 2042 or 2048 is operated with different electrical field conditions, which are selected to be unsuitable for transmission of the ion of interest. Several examples illustrating possible different operating conditions are considered below.

In a first specific and non-limiting example of an ion-switching mode, the ions from a first tandem-source/FAIMS portion 2042 are delivered to the mass spectrometer 2056 for a first known period of time, via the collector FAIMS 2054. After this first known period of time, the electrical field conditions within the various FAIMS are altered, so as to allow the ions from a second tandem-source/FAIMS portion 2048 to be transmitted to the mass spectrometer 2056 during a second known period of time, also via the collector FAIMS 2054. Ions from both tandem-source/FAIMS portion 2042 and 2048 are measured by the mass spectrometer 2056 by the end of the second known period of time. A more detailed example is presented below.

In the instant specific and non-limiting example, a computer-controlled system is used to change voltages, and to collect mass spectra in such a way as to ensure that the user knows which mass spectrum came from which ion source. Accordingly, the mass spectra are indexed to a particular ion source. The ions are carried through each FAIMS illustrated at FIG. 16 by the action of at least one of a flow of gas and a voltage gradient. The ions require finite time to be transmitted through each FAIMS. For example, if the voltage conditions are changed from CV=−5 volts which transmits ion A, to CV=−10 volts which transmits ion B, time is required before the exit stream of ions is composed of ion B. This process of changing the outlet streams occurs in a series of stages. Soon after the voltages are changed, all of ions A collide with the walls of FAIMS. The transmission of A is cut off fairly abruptly. Essentially no memory of the A ions persists. Also, soon after the voltage change, the B ion is successfully transmitted by the FAIMS, but does not appear at the outlet for a period of time corresponding approximating to the time it takes for the gas flow (for example) to carry ions through the FAIMS. For some time after the voltage change has occurred, no ions may be flowing out of the outlet of this FAIMS.

An in-depth understanding of the operations of the FAIMS in the system in FIG. 16 suggests several modes of operation available to the user.

In one mode of operation the user requires measurement of a stream of ions produced at ionization source 2046, which will be called ion stream #1, at CV=−5 volts and measurement of a stream of ions produced at ionization source 2052, which will be called ion stream #2, at CV=−10 volts. Proposed operation is as follows. Both the first FAIMS 2044 and collector FAIMS 2054 are operated at the first voltage CV=−5 volts for a first period of time. The ion stream #1 passes through first FAIMS 2044 and through collector FAIMS 2054 and is delivered to the mass spectrometer 2056. At the end of the first period of time, it is desired that the ions from ion stream #2 be sampled. One possible option is to change simultaneously both the second FAIMS 2050 and the collector FAIMS 2054 to CV=−10 volts. Since both voltages have been changed, all ions existing in both the second FAIMS 2050 and collector FAIMS 2054 are lost. The ions of ion stream #2 begin to enter the second FAIMS 2050, pass through the second FAIMS 2050, begin to enter the collector FAIMS 2054, pass through the collector FAIMS 2054 and then enter the mass spectrometer 2056. This approach introduces a period of time during which no ions enter the mass spectrometer 2056, and thus the mass spectrometer is somewhat under-utilized. Switching between sample streams as described above creates a "dead-time" of no ion transmission.

Despite the under-utilization of the mass spectrometer 2056 inherent to the method described above, the method is simple to implement and therefore advantageous in some cases.

The voltage conditions of the FAIMS of the non-active stream are considered next. In a first approach, the voltages of FAIMS 2044 and 2050 are never changed. For example, if ion stream #1 requires CV=−5 volts and ion stream #2 requires CV=−10 volts, it would appear unnecessary to change these voltages in the respective FAIMS 2044 and 2050. Only the voltage that is applied to the collector FAIMS 2054 need be alternated between these two CV values, thereby selecting the desired ion stream. This also shortens the dead-time between switching voltages, since the ions are already passing through both respective FAIMS 2044 and 2050, and the dead-time is controlled only by the transit times through the collector FAIMS 2054. Of course, this approach fails when both ion streams #1 and #2 must be sampled at the same CV. With the collector FAIMS 2054 set at this common CV, the mass spectrum is the sum of ions of both ion streams #1 and #2. This may or may not be a problem, as was discussed with reference to FIG. 15a.

If the limitation of allowing the voltages of FAIMS 2044 and 2050 of the respective ion streams to remain fixed must be overcome, then the voltages applied to the FAIMS of the non-active ion stream should also be considered. Several options are available. First, the voltages applied to the non-active FAIMS are changed to a non-transmitting state. For example: (1) the CV is changed to a value for which no known ions are transmitted, including for example CV=−200 volts, or (2) the polarity of the CV is switched, for example CV=−5 is changed to CV=+5 so that few, if any ions are transmitted, or (3) the waveform is changed to DV=0 where no ions are transmitted at a non-zero applied CV or (4) the waveform remains active but the asymmetry is removed by phase shifting one of the two constituent sinusoidal waveforms so that no ions are transmitted at a non-zero applied CV, or (5) the CV is changed rapidly between two differing values so that no ions are transmitted during the non-active time. These are intended to be non-limiting examples, and many other options are possible.

If the voltages applied to the FAIMS of the non-active stream effectively prohibit any ion transmission, then the switching between streams is inefficient. The dead-time required for ions from a newly selected stream to arrive at the mass spectrometer is equal to the time required for the gas to carry the ions through the FAIMS of the active stream and subsequently through the collector FAIMS 2054. Improved efficiency is attainable by a judicious selection of the times of voltage switching. In one approach the voltages to the FAIMS of the newly selected stream, for instance ion stream #2, are switched early, before the voltage applied to the collector FAIMS 2054 is switched. This allows time for the ions of ion stream #2 to be transmitted through the FAIMS, and then be immediately available to the collector FAIMS 2054 at the time of changing voltages applied to this collector FAIMS 2054. The dead-time of arrival of ions to the mass spectrometer equals approximately the time for the gas (for example) to transport the ions from an entrance to an exit of the collector FAIMS 2054.

The system in FIG. 16 offers yet another non-obvious advantage over the simple system shown at FIGS. 15a and 15b. The separation and transmission of cylindrical geometry FAIMS is a function of the radii of the inner and outer electrodes. Assuming that the space between the electrodes is fixed, narrow diameter electrodes provide an advantage of producing a stronger focusing action of ions between the electrodes. This means that the ions are pulled into a narrower-width radial region than they would be in a device with wider diameter electrodes. This stronger focusing has the benefit of higher transmission efficiency and has the benefit of transmission of a given ion over a wider range of applied compensation voltage (CV). These properties make a FAIMS with narrow diameter electrodes suitable for the collector FAIMS 2016, 2026 and 2054 shown at FIGS. 15a, 15b, and 16, respectively. However the resolution of ion separation is lower with these narrow diameter electrodes, compared to a system with wider diameter electrodes having the same width of annular space between the electrodes. The system shown at FIG. 16 is optionally designed with electrodes of differing diameters. For example, the FAIMS of tandem-source/FAIMS portions 2042 and/or 2048 have wide diameters (thus good ion separation resolution), whereas the collector FAIMS 2054 may be narrow diameter for efficient collection of the streams of ions and for maximum ion transmission efficiency. The combination of these systems as shown in FIG. 16 permits good overall resolution of ion separation as well as high overall efficiency of the delivery of ions to the orifice leading to the vacuum chamber of the mass spectrometer 2056.

It should be noted that the system shown at FIG. 16 appears to be very similar to the systems described supra with reference to FIG. 8a through FIG. 13. The systems shown at FIG. 8a through FIG. 13 all include an assembly of FAIMS devices that is configured as a special version of an ion switch, much like the assembly of FAIMS devices that is shown at FIG. 16. However, the assemblies of FAIMS devices in the systems shown at FIG. 8a through FIG. 13 are all specifically configured to trap the flows of ions originating in the non-active inlets, while the ions from a selected (active inlet) are delivered to the mass spectrometer. Accordingly, the systems described supra with reference to FIG. 8a through FIG. 13 are configured to optimize efficiency of transmission of ions from all of the multiplexed inlets into the mass spectrometer. Other similar approaches have been discussed in WO 01/69221, filed Mar. 14, 2001 in the name of Guevremont et al., and in Journal of the American Society for Mass Spectrometry 2001, 12, pp. 1320–1330, the contents of both of which are incorporated by reference herein.

In contrast, the assembly of FAIMS devices in the system shown at FIG. 16 does not include ion trapping FAIMS, and accordingly the ions are not trapped prior to delivery to the collector FAIMS. By eliminating the need to trap the ions, the system of FIG. 16 is made simpler to build and operate. However, the penalty for this simplification is loss of signal through limited duty cycle for each ion source. In the simplified ion switching system of FIG. 16, the ions from the non-active stream collide with the FAIMS electrodes by application of CV values beyond transmission of any known ions. The active inlet FAIMS, and the collector FAIMS are both operated to transmit the ions of interest. Optionally, the change of active stream of ions is preceded by changing the CV of the next FAIMS to the required value early, so as to permit time for the ions to travel through the next FAIMS. This pre-change of CV permits higher efficiency of the system 2040. The cut-off of a stream is immediate, since a drastic change of CV will stop the ion stream with only a very short delay.

Figure 17A:
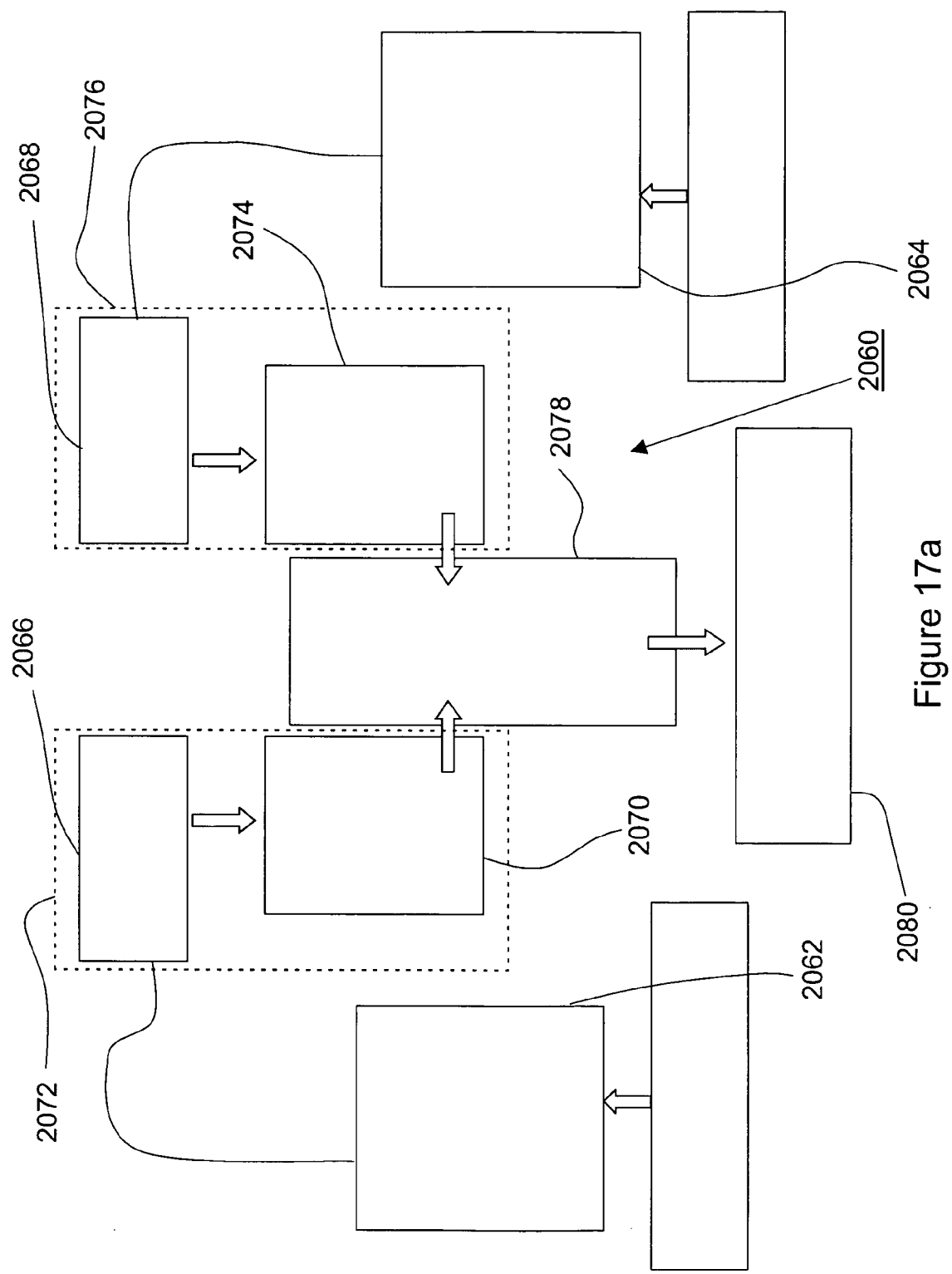
FIG. 17a is a simplified block diagram showing the apparatus of FIG. 16 connected to a plurality of HPLC systems.

FIG. 17a illustrates a more complex analytical system, including separation of compounds in samples using high performance liquid chromatography (HPLC) 2062 and 2064, prior to ionization of the samples using independent ionization sources 2066 and 2068, respectively. Because the ions are multiplexed using a post-ionization FAIMS system 2060, the HPLC systems may be operated independently, and even with solvents that are immiscible. The ionization sources may be the same or different, for example, the first ionization sources 2066 being a photoionization source, and the second ionization source 2068 being an ESI source. The system 2060 includes a first FAIMS 2070 associated with the ionization source 2066, which together form part of a first tandem-source/FAIMS portion 2072, and a second FAIMS 2074 associated with the ionization source 2068, which together form part of a second tandem-source/FAIMS portion 2076. The system 2060 further includes a collector FAIMS 2078. Each tandem-source/FAIMS portion 2072 and 2076 is in fluid communication with a separate ion inlet (not illustrated) of a plurality of ion inlets of collector FAIMS 2078. The collector FAIMS 2078 also has an ion outlet, which is disposed proximate to and in fluid communication with a not illustrated orifice of mass spectrometer 2080.

Figure 17B:
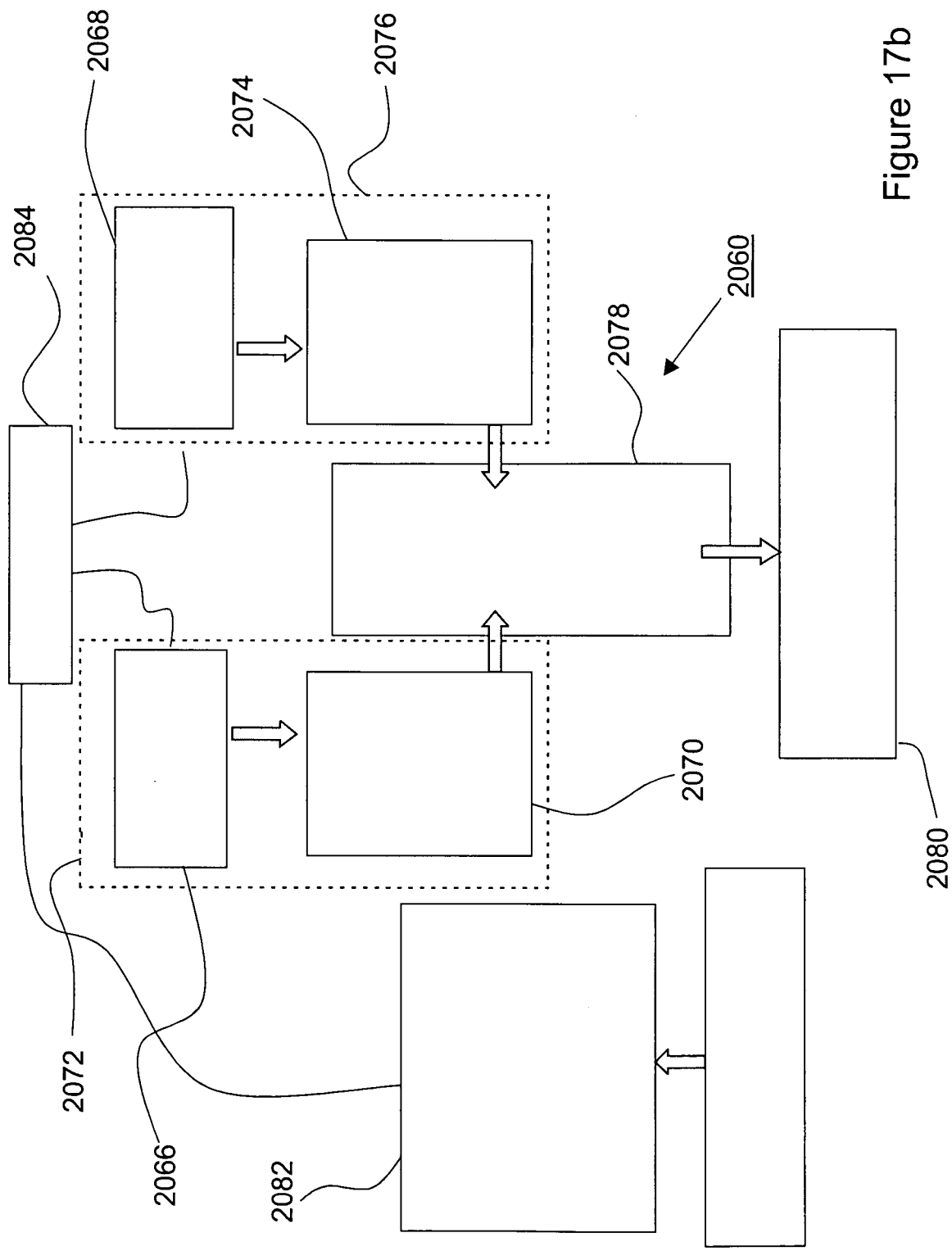
FIG. 17b is a simplified block diagram showing the apparatus of FIG. 16 connected to a single HPLC system, with an effluent splitter in communication with two different types of ionization sources.

Optionally, as shown at FIG. 17b, effluent from a single HPLC separation system 2082 is split using a splitter 2084, for introduction into two or more types of ionization sources 2066 and 2068. It is efficient utilization of the mass spectrometer to detect ions from several types of ionization sources, thus eliminating the need to change ionization sources and re-run the HPLC separation with the new source.

Figure 17C:
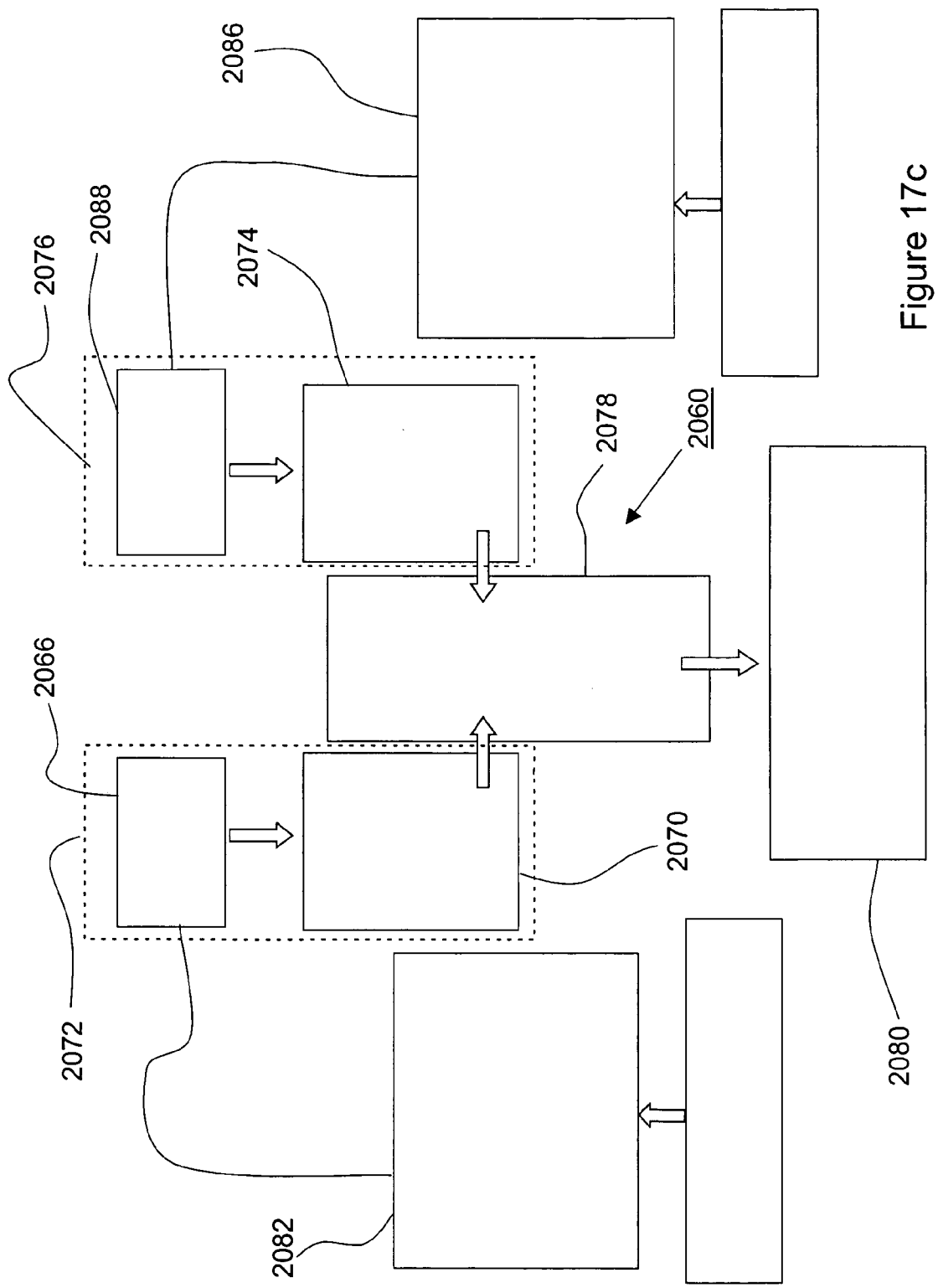
FIG. 17c is a simplified block diagram showing the apparatus of FIG. 16 connected to a single HPLC system and a single GC system.

Further optionally, as shown in FIG. 17c, effluent from incompatible separation technologies, such as for example HPLC 2082 and a gas chromatograph (GC) 2086, is introduced into two or more types of ionization sources 2066 and 2088. In FIG. 17c the effluent of the HPLC 2082 is ionized in a conventional ESI source 2066, whereas the effluent from GC 2086 is ionized using corona discharge or radioactivity for atmospheric pressure chemical ionization 2088.

In FIGS. 15a through 17c the FAIMS are optionally provided as one of cylindrical geometry FAIMS, domed FAIMS, side-to-side geometry FAIMS, flat plates FAIMS, spherical geometry FAIMS, as non-limiting examples. Of course, different combinations of FAIMS geometries may be used. For instance, the FAIMS of a first tandem-source/FAIMS may be provided as a cylindrical geometry FAIMS with large diameter electrodes, the FAIMS of a second tandem-source/FAIMS may be provided as a side-to-side FAIMS, and a collector FAIMS that is in communication with each one of the first and second tandem-source/FAIMS may be provided as a cylindrical geometry FAIMS with small diameter electrodes. Further examples are shown below, in order to examine and to clarify the wide scope of possible embodiments of the invention.

Figure 18A:
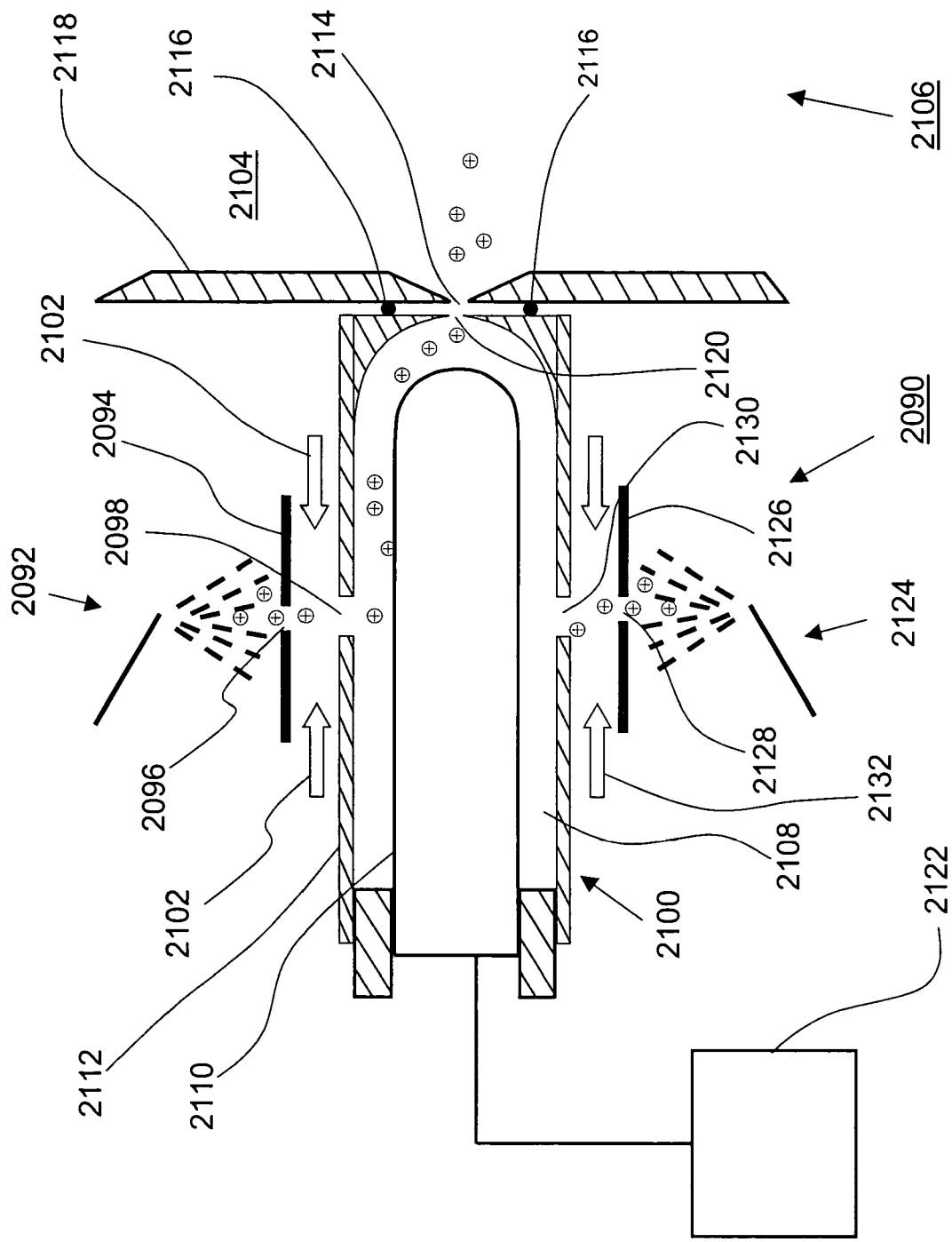
FIG. 18a is a simplified schematic diagram of an embodiment of the apparatus shown at FIG. 15a in a first mode of operation.
Figure 18B:
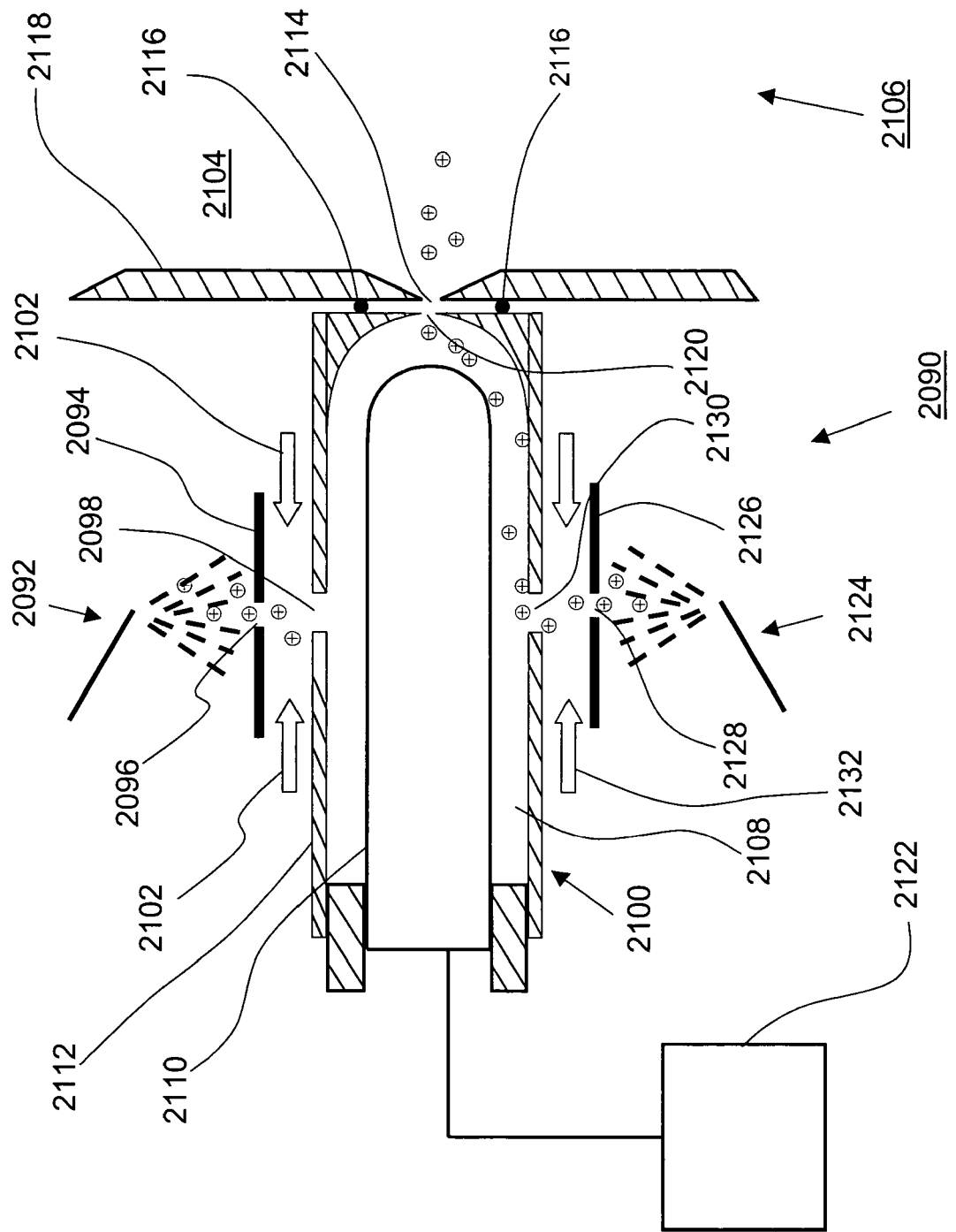
FIG. 18b is a simplified schematic diagram of an embodiment of the apparatus shown at FIG. 15a in a second mode of operation.

FIG. 18a and FIG. 18b illustrate one specific example of an embodiment 2090 of the concept shown in FIG. 15a, but with greater detail than is shown at FIG. 15a. During use, as shown at FIG. 18a, a stream of ions produced at ESI source 2092 is transmitted against a flow of desolvation gas coming out through an aperture 2096 defined within a curtain plate 2094. The ions having passed through aperture 2096 are carried by a gas stream through a first ion inlet 2098 and into a domed version of FAIMS 2100. In particular, curtain gas 2102 delivered to the space between the curtain plate 2094 and FAIMS 2100 divides into two streams, the first flowing out of the aperture 2096 in the curtain plate 2094 and forming the flow of desolvation gas, and the second flowing into FAIMS, being pulled through FAIMS by a flow entering the vacuum chamber 2104 of the mass spectrometer 2106. The mixture of ions carried into the first inlet 2098 of FAIMS 2100 is separated via loss of some of the ions that collide with the walls of the FAIMS electrodes. The surviving sub-set of ions from ESI source 2092 (as selected by application of appropriate voltages to the FAIMS electrodes and composition of transporting gas) are transmitted along an annular analyzer region 2108 between an inner FAIMS electrode 2110 and an outer FAIMS electrode 2112, and through the FAIMS to the tip of the domed inner electrode 2110. The sub-set of ions is drawn away from the tip of the domed inner electrode 2110 and through an orifice 2114 in an orifice plate 2118 of the mass spectrometer 2106 by the flow of gas into the vacuum chamber 2104. Gas-tight seals 2116 are disposed between the FAIMS 2100 and the orifice plate 2118 of the mass spectrometer 2106. As noted above, a portion of the curtain gas 2102 is pulled into the analyzer region 2108 of FAIMS 2100 and carries the ions along the analyzer region 2108 to an outlet aperture 2120 of FAIMS, the outlet aperture 2120 being disposed adjacent to and in fluid communication with the orifice 2114 in orifice plate 2118 of the mass spectrometer 2106. Subsequently, this mixture of gas and ions is drawn into the vacuum chamber 2104 of the mass spectrometer 2106. Of course, an electronic power and control system 2122 applies a combination of an asymmetric waveform voltage and direct current voltage between the inner electrode 2110 and the outer electrode 2112. For instance, the electronic power and control system 2122 applies the combination of an asymmetric waveform voltage and direct current voltage to the inner electrode 2110 via an electrical contact disposed thereon. In particular, with specific reference to FIG. 18a, the applied combination of an asymmetric waveform voltage and direct current voltage (referred to as the CV) is selected for transmitting ions of interest produced at ESI source 2092 to the mass spectrometer 2106.

Referring now to FIG. 18b, shown is a situation in which ions from an ESI source 2124 are transmitted through FAIMS 2100 and to the mass spectrometer 2106. It is assumed that the CV of transmission of the ions selected from ESI source 2092 differs substantially from the CV appropriate to the ions from ESI source 2124. Preferably, a not illustrated computer interface to the electronic power and control system 2122 of the FAIMS 2100 is used to control the timing and voltage conditions for the selection of ions from ESI source 2092 or from ESI source 2124. Of course, similar provisions are made to ensure that ions produced at the ESI source 2124 are desolvated and introduced into the FAIMS analyzer region 2108. To this end, a curtain plate 2126 having an aperture 2128 defined therethrough is disposed between ESI source 2124 and a second ion inlet 2130 into FAIMS 2100. The flow of curtain gas 2132 acts in a manner analogous to that of curtain gas flow 2102, so as to desolvate ions produced at ESI source 2124 and to introduce the desolvated ions through the second inlet 2130 and into FAIMS 2100.

By appropriate selection of operating conditions of the FAIMS 2100, ions from the ionization source 2092 and from the ionization source 2124 are transmitted, in an alternating fashion, through the FAIMS 2100 and to the mass spectrometer 2106. The system shown at FIGS. 18a and 18b has some limitations. Since only one FAIMS 2100 is provided, the ions from both ionization sources 2092 and 2124 are delivered to the mass spectrometer 2106 if both ionization sources 2092 and 2124 produce ions that are transmitted at the particular operating conditions of CV, DV, gas type, pressure, temperature, electrode spacing, etc. of the FAIMS 2100. For example, assume that the ionization source 2092 produces a reference ion for calibration of the mass scale and that the other source 2124 is in fluid communication with a reservoir of a sample solution. Assume also that the mass calibration ion is transmitted at CV=−10 volts. In operation, at various times the FAIMS 2100 is set to this CV to deliver the reference ions to the mass spectrometer 2106. Clearly, any ions that are also transmitted at CV=−10 volts from the sample source 2124 are simultaneously delivered to the mass spectrometer 2106. This is not a problem unless the sample solution contains ions that interfere with the mass calibration reference ions, by appearing at very similar mass. Even then, this is not a severe problem since the calibration solution can be prepared with the reference compound at high concentration.

Similarly, if ions of interest from the sample are transmitted at CV=−15 volts, any ions originating from the calibration solution that are transmitted at CV=−15 volts are also delivered to the mass spectrometer 2106, and thus are superimposed upon the spectrum of the sample. This is not a severe problem since the reference ions are easily identified and ignored during data processing. However, if the ions are background ions, then these ions cannot be easily identified or ignored, and therefore they will contribute to background chemical noise.

Figure 19A:
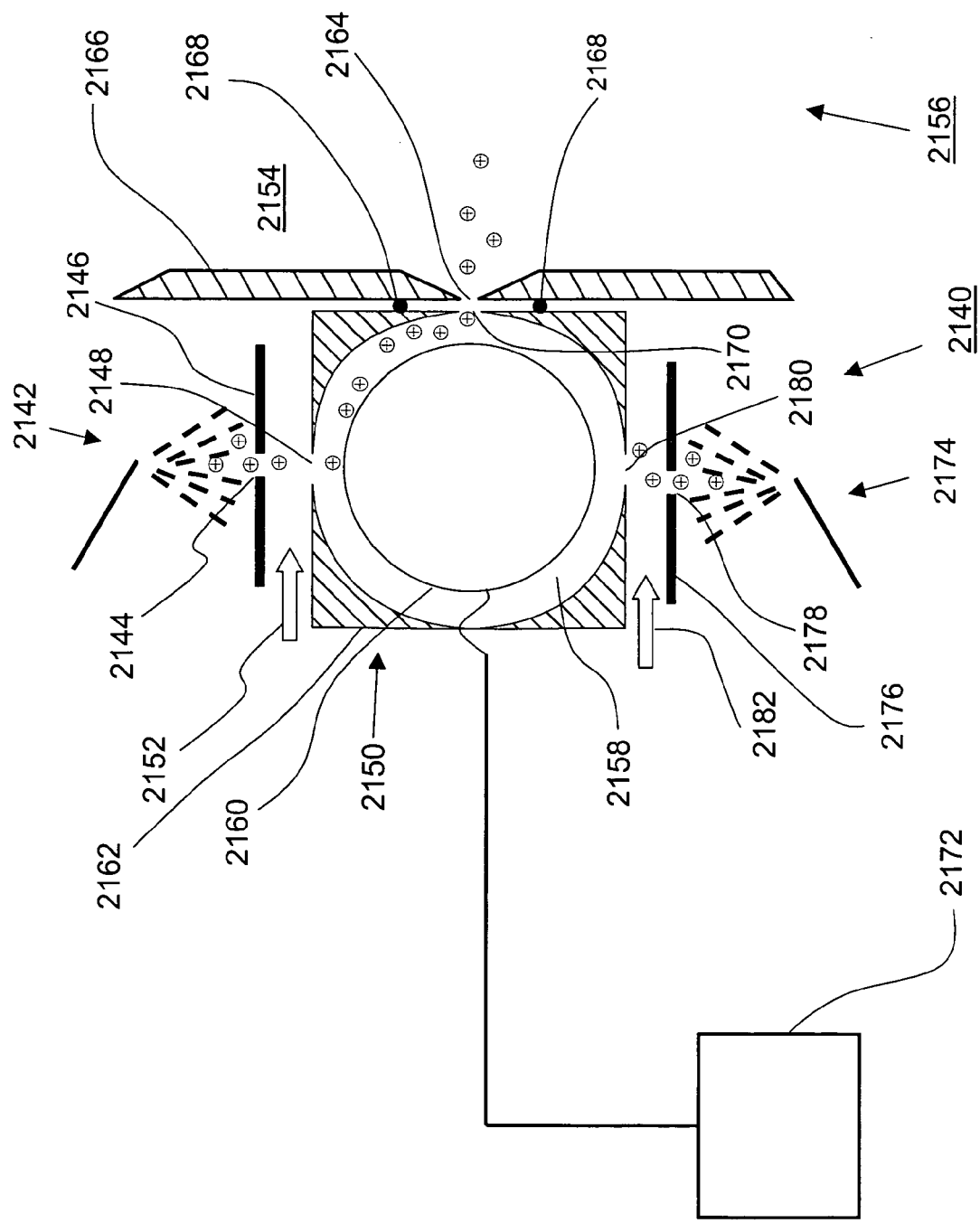
FIG. 19a is a simplified schematic diagram of another embodiment of the apparatus shown at FIG. 15a in a first mode of operation.
Figure 19B:
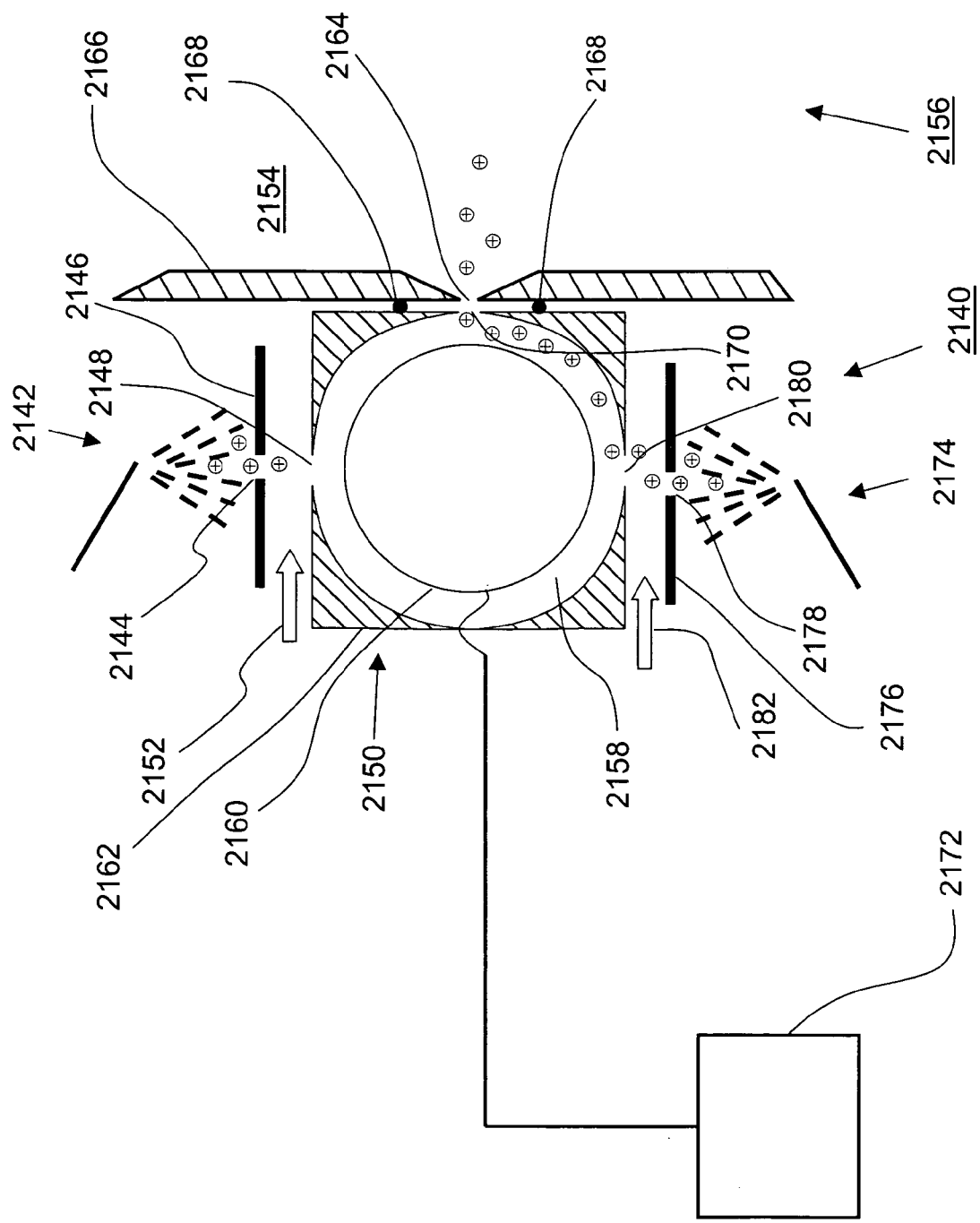
FIG. 19b is a simplified schematic diagram of another embodiment of the apparatus shown at FIG. 15a in a second mode of operation.

FIG. 19a and FIG. 19b illustrates yet another example of an embodiment 2140 of the concept shown in FIG. 15a, but with greater detail than is shown at FIG. 15a. During use, as shown at FIG. 19a, a stream of ions produced at ESI source 2142 is transmitted against a flow of desolvation gas coming out through an aperture 2144 defined within a curtain plate 2146. The ions having passed through the aperture 2144 are carried by a gas stream through a first inlet 2148 into a side-to-side version of FAIMS 2150. In particular, a curtain gas 2152 delivered to the space between the curtain plate 2146 and FAIMS 2150 divides into two streams, the first flowing out of the aperture 2144 in the curtain plate 2146 and forming the flow of desolvation gas, and the second flowing into the FAIMS 2150, being pulled through the FAIMS 2150 by a flow entering the vacuum chamber 2154 of a mass spectrometer 2156. A sub-set of ions from ESI source 2142 is selected by appropriate application of electrode voltages and gas composition, and is transmitted within an annular analyzer region 2158 between an inner FAIMS electrode 2160 and an outer FAIMS electrode 2162. The sub-set of ions is drawn through an orifice 2164 in the orifice plate 2166 of the mass spectrometer 2156 by the flow of gas into the vacuum chamber 2154. Gas-tight seals 2168 are disposed between the FAIMS 2150 and the orifice plate 2166 of the mass spectrometer 2156. As noted above, a portion of the curtain gas 2152 is pulled into the analyzer region 2158 of FAIMS 2150 and carries the ions along the analyzer region 2158 to an outlet aperture 2170 of FAIMS 2150, the outlet aperture 2170 being disposed adjacent to and in fluid communication with the orifice 2164 in orifice plate 2166 of the mass spectrometer 2156. Subsequently, this mixture of gas and ions is drawn into the vacuum chamber 2154 of the mass spectrometer 2156. Of course, an electronic power and control system 2172 applies a combination of an asymmetric waveform voltage and direct current voltage between the inner electrode 2160 and the outer electrode 2162. For instance, the electronic power and control system 2172 applies the combination of an asymmetric waveform voltage and direct current voltage to the inner electrode 2160 via an electrical contact disposed thereon. In particular, with specific reference to FIG. 19a, the applied combination of an asymmetric waveform voltage (referred to as the DV) and direct current voltage (referred to as the CV) is selected for transmitting ions produced at ESI source 2142 to the mass spectrometer 2156.

Referring now to FIG. 19b, shown is a situation in which ions from ESI source 2174 are transmitted through FAIMS 2150 and to the mass spectrometer 2156. It is assumed that the CV of transmission of the ions selected from ESI source 2142 differs substantially from the CV appropriate to the ions from ESI source 2174. Preferably, a not illustrated computer interface to the electronic power and control system 2172 of the FAIMS 2150 is used to control the timing and voltage conditions for the selection of ions from ESI source 2142 or from ESI source 2174. Of course, similar provisions are made to ensure that ions produced at the ESI source 2174 are desolvated and introduced into the FAIMS analyzer region 2158. To this end, a curtain plate 2176 having an aperture 2178 defined therethrough is disposed between ESI source 2174 and a second inlet 2180 into FAIMS 2150. The flow of curtain gas 2182 acts in a manner analogous to that of curtain gas flow 2152, so as to desolvate ions produced at ESI source 2174 and to introduce the desolvated ions through the second ion inlet 2180 and into FAIMS 2150.

Figure 20A:
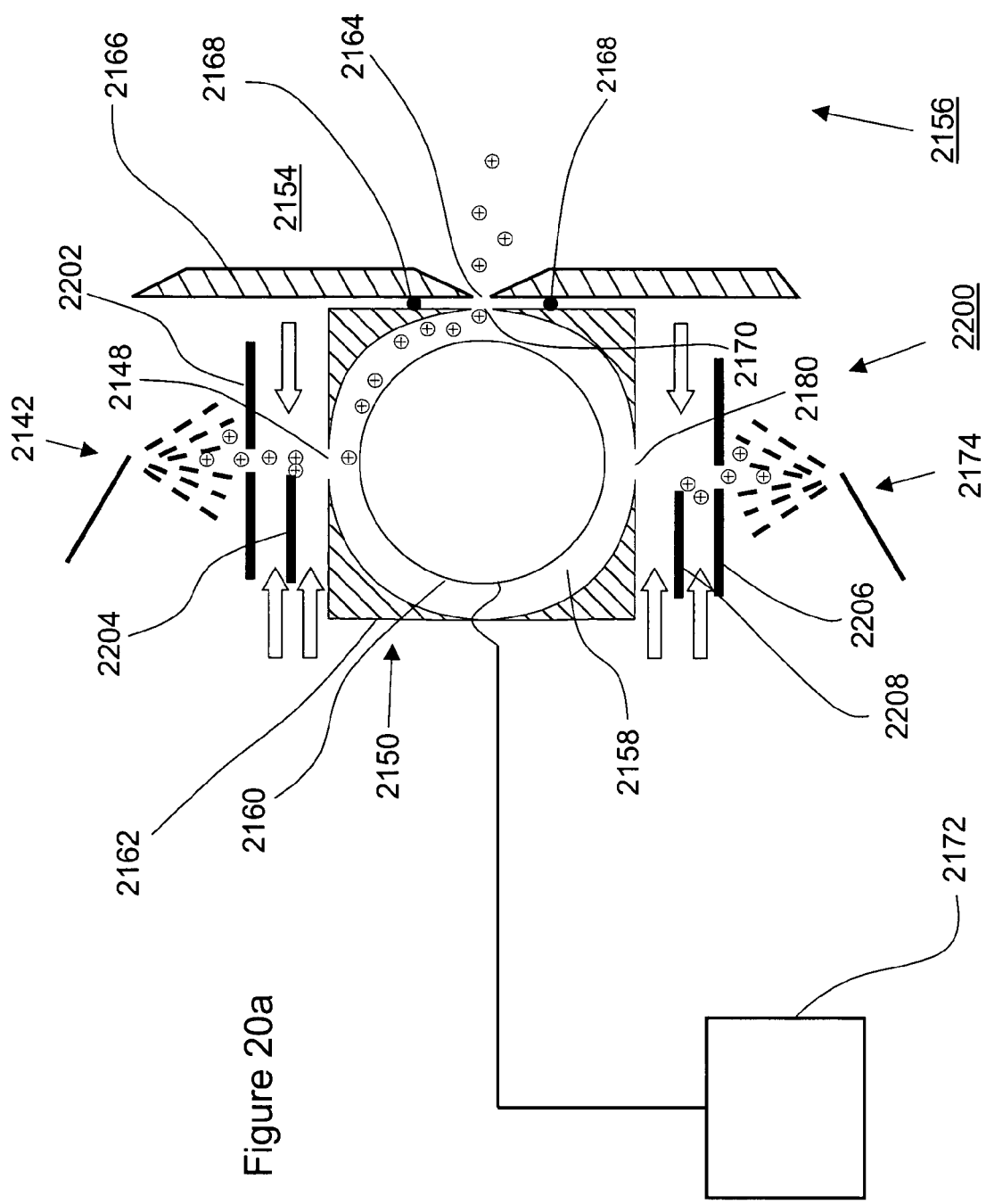
FIG. 20a is a simplified schematic diagram of an embodiment of the apparatus shown at FIG. 15b in a first mode of operation.
Figure 20B:
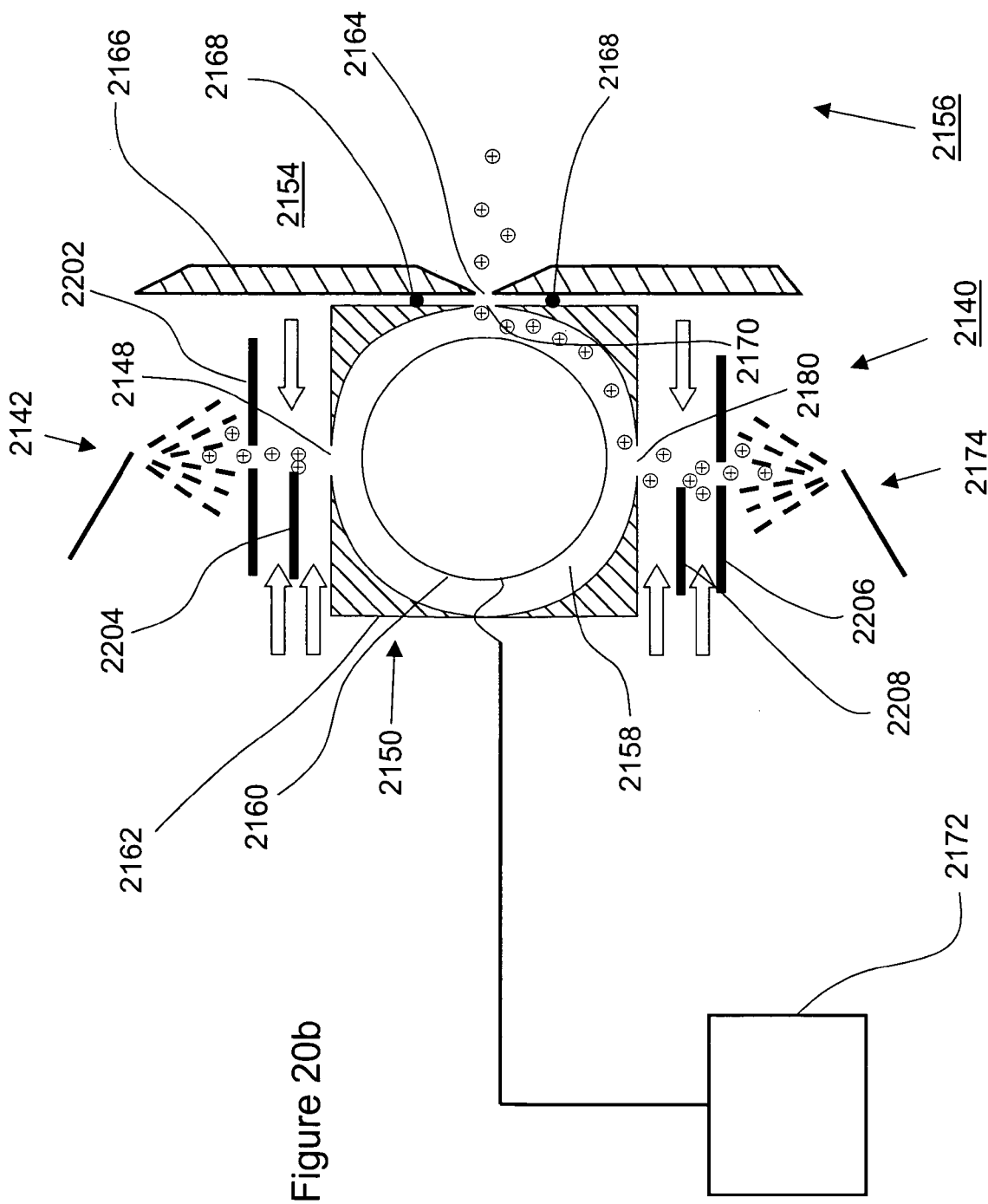
FIG. 20b is a simplified schematic diagram of an embodiment of the apparatus shown at FIG. 15b in a second mode of operation.

FIG. 20a and FIG. 20b illustrate still another example of an embodiment 2200 of the concept shown in FIG. 15b. In many respects, FIG. 20a and FIG. 20b are similar to FIG. 19a and 19b, and so similar reference numerals have been used to designate similar items, but they differ in that provision is made to gate the ions as they pass through the curtain region that separates the curtain plate from the ion inlet of the FAIMS outer electrode. A gate electrode 2204 is located between a curtain plate 2202 and the FAIMS 2150. The transit of ions between ESI source 2142 and the first ion inlet 2148 is controlled by application of voltages to the gate electrode 2204. For example, if the curtain plate 2202 is at 500 volts, and FAIMS outer electrode 2162 is at 50 volts, the application of 250 volts to the gate electrode 2204 permits ions to travel across the curtain region and into FAIMS 2150; in this case, the gate is in the 'open' state. This condition is shown schematically at FIG. 20a, where the gate electrode 2204 for ESI source 2142 is in a transmitting (i.e. open) state. Subsequently, the voltage that is applied to the gate electrode 2204 can be changed to prevent ions from passing thereby. If −500 volts is applied to the gate electrode 2204 then (assuming positive ions) the ions impact the gate electrode 2204 and fail to be transmitted into FAIMS and the gate becomes effectively 'closed'. In FIG. 20b, the gate electrode 2204 is closed at the same time a gate electrode 2208 associated with the ESI source 2174 is open. This gate system, including gate electrodes 2204 and 2208, supports selection of ions from either of the ESI sources 2142 or 2174, or from both ESI sources 2142 and 2174, simultaneously. Preferably, a computer interface to the electronic power and control system 2172 of the FAIMS 2150, similar to the not illustrated computer interface described supra, is used to control the timing and voltage conditions for the selection of ions from ESI source 2142 or from ESI source 2174.

Optionally, the gate electrodes 2204 and/or 2208 in FIG. 20a and 20b can take various forms. The gate electrodes 2204 and 2208 in these figures is a narrow wire that terminates near the ion stream that passes from the curtain plate orifice to the inlet of the outer electrode of FAIMS. The wire offers minimum interference in the flows of gas, but the voltage applied to the wire has an effect on the transmitted ions. Other types of gates may include pairs of wires to which an identical voltage is applied to each wire to transmit ions, and different voltages are applied to each wire to prevent ions from passing between the wires. A screen composed of fine wires can be a gate by control of the voltage applied to the screen. A screen offers minimum interference in the flows of gas. The gate electrodes 2204 and 2208 may optionally include two plates separated by a distance comparable to the orifice in the curtain plate or in the outer electrode of FAIMS. When an identical voltage is applied to each plate, the pair of plates allows ions to flow between the plates. If the two plates are at different voltages the ions can be prevented from traveling through the gap between the plates. The flow of curtain gas must be considered in the case of this two-plate design, to maximize ion transmission efficiency.

Further optionally, the gate electrodes 2204 and/or 2208 in FIGS. 20a and 20b take the form of the curtain plate itself, making the system look similar to the one shown at FIG. 19a and FIG. 19b. For instance, the curtain plate may be split into two halves. If the two half plates are held at an identical voltage, the ions are transmitted through the gap between the plates. If the plates are at significantly different voltages, the ions are not transmitted. The voltage ranges necessary to control the ion stream is determined empirically, and is a function of the spacing between the halves of the curtain plate, the volume and velocity of the curtain gas, as well as the temperature, gas type and gas pressure. Optionally the aperture defined within the curtain plate may be composed of several closely spaced wires, which are used as an ion gate by control of the voltage to each wire. If the adjacent wires are all at the same voltage the ions are transmitted, whereas if the adjacent wires are at different voltages the ions are not transmitted. The ion gates shown in FIG. 15b can be formed using electrodes of a wide variety of types, and the ion transmission through the gates controlled by voltages applied to one or more of the electrodes.

As discussed above, the gate in FIGS. 20a and 20b optionally takes the form of the curtain plate itself, making the system look similar to FIG. 19a and 19b. The voltages applied to the curtain plate are used to control the direction of migration of the ions between the curtain plate and the FAIMS inlet orifice in the outer electrode. If possible, the voltage applied to the curtain plate should not adversely affect the performance of the ionization source, an ESI needle spray for example. For example, assume that positive ions are sprayed by an ESI needle at +4000 volts and a curtain plate voltage of +500 volts is appropriate to move these ions from the curtain plate towards the inlet of FAIMS that is at +50 volts. The voltage difference between the curtain plate and the FAIMS is 450 volts and with a polarity that draws the ions towards the FAIMS. The voltage difference between the ESI needle and the curtain plate is 3500 volts, with polarity that moves positive ions towards the curtain plate. The flow of ions between the curtain plate and FAIMS may be reversed if the curtain plate voltage is dropped from +500 to −100 volts. The voltage difference between the curtain plate and FAIMS is 150 volts with polarity that moves positive ions away from FAIMS and towards the curtain plate. The voltage difference between the ESI needle and the curtain plate has increased from 3500 to 4100 volts, but the direction of motion of the ions remains unchanged in this region. This example illustrates use of the curtain plate voltage as the gate controlling the flow of ions into FAIMS, permitting flow of ions at a first voltage, and preventing flow at another voltage, with minimum interference in the performance of the ion source.

Figure 21A:
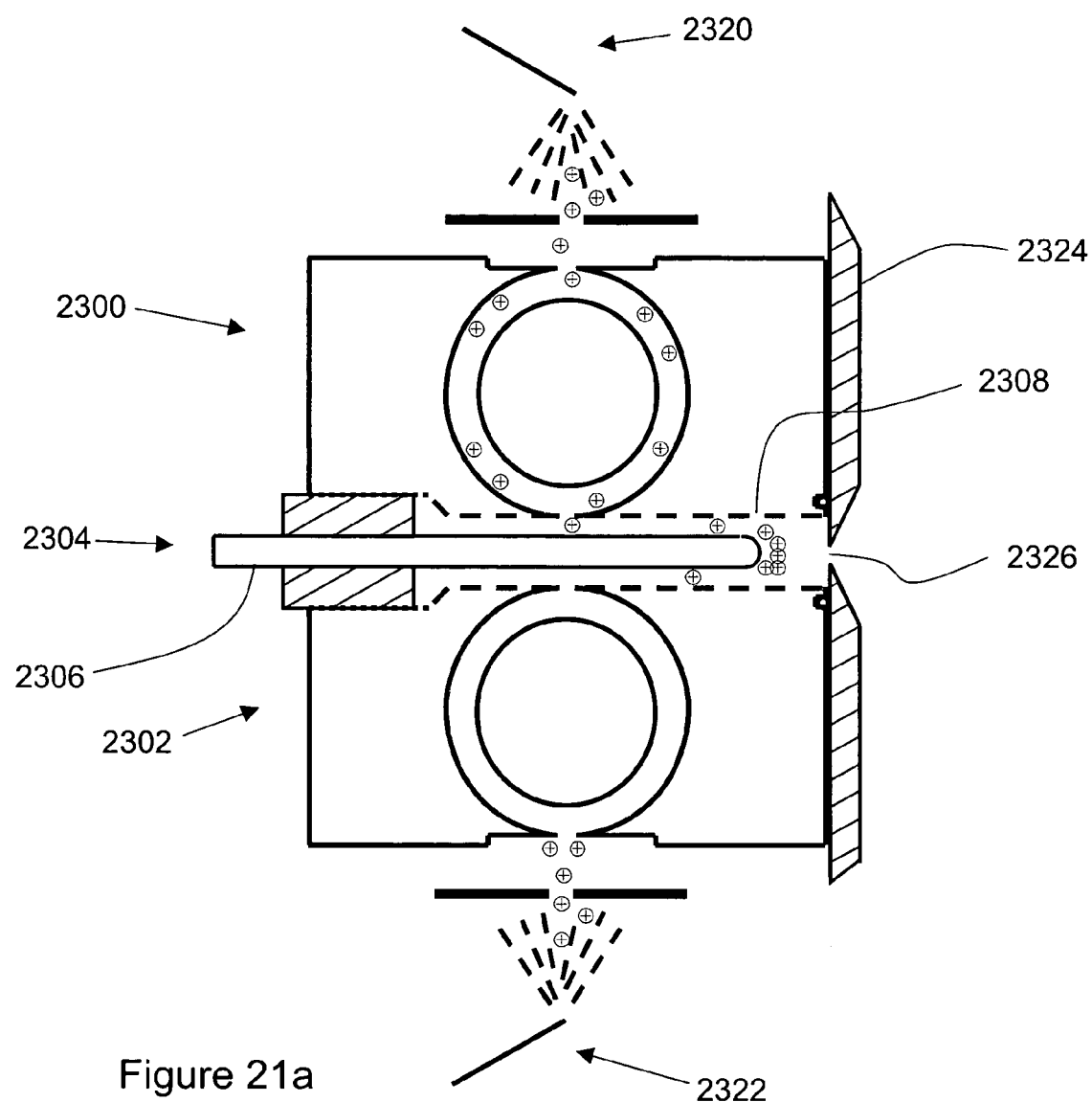
FIG. 21a is a simplified schematic diagram of an embodiment of the apparatus shown at FIG. 16 in a first mode of operation.
Figure 21B:
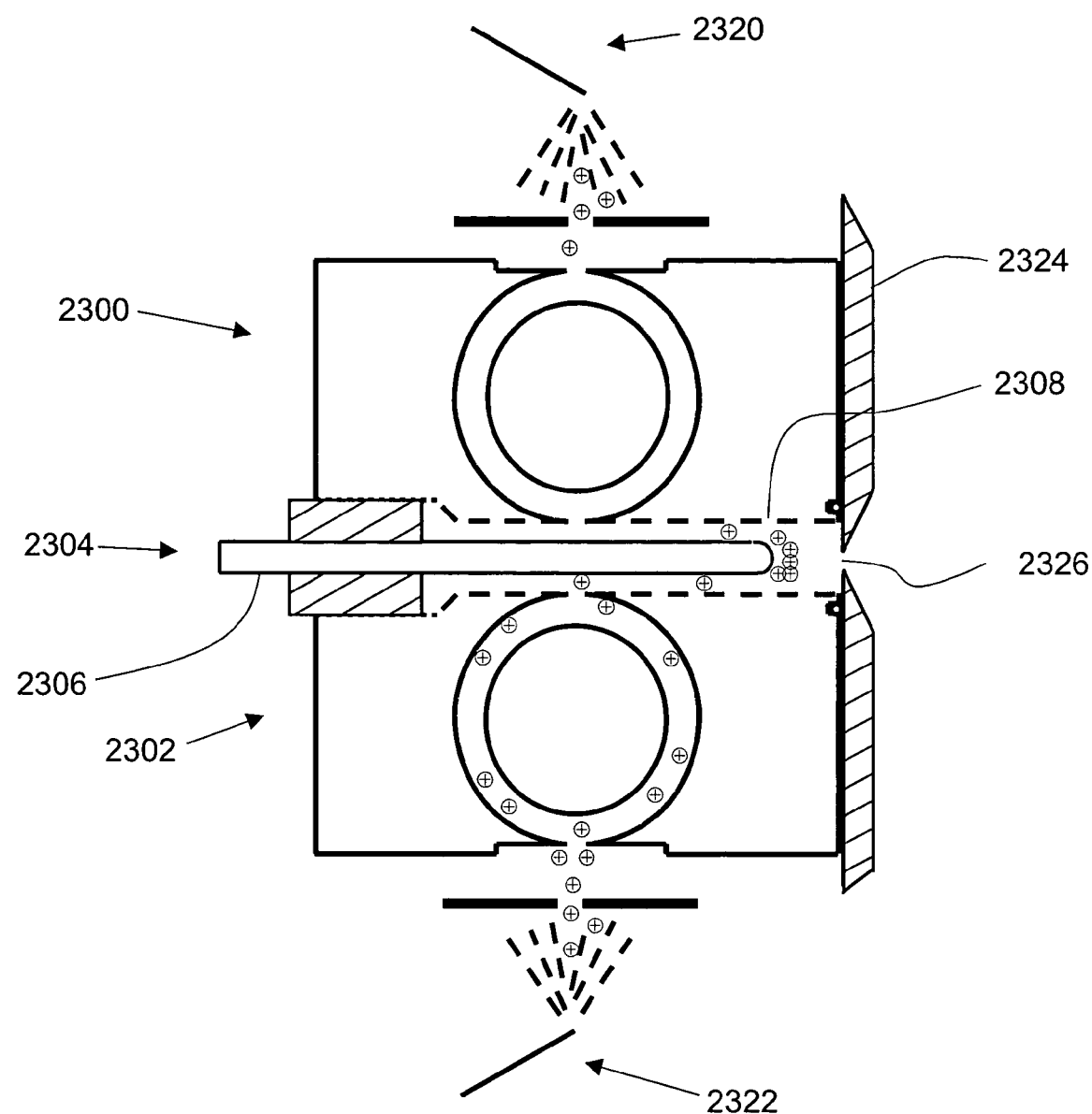
FIG. 21b is a simplified schematic diagram of an embodiment of the apparatus shown at FIG. 16 in a second mode of operation.
Figure 21C:
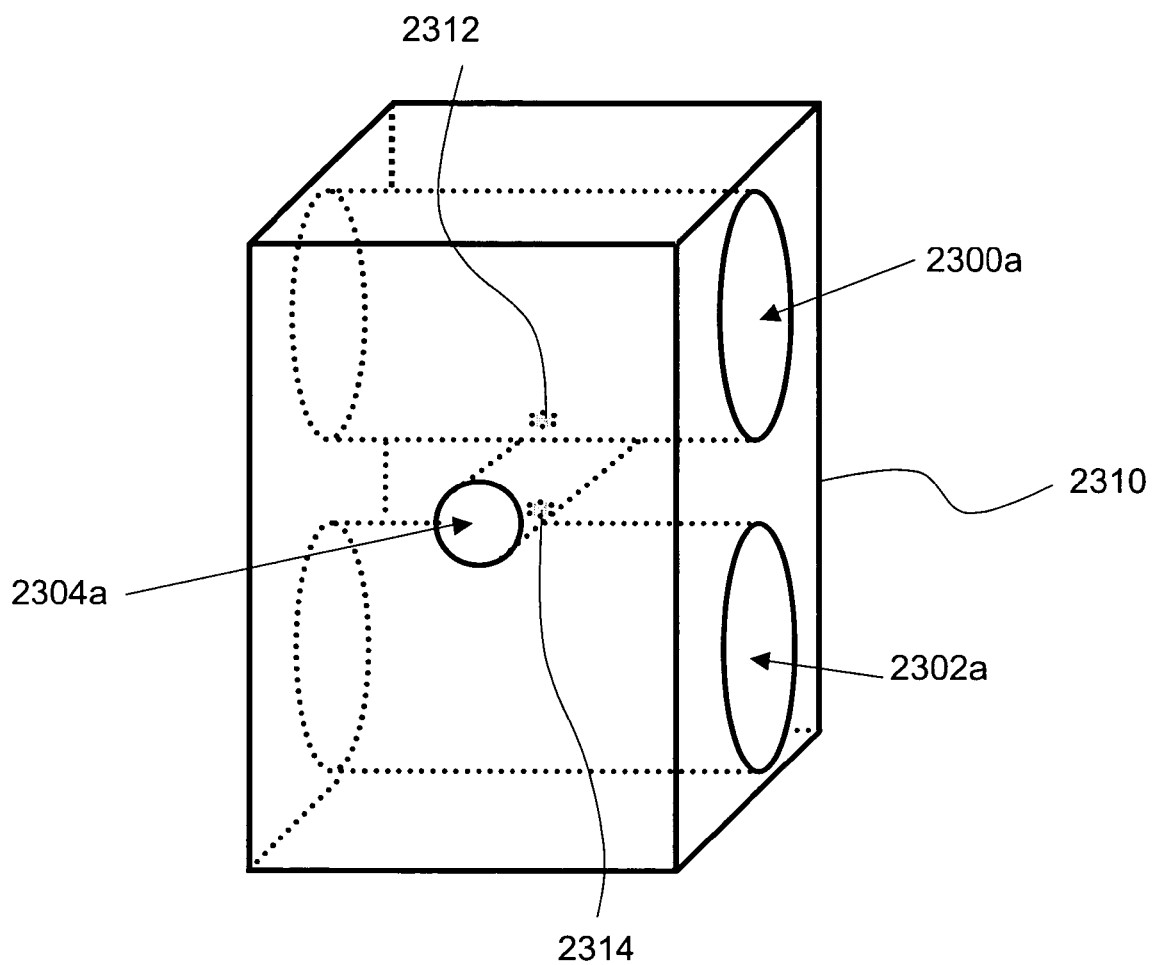
FIG. 21c is an isometric view of a unitary outer electrode member suitable for use with the embodiment shown at FIGS. 21a and 21b.

FIGS. 21a to 21c illustrate one example of an embodiment of the concept shown in FIG. 16. The system is more complex than that shown in FIGS. 18a, 18b, 19a, 19b, 20a and 20b, requiring several FAIMS coupled together. Here, two side-to-side FAIMS 2300 and 2302 are arranged to deliver ion streams into a collector FAIMS 2304 which is a trapping version of FAIMS having a domed inner electrode 2306 of narrow diameter, and a cylindrical outer electrode 2308. As shown at FIGS. 21a to 21c, the side-to-side FAIMS 2300 and 2302 have wide diameter electrodes which are suitable for high resolution separations, whereas the trapping FAIMS 2304 has narrow electrodes designed for optimum ion focusing and storage efficiency.

Referring to FIG. 21a, the stream of ions from ESI source 2320 is selected and the voltage conditions to the side-to-side FAIMS 2300 and the trapping FAIMS 2304 are both set to conditions for transmitting a selected ion from ESI source 2320. Meanwhile, by setting appropriate voltages, the ions from ESI source 2322 cannot flow to the trapping FAIMS 2304. In FIG. 21a, the ions arriving at the tip of the trapping electrode 2306 are held temporarily by a low stopping voltage applied to orifice plate 2324. The cloud of trapped ions can be released into a not illustrated mass spectrometer via an ion outlet 2326 of the trapping FAIMS 2304, to coincide, for example with the acceleration of a TOF mass spectrometer. In FIG. 21b the voltages have been changed so that the ions pass from ESI source 2322, through the side-to-side FAIMS 2302 and through the trapping FAIMS 2304. Again, the ions are optionally pulsed out of the trapping FAIMS 2304 into a not illustrated TOF mass spectrometer via an ion outlet 2326 of the trapping FAIMS 2304.

Referring to FIG. 21c, shown is simplified isometric view of an apparatus for multiplexing ions from a first ionization source and from a second ionization source. The apparatus includes the monolithic outer-electrode member 2310 including a first channel or passageway 2304a defined therethrough and open at opposite ends thereof, a second channel or passageway 2300a defined therethrough and open at opposite ends thereof, and a third channel or passageway 2302a defined therethrough and open at opposite ends thereof. The second channel or passageway 2300a is defined adjacent to the first channel or passageway 2304a and intersects with the first channel or passageway 2304a so as to form the small opening (i.e. a first orifice) 2312 therebetween, and the third channel or passageway 2302a is defined adjacent to the first channel or passageway 2304a and intersecting with the first channel or passageway 2304a so as to form the second small opening (i.e. a second orifice) 2314 therebetween. In an assembled condition, a first inner electrode (not shown in FIG. 21c) is positioned within the first channel or passageway 2304a so as to define a first annular space between an outer surface of the first inner electrode and an inner surface of the first channel or passageway 2304a. Similarly, a second not illustrated inner electrode is positioned within the second channel or passageway 2300a so as to define a second annular space between an outer surface of the second inner electrode and an inner surface of the second channel or passageway 2300a, and a third not illustrated inner electrode is positioned within the third channel or passageway 2302a so as to define a third annular space between an outer surface of the third inner electrode and an inner surface of the third channel or passageway 2302a. During use, ions introduced into the second annular space propagate through the first orifice and into the first annular space, and ions introduced into the third annular space propagate through the second orifice and into the first annular space.

Referring still to FIG. 21c, one of the open ends of the first channel or passageway 2304a defines an ion outlet orifice, and during use, ions that are introduced into the first annular space are directed towards and out of the ion outlet orifice. Preferably, one end the first inner electrode nearest the ion outlet orifice includes a terminus shaped for directing ions that are propagating within the first annular space along a direction that is generally radially inward toward a longitudinal axis of the first electrode. In this way, ions are focused for extraction from the first annular space through the small diameter ion outlet orifice.

Relating FIGS. 21a and 21b to FIG. 21c, the second channel or passageway 2300a and the second inner electrode comprise a first side-to-side FAIMS analyzer portion 2300, the third channel or passageway 2302a and the third inner electrode comprise a second side-to-side FAIMS analyzer portion 2302, and the first channel or passageway 2304a and the first inner electrode comprise a collector FAIMS 2304 which is a trapping version of FAIMS having a domed inner electrode.

A not illustrated first ionization source is also provided in fluid communication with a not illustrated first ion inlet of the first side-to-side FAIMS analyzer, for providing ions into the second annular space, and a second not illustrated ionization source is provided in fluid communication with a not illustrated second ion inlet of the second side-to-side FAIMS analyzer for providing ions into the third annular space.

The monolithic outer-electrode member 2310 is fabricated from a conductive material. Optionally, the monolithic outer-electrode member 2310 is fabricated from a non-conductive material, and the inner surface of each one of the first channel or passageway 2304a, the second channel or passageway 2300a, and the third channel or passageway 2302a includes a layer of a conductive material supported thereon.

Figure 22:
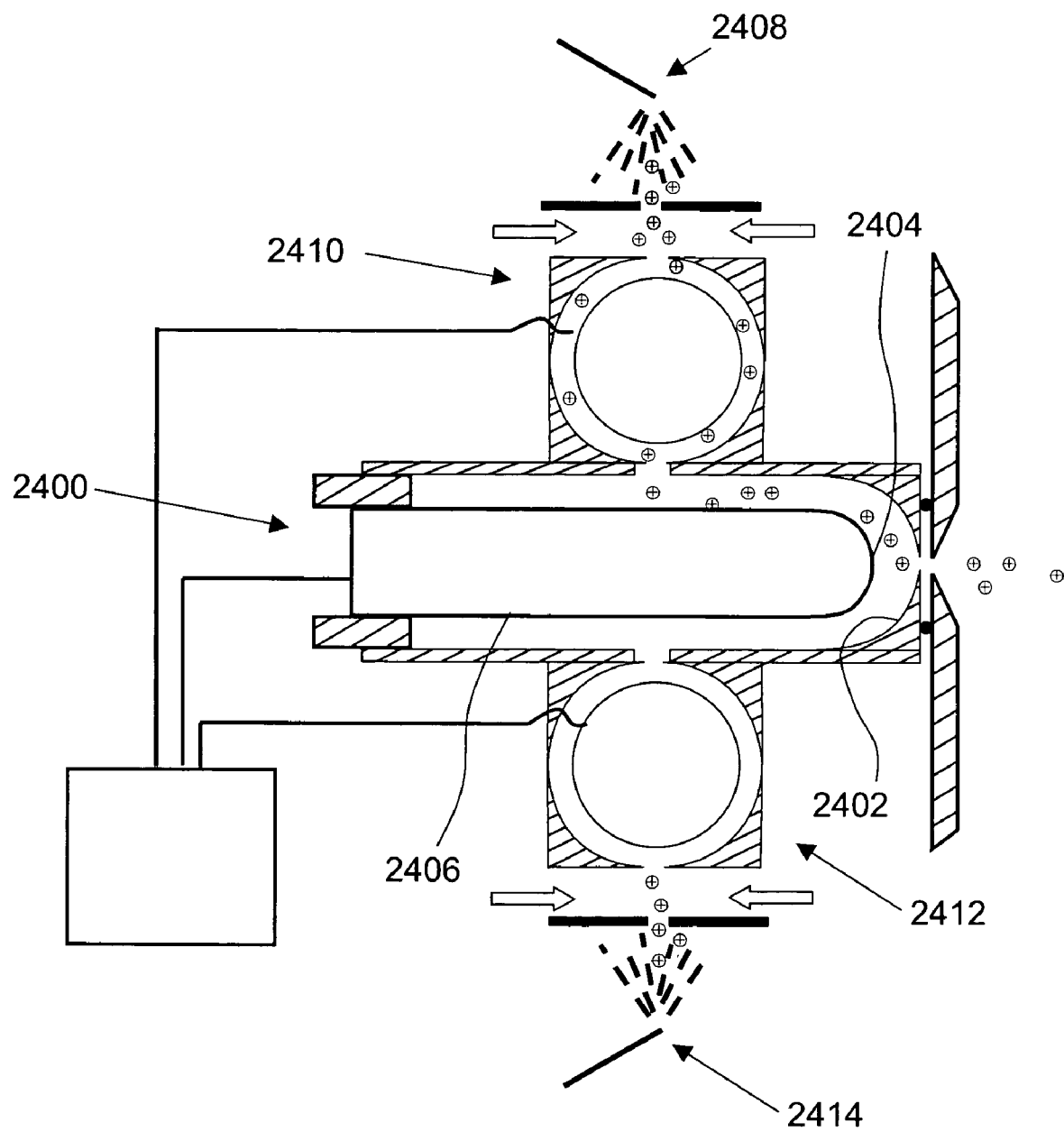
FIG. 22 is a simplified schematic diagram of an apparatus according to an embodiment of the invention.

FIG. 22 illustrates another example of an embodiment of the concept shown in FIG. 16. Unlike FIG. 21a, this system has limited capability for operation involving the storage of trapped ions, because of the wide diameter of the domed geometry collector FAIMS 2400, and because the shaped outer electrode 2402 in the vicinity of the hemispherical terminus 2404 of the domed inner electrode 2406 prevents using an orifice plate to extract ions from a trapping region proximate the terminus 2404 of the domed inner electrode 2406. The ions from ESI source 2408 are transmitted through a first side-to-side FAIMS 2410 and through the domed collector FAIMS 2400, both of which are operated with voltage, gas, and temperature conditions to transmit an ion of interest. The other side-to-side FAIMS 2412 is operating in a non-transmitting mode, several choices of which were discussed above. For example, the phase shifts between the two constituent sinusoidal waves that comprise the applied waveform have been shifted to remove the asymmetry, and the non-zero CV voltage remains applied. The other side-to-side FAIMS 2412 is re-activated to ion transmission mode by changing the phase shift back to its nominal value. In this approach, the value of CV, and the amplitudes of the sinusoidal waves need not be electrically modified, thus allowing rapid re-equilibration of applied voltages after making the electronic changes that switch the FAIMS between non-transmission mode to ion transmission mode. The phase shift is under computer control and the time required for re-establishing electrically stable conditions is very short. As described above, these transmitting conditions are established early, and after a time required for the ions to move through the side-to-side FAIMS 2412, the voltages applied to the domed collector FAIMS 2400 are changed to transmit the newly selected ions from ESI source 2414. The ions from ESI source 2408 and from ESI source 2414 are delivered sequentially to a not illustrated mass spectrometer under computer control. The software permits identification of the input ion source corresponding to any of the mass spectra so obtained.

The system shown in FIG. 22 is suitable to data acquisition with mass spectrometers requiring continuous input ion beams, including quadrupole mass spectrometers, whereas the system in FIGS. 21a–21c is better suited to instruments such as a time-of-flight mass spectrometer (TOF) which allow measurement of transient signals. Of course, optionally the system shown at FIG. 22 is used with TOF and other types of instruments.

Figure 23:
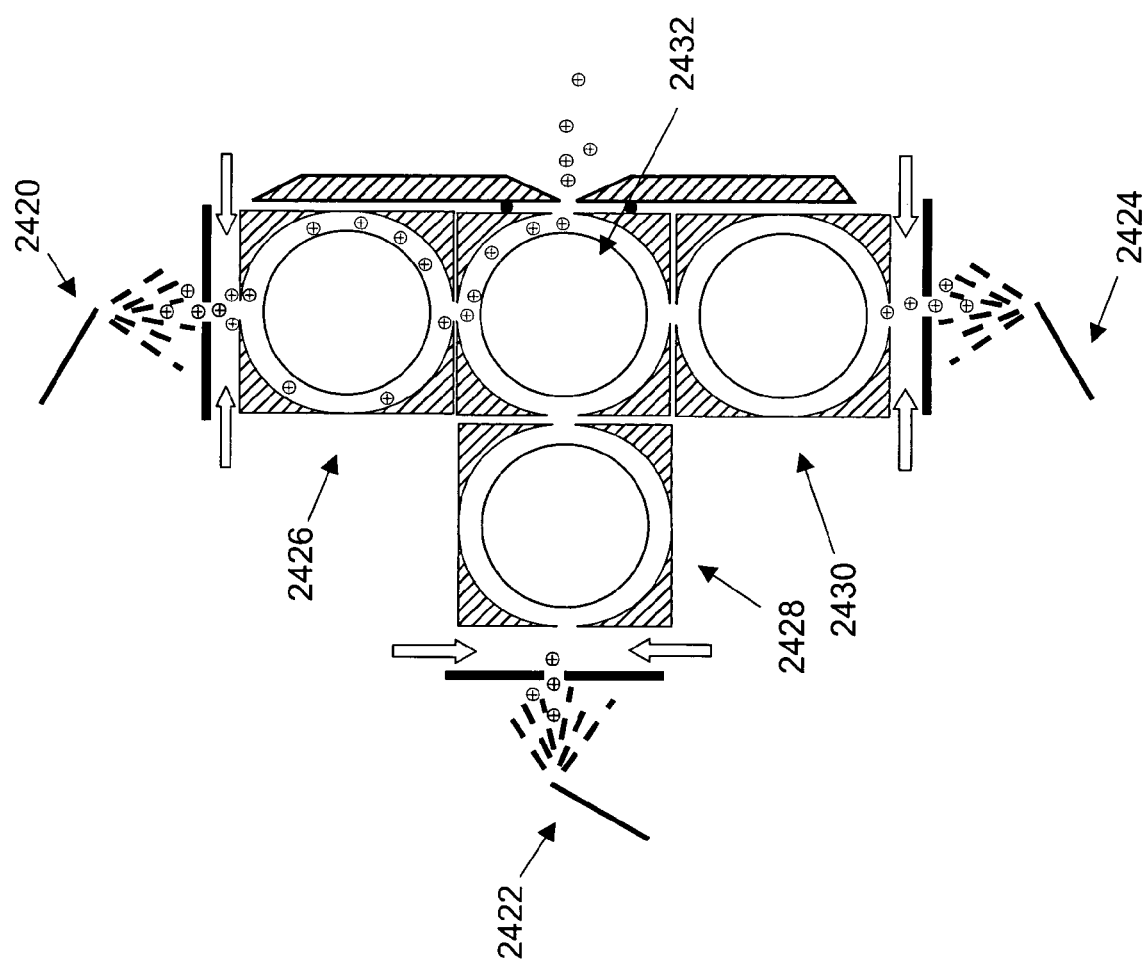
FIG. 23 is a simplified schematic diagram of an apparatus according to another embodiment of the invention.
Figure 24:
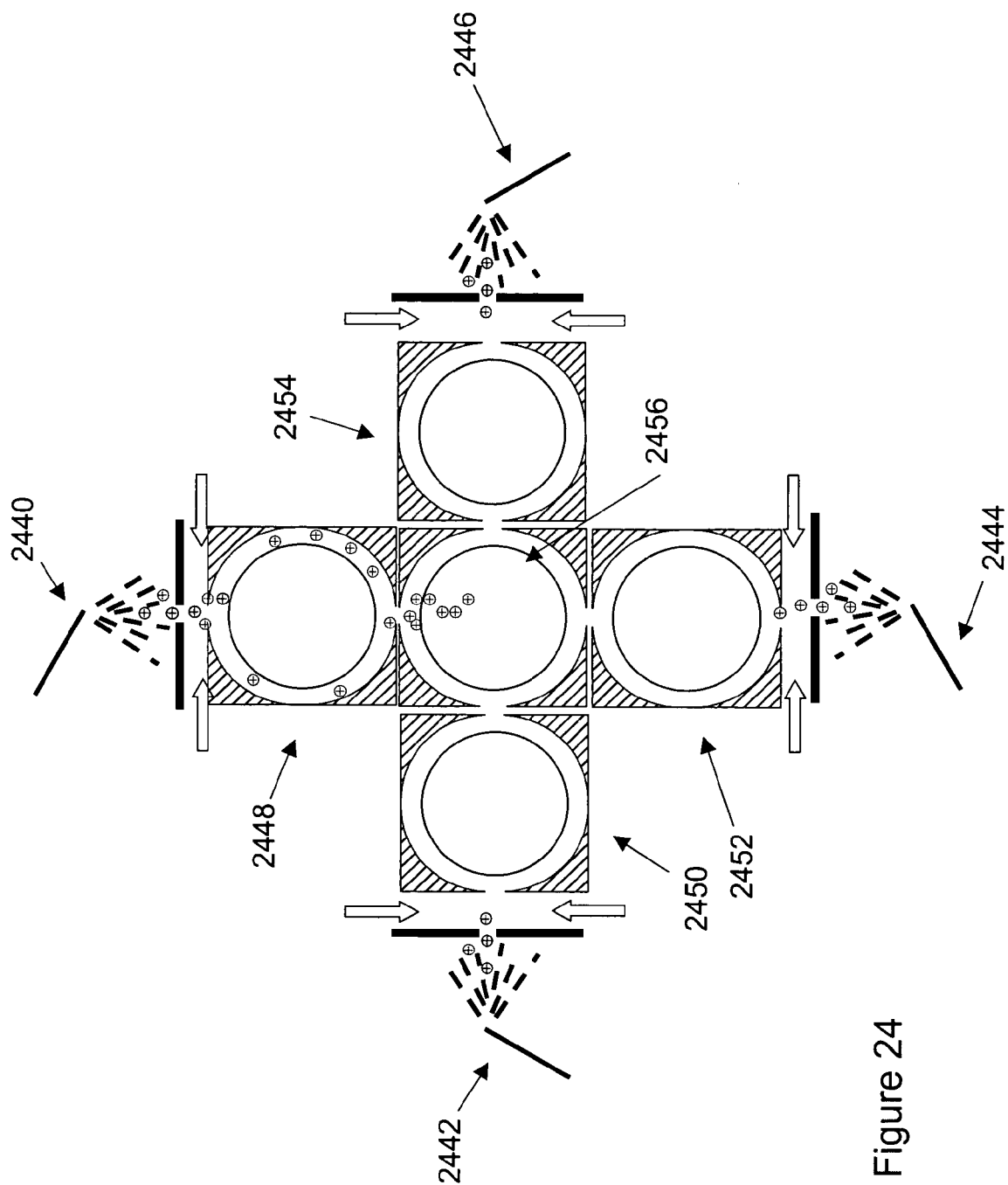
FIG. 24 is a simplified schematic diagram of an apparatus according to still another embodiment of the invention.

FIGS. 23 and 24 illustrate two additional examples of embodiments of the concept shown in FIG. 16. FIG. 23 illustrates a system comprised of three independent ion sources, all of which are electrospray sources in the instant non-limiting example. Other sources, and combinations of different types of sources are feasible.

FIG. 23 illustrates a system with three ESI sources 2420, 2422, and 2424 operating independently. Each of the three ESI sources 2420, 2422, and 2424 deliver ions each into an independent side-to-side FAIMS 2426, 2428, and 2430, respectively. Each of these FAIMS acts both as a separation device and as a selector for the ions to be delivered to a collector FAIMS 2432. The ions from a given source, for example ESI source 2420 are transmitted through a side-to-side FAIMS 2426, and into the collector FAIMS 2432 also having a side-to-side geometry. Although not shown in FIG. 23, orthogonal orientation of the channels comprising each FAIMS is advantageous from a manufacturing point of view. In an orthogonal arrangement, the openings between FAIMS appear where the channels intersect. If the channels are parallel, some difficulty appears in fabricating the channels very close together with a small opening for ion transmission between the selector FAIMS and the collector FAIMS.

The ions from each of the three ESI sources 2420, 2422, and 2424 shown in FIG. 23 are sequentially delivered to a not illustrated mass spectrometer. The ions from the non-active channels are prevented from being delivered using one of the methods described above. Minimization of the dead-time between selection of sources is critical for systems with larger numbers of input ion sources.

FIG. 24 illustrates a system with four ESI sources 2440, 2442, 2444, and 2446 operating independently. Each of the four sources 2440, 2442, 2444, and 2446 deliver ions each into an independent side-to-side FAIMS 2448, 2450, 2452, and 2454, respectively. Each of these FAIMS acts both as a separation device and as a selector for the ions to be delivered to a collector FAIMS 2456. In the device shown in FIG. 24 the collector FAIMS 2456 shown in the center, surrounded by four side-to-side devices is a domed geometry FAIMS extending in/out of the page. For example, the domed end of the collector FAIMS 2456 is facing the reader. In this diagram the ions travel towards the reader along the top side of the cylindrical inner electrode, and then converge towards the center axis as they travel around the hemispherical tip of the domed electrode. As noted above, although FIG. 24 shows electrodes that run parallel to each other, similar systems with orthogonal oriented FAIMS channels are easier to fabricate. Arrangement of two side-to-side FAIMS in orthogonal alignment to a domed FAIMS is relatively simple, shown in FIG. 22, but four side-to-side FAIMS electrodes surrounding a single FAIMS (either geometry) is more difficult, and two of the pairs may be offset longitudinally from the other two. For example, in FIG. 24, two of the Selector FAIMS (top and bottom in the Figure) may be at one plane, whereas the other two are closer or further from the domed terminus of the collector FAIMS 2456.

Figure 25:
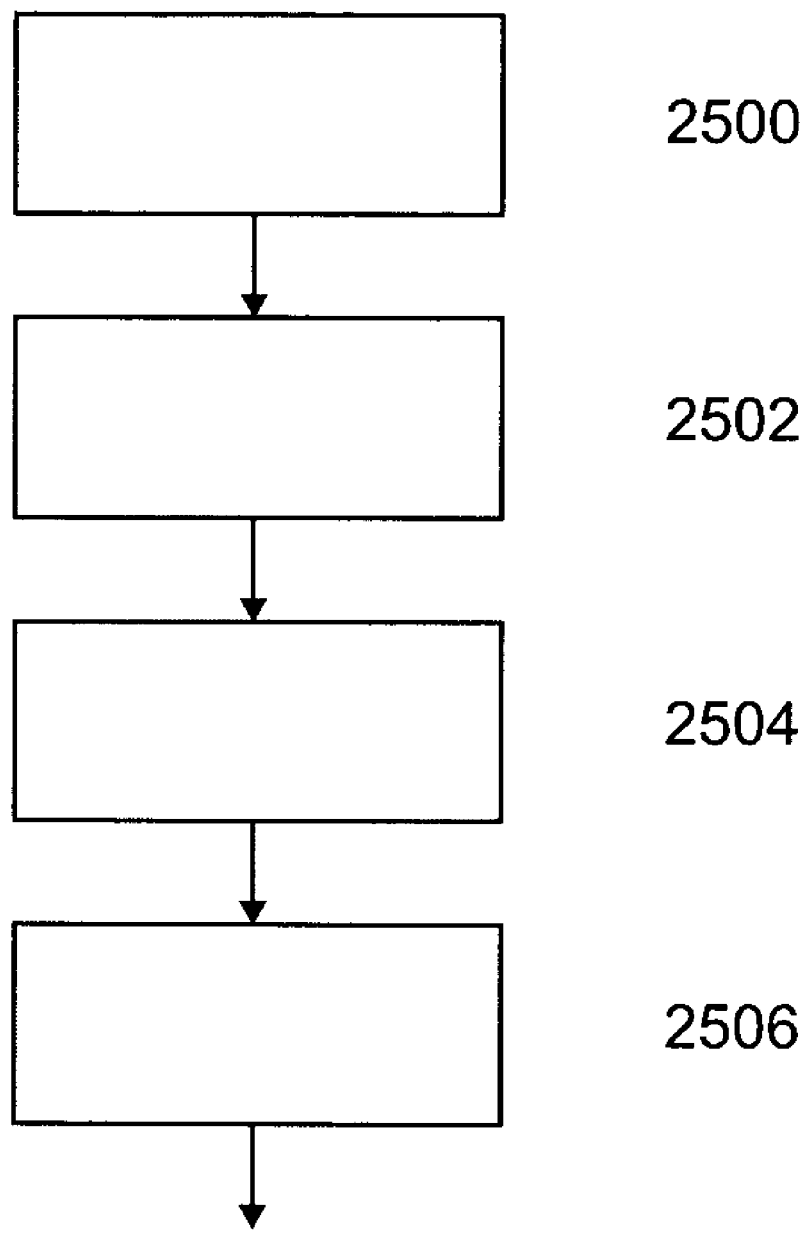
FIG. 25 is a simplified flow diagram of a method according to the instant invention; and, FIG. 26 is a simplified flow diagram of another method according to the instant invention.

Referring now to FIG. 25, shown is a simplified flow diagram of a method of multiplexing ions from a first ionization source and from a second ionization source, according to an embodiment of the instant invention. The method shown FIG. 25 is suitable for use with any of the systems shown at FIGS. 15a through 24. At step 2500, during a first period of time, first ions are provided in a substantially continuous manner from a first ionization source into an analyzer region of a FAIMS device via a first ion inlet of the FAIMS device. At step 2502, during a second period of time at least partially overlapping with the first period of time, second ions are provided in a substantially continuous manner from a second ionization source into the analyzer region of the FAIMS device via a second ion inlet of the FAIMS device. At step 2504, during a first overlapping portion of the first period of time and of the second period of time, first conditions are provided within the analyzer region of the FAIMS device for transmitting at least some of the first ions to an ion outlet of the FAIMS device and for other than transmitting the second ions to the ion outlet of the FAIMS device. At step 2506, during a second overlapping portion of the first period of time and of the second period of time, second conditions are provided within the analyzer region of the FAIMS device for transmitting at least some of the second ions to the ion outlet of the FAIMS device and for other than transmitting the first ions to the ion outlet of the FAIMS device. Accordingly, while under the influence of the first conditions, a flow of ions exiting from the analyzer region via the ion outlet of the FAIMS device comprises substantially the first ions, and while under the influence of the second conditions, a flow of ions exiting from the analyzer region via the ion outlet of the FAIMS device comprises substantially the second ions.

Optionally, the first ionization source is provided in the form of a first type of ionization source, and the second ionization source is provided in the form of a second type of ionization source that is different than the first type of ionization source. Further optionally, the first and second ionization source are provided in the form of a same type of ionization source. Some non-limiting examples of ionization sources include: an electrospray ionization source, a corona discharge ionization source, a radioactive foil ionization source, a photoionization source, a laser source, etc.

One potential application of the method shown at FIG. 25 is for introducing a reference compound for correction of the mass scale of time-of-flight mass spectrometers. In this case, one of the first ions and the second ions includes ions of an analyte species, and the other one of the first ions and the second ions includes ions of a calibration species, the calibration species for supporting a calibration process of an ion detecting device, such as a mass spectrometer. When ions of the calibration species are provided separately from the ions of the analyte species, it is preferable that the first ionization source and the second ionization source are a same type of ionization source, such as for example an electrospray ionization source. When the second ions includes the ions of the calibration species, then preferably a duration of the first overlapping portion of the first period of time and of the second period of time is selected to be longer than a duration of the second overlapping portion of the first period of time and of the second period of time. Optionally, at least one of the first ions and the second ions includes ions of an analyte species and further includes ions of a calibration species, the calibration species for supporting a calibration process of an ion detecting device, such as a mass spectrometer.

Figure 26:
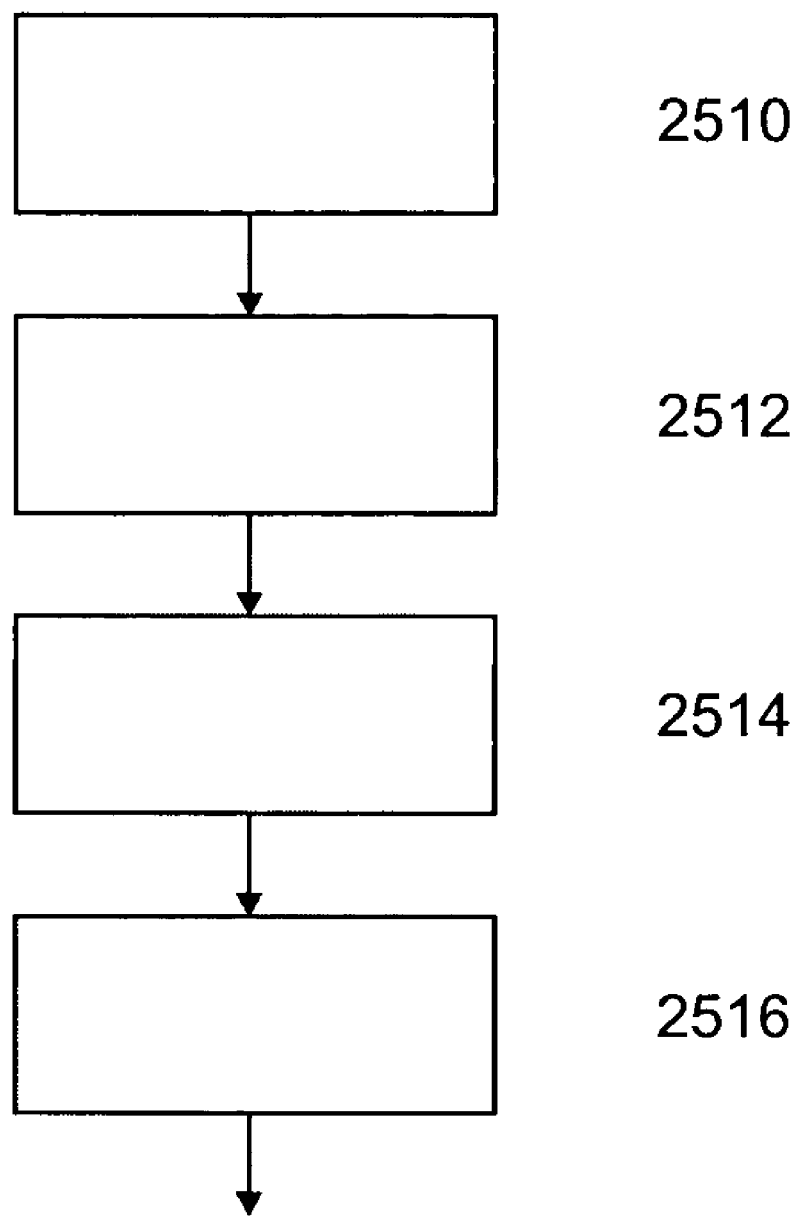

Referring now to FIG. 26, shown is a simplified flow diagram of a method of multiplexing ions from a first ionization source and from a second ionization source, according to another embodiment of the instant invention. The method shown FIG. 26 is most suitable for use with any of the systems shown at FIGS. 15b through 17c, and 20a through 24, but is also envisaged for use with any of the systems shown at FIGS. 15a through 24 under appropriate operating conditions, as discussed below.

Referring still to FIG. 26, at step 2510, during a first period of time, first ions are provided in a substantially continuous manner along a first ion flow route between a first ionization source and a first ion inlet of a first FAIMS device. At step 2512, during a second period of time overlapping with the first period of time, second ions are provided in a substantially continuous manner along a second ion flow route between a second ionization source and a second ion inlet of the first FAIMS device. At step 2514, during a first overlapping portion of the first period of time and of the second period of time, first conditions are provided within the first FAIMS device for transmitting at least some of the first ions between the first ion inlet and an ion outlet of the first FAIMS device. Still at step 2514, the trajectories of the second ions are affected so as to interrupt a flow of the second ions along the second ion flow route. At step 2516, during a second overlapping portion of the first period of time and of the second period of time, second conditions are provided within the first FAIMS device for transmitting at least some of the second ions between the second ion inlet and the ion outlet of the first FAIMS device. Still at step 2516, the trajectories of the first ions are affected so as to interrupt a flow of the first ions along the first ion flow route.

Accordingly, during the first overlapping portion of the first period of time and of the second period of time, a flow of ions exiting from the first FAIMS device via the ion outlet of the FAIMS device comprises substantially the first ions. Similarly, during the second overlapping portion of the first period of time and of the second period of time, a flow of ions exiting from the first FAIMS device via the ion outlet of the FAIMS device comprises substantially the second ions.

Optionally, the first ionization source is provided in the form of a first type of ionization source, and the second ionization source is provided in the form of a second type of ionization source that is different than the first type of ionization source. Further optionally, the first and second ionization source are provided in the form of a same type of ionization source. Some non-limiting examples of ionization sources include: an electrospray ionization source, a corona discharge ionization source, a radioactive foil ionization source, a photoionization source, a laser source, etc.

One potential application of the method shown at FIG. 26 is for introducing a reference compound for correction of the mass scale in time-of-flight mass spectrometers. In this case, one of the first ions and the second ions includes ions of an analyte species, and the other one of the first ions and the second ions includes ions of a calibration species, the calibration species for supporting a calibration process of an ion detecting device, such as a mass spectrometer. When ions of the calibration species are provided separately from the ions of the analyte species, it is preferable that the first ionization source and the second ionization source are a same type of ionization source, such as for example an electrospray ionization source. When the second ions includes the ions of the calibration species, then preferably a duration of the first overlapping portion of the first period of time and of the second period of time is selected to be longer than a duration of the second overlapping portion of the first period of time and of the second period of time. Optionally, at least one of the first ions and the second ions includes ions of an analyte species and further includes ions of a calibration species, the calibration species for supporting a calibration process of an ion detecting device, such as a mass spectrometer.

Affecting the trajectories of the first ions and of the second ions may be achieved in one of a plurality of optional ways. For instance, in systems having an ionization source disposed adjacent to a curtain plate assembly of a FAIMS ion inlet, then a flow of gas directed outwardly through a curtain plate orifice may be used to affect the trajectory of ions produced at the ionization source. Optionally, a gate electrode is disposed between the ionization source and the FAIMS ion inlet. In this case, appropriate voltages may be applied either to direct the ions that are produced at the ionization source in a direction that is away from the ion inlet, or to allow the ions to pass through to the ion inlet. In a similar approach, if a second FAIMS device is disposed between the ionization source and the ion inlet, then providing conditions within the second FAIMS that are not suitable for transmitting ions will affect the trajectories of the ions such that the ions collide with an electrode of the second FAIMS. Alternatively, conditions suitable for transmitting ions may be provided within the second FAIMS when it is desired that the ions propagate between the ionization source and the FAIMS ion inlet. In systems including plural FAIMS devices disposed one each between one of a plurality of ionization sources and one of a plurality of ion inlets, selective switching ion streams is possible. This may be done in an automated manner. For instance, a processor including a memory is provided, the memory being for storing information relating to conditions for supporting transmission of ions within the plurality of FAIMS devices. The processor is in communication with an electrical controller for automatically providing to at least one of the FAIMS devices conditions for supporting the transmission of ions therethrough, and for providing to other of the FAIMS devices conditions other than supporting the transmission of ions therethrough. In a first operating mode, the processor is for automatically providing to only one of the plurality of FAIMS devices at a time, conditions for supporting the transmission of ions therethrough. In a second operating mode, the processor is for automatically providing to more than one of the plurality of FAIMS devices at a time, conditions for supporting the transmission of ions therethrough.

Numerous other embodiments may be envisaged without departing from the spirit and scope of the invention.

What is claimed is:

1. A method of multiplexing ions from a first ionization source and from a second ionization source, comprising:
during a first period of time, providing in a substantially continuous manner first ions from a first ionization source into an analyzer region of a FAIMS device via a first ion inlet of the FAIMS device;
during a second period of time at least partially overlapping with the first period of time, providing in a substantially continuous manner second ions from a second ionization source into the analyzer region of the FAIMS device via a second ion inlet of the FAIMS device;
during a first overlapping portion of the first period of time and of the second period of time, providing first conditions within the analyzer region of the FAIMS device for transmitting at least some of the first ions to an ion outlet of the FAIMS device and for other than transmitting the second ions to the ion outlet of the FAIMS device; and,
during a second overlapping portion of the first period of time and of the second period of time, providing second conditions within the analyzer region of the FAIMS device for transmitting at least some of the second ions to the ion outlet of the FAIMS device and for other than transmitting the first ions to the ion outlet of the FAIMS device.

2. A method according to claim 1, wherein while under the influence of the first conditions, a flow of ions exiting from the analyzer region via the ion outlet of the FAIMS device comprises substantially the first ions.

3. A method according to claim 1, wherein while under the influence of the second conditions, a flow of ions exiting from the analyzer region via the ion outlet of the FAIMS device comprises substantially the second ions.

4. A method according to claim 1, wherein the first ionization source comprises a first type of ionization source, and wherein the second ionization source comprises a second type of ionization source that is different than the first type of ionization source.

5. A method according to claim 1, wherein one of the first ions and the second ions includes ions of an analyte species, and wherein the other one of the first ions and the second ions includes ions of a calibration species, the calibration species for supporting a calibration process of an ion detecting device.

6. A method according to claim 1, wherein at least one of the first ions and the second ions includes ions of an analyte species and further includes ions of a calibration species, the calibration species for supporting a calibration process of an ion detecting device.

7. A method according to claim 1, wherein providing first conditions within the analyzer region of the FAIMS device comprises providing first electrical field conditions within the analyzer region by the application of a combination of a first asymmetric waveform voltage and a first direct current voltage to at least an electrode of the FAIMS device, the combination of a first asymmetric waveform voltage and a first direct current voltage selected for supporting transmission of at least some of the first ions along a path between the first ion inlet and the ion outlet of the FAIMS device.

8. A method according to claim 7, wherein providing second conditions within the analyzer region of the FAIMS device comprises providing second electrical field conditions within the analyzer region by the application of a combination of a second asymmetric waveform voltage and a second direct current voltage to at least an electrode of the FAIMS device, the combination of a second asymmetric waveform voltage and a second direct current voltage selected for supporting transmission of at least some of the second ions along a path between the second ion inlet and the ion outlet of the FAIMS device.

9. A method according to claim 8, wherein the first asymmetric waveform voltage is substantially identical to the second asymmetric waveform voltage.

10. A method according to claim 9, wherein at least one of a polarity of the second direct current voltage and a magnitude of the second direct current voltage differs from that of the first direct current voltage.

11. A method according to claim 1, comprising extracting the at least some of the first ions and the at least some of the second ions via the ion outlet of the FAIMS device, in an alternating and intermittent manner.

12. A method according to claim 11, comprising coupling the at least some of the first ions and the at least some of the second ions extracted via the ion outlet of the FAIMS device into an ion detecting device via an ion inlet orifice of the ion detecting device.

13. A method according to claim 1, wherein each one of the first ionization source and the second ionization source comprises an electrospray ionization source.

14. A method according to claim 13, wherein the first ions include ions of an analyte species, and wherein the second ions include ions of a calibration species, the calibration species for supporting a calibration process of an ion detecting device.

15. A method according to claim 14, wherein a duration of the first overlapping portion of the first period of time and of the second period of time is selected to be longer than a duration of the second overlapping portion of the first period of time and of the second period of time.

16. A method according to claim 1, wherein providing in a substantially continuous manner first ions from a first ionization source into an analyzer region of a FAIMS device comprises receiving at least the first ions within an analyzer region of a second FAIMS device and transmitting the first ions through the analyzer region of the second FAIMS device to an ion outlet of the second FAIMS device, the ion outlet of the second FAIMS device for coupling the first ions from the second FAIMS device into the FAIMS device via the first ion inlet of the FAIMS device.

17. A method according to claim 16, wherein providing in a substantially continuous manner second ions from a second ionization source into an analyzer region of a FAIMS device comprises receiving at least the second ions within an analyzer region of a third FAIMS device and transmitting the second ions through the analyzer region of the third FAIMS device to an ion outlet of the third FAIMS device, the ion outlet of the third FAIMS device for coupling the second ions from the third FAIMS device into the FAIMS device via the second ion inlet of the FAIMS device.

18. A method of multiplexing ions from a first ionization source and from a second ionization source, comprising:
during a first period of time, providing in a substantially continuous manner first ions along a first ion flow route between a first ionization source and a first ion inlet of a first FAIMS device;
during a second period of time overlapping with the first period of time, providing in a substantially continuous manner second ions along a second ion flow route between a second ionization source and a second ion inlet of the first FAIMS device;
during a first overlapping portion of the first period of time and of the second period of time:
providing first conditions within the first FAIMS device for transmitting at least some of the first ions between the first ion inlet and an ion outlet of the first FAIMS device; and,
affecting trajectories of the second ions so as to interrupt a flow of the second ions along the second ion flow route; and,
during a second overlapping portion of the first period of time and of the second period of time:
providing second conditions within the first FAIMS device for transmitting at least some of the second ions between the second ion inlet and the ion outlet of the first FAIMS device; and,
affecting trajectories of the first ions so as to interrupt a flow of the first ions along the first ion flow route.

19. A method according to claim 18, comprising providing a second FAIMS device about a point along the second ion flow route, such that second ions propagating along the second ion flow route travel through an analyzer region defined between an ion inlet of the second FAIMS device and an ion outlet of the second FAIMS device, wherein second ions passing out through the ion outlet of the second FAIMS device are coupled into the first FAIMS device via the second ion inlet thereof.

20. A method according to claim 19, wherein affecting trajectories of the second ions so as to interrupt a flow of the second ions along the second ion flow route comprises applying at least one of an asymmetric waveform voltage and a direct current voltage to an electrode of the second FAIMS device that is unsuitable for supporting transmission of the second ions through the analyzer region of the second FAIMS device.

21. A method according to claim 20, wherein affecting trajectories of the first ions so as to interrupt a flow of the first ions along the first ion flow route comprises providing a gate electrode proximate a point along the first ion flow route, and applying a voltage to a gate electrode for moving the first ions along a direction that is away from the first ion flow route.

22. A method according to claim 19, comprising providing a third FAIMS device about a point along the first ion flow route, such that first ions propagating along the first ion flow route travel through an analyzer region defined between an ion inlet of the third FAIMS device and an ion outlet of the third FAIMS device, wherein first ions passing out through the ion outlet of the third FAIMS device are coupled into the first FAIMS device via the first ion inlet thereof.

23. A method according to claim 22, wherein affecting trajectories of the first ions so as to interrupt a flow of the first ions along the first ion flow route comprises applying at least one of an asymmetric waveform voltage and a direct current voltage to an electrode of the third FAIMS device that is unsuitable for supporting transmission of the first ions through the analyzer region of the third FAIMS device.

24. A method according to claim 22, wherein at least one of the second FAIMS device and the third FAIMS device comprises a side-to-side FAIMS device.

25. A method according to claim 22, wherein at least one of the second FAIMS device and the third FAIMS device comprises a domed-FAIMS device.

26. A method according to claim 25, wherein the second FAIMS device comprises a domed-FAIMS device, and wherein affecting trajectories of the second ions comprises trapping the second ions within a three-dimensional trapping region of the second FAIMS device.

27. A method according to claim 25, wherein the third FAIMS device comprises a domed-FAIMS device, and wherein affecting trajectories of the first ions comprises trapping the first ions within a three-dimensional trapping region of the third FAIMS device.

28. A method according to claim 18, wherein affecting trajectories of the first ions so as to interrupt a flow of the first ions along the first ion flow route comprises providing a gate electrode proximate a point along the first ion flow route, and applying a voltage to a gate electrode for moving the first ions along a direction that is away from the first ion flow route.

29. A method according to claim 28, wherein affecting trajectories of the second ions so as to interrupt a flow of the second ions along the second ion flow route comprises providing a gate electrode proximate a point along the second ion flow route, and applying a voltage to a gate electrode for moving the second ions along a direction that is away from the second ion flow route.

30. A method according to claim 18, wherein affecting trajectories of the second ions so as to interrupt a flow of the second ions along the second ion flow route comprises providing a flow of a gas out through the second ion inlet of the first FAIMS device, the flow of the gas suitable for directing the second ions away from the second ion inlet.

31. A method according to claim 18, wherein affecting trajectories of the first ions so as to interrupt a flow of the first ions along the first ion flow route comprises providing a flow of a gas out through the first ion inlet of the first FAIMS device, the flow of the gas suitable for directing the first ions away from the first ion inlet.

32. An apparatus for multiplexing ions from a first ionization source and from a second ionization source, comprising:
a monolithic outer-electrode member including a first passageway defined therethrough and open at opposite ends thereof, a second passageway defined therethrough and open at opposite ends thereof, and a third passageway defined therethrough and open at opposite ends thereof, the second passageway defined adjacent to the first passageway and intersecting with the first passageway so as to form a first orifice therebetween, and the third passageway defined adjacent to the first passageway and intersecting with the first passageway so as to form a second orifice therebetween;
a first inner electrode for being positioned within the first passageway so as to define a first annular space between an outer surface of the first inner electrode and an inner surface of the first passageway;
a second inner electrode for being positioned within the second passageway so as to define a second annular space between an outer surface of the second inner electrode and an inner surface of the second passageway; and,
a third inner electrode for being positioned within the third passageway so as to define a third annular space between an outer surface of the third inner electrode and an inner surface of the third passageway;
wherein, during use, ions introduced into the second annular space propagate through the first orifice and into the first annular space, and ions introduced into the third annular space propagate through the second orifice and into the first annular space.

33. An apparatus according to claim 32, wherein one end the first inner electrode includes a terminus shaped for directing ions that are propagating within the first annular space along a direction that is generally radially inward toward a longitudinal axis of the first electrode.

34. An apparatus according to claim 33, wherein one of the open ends of the first passageway defines an ion outlet orifice, and wherein, during use, ions that are introduced into the first annular space are directed towards and out of the ion outlet orifice.

35. An apparatus according to claim 32, wherein the first orifice is defined within a first portion of the inner surface of the second passageway, and comprising a first ion inlet defined within a second portion of the inner surface of the second passageway.

36. An apparatus according to claim 35, wherein the second orifice is defined within a first portion of the inner surface of the third passageway, and comprising a second ion inlet defined within a second portion of the inner surface of the third passageway.

37. An apparatus according to claim 36, wherein a first line defined between the first ion inlet and the first orifice approximately bisects the second passageway, and wherein a second line defined between the second ion inlet and the second orifice approximately bisects the third passageway.

38. An apparatus according to claim 36, wherein the second passageway and the second inner electrode comprise a first side-to-side FAIMS analyzer portion, the third passageway and the third inner electrode comprise a second side-to-side FAIMS analyzer portion, and the first passageway and the first inner electrode comprise a domed FAIMS analyzer portion.

39. An apparatus according to claim 36, comprising a first ionization source in fluid communication with the first ion inlet for providing ions into the second annular space, and comprising a second ionization source in fluid communication with the second ion inlet for providing ions into the third annular space.

40. An apparatus according to claim 32, wherein the monolithic outer-electrode member is fabricated from a conductive material.

41. An apparatus according to claim 32, wherein the inner surface of at least one of the first passageway, the second passageway, and the third passageway comprises a layer of a conductive material.

42. An apparatus according to claim 32, wherein a longitudinal axis of the first passageway is about orthogonal to a longitudinal axis of both of the second passageway and of the third passageway, and wherein the longitudinal axis of the second passageway is about parallel to the longitudinal axis of the third passageway.

43. An apparatus for multiplexing ions from a plurality of ionization sources, comprising:
  a first FAIMS analyzer including an inner electrode and an outer electrode defining an annular space therebetween, the outer electrode having a plurality of spaced-apart ion inlet orifices and a single ion outlet orifice;
  a plurality of other FAIMS analyzers disposed adjacent to the first FAIMS analyzer, each FAIMS analyzer of the plurality of other FAIMS analyzers having a single ion outlet orifice in communication with one ion inlet orifice of the plurality of ion inlet orifices of the first FAIMS analyzer, and each FAIMS analyzer having a single ion inlet orifice for supporting introduction of ions thereto; and,
  an electrical controller in communication with the first FAIMS analyzer, for providing conditions within the first FAIMS analyzer for supporting transmission therethrough of at least some of the ions introduced into the first FAIMS analyzer from at least one FAIMS analyzer of the plurality of other FAIMS analyzers.

44. An apparatus according to claim 43, wherein each FAIMS analyzer of the plurality of other FAIMS analyzers comprises a non-trapping FAIMS analyzer.

45. An apparatus according to claim 44, wherein at least one of the inner electrode of the first FAIMS analyzer and the outer electrode of the first FAIMS analyzer includes an electrical contact for connection to the electrical controller, for receiving an asymmetric waveform voltage and a direct current voltage therefrom for establishing an electrical field within the first FAIMS analyzer, the electrical field for providing conditions within the first FAIMS analyzer for supporting transmission of at least some of the ions introduced into the first FAIMS analyzer from at least one non-trapping FAIMS analyzer of the plurality of other FAIMS analyzers.

46. An apparatus according to claim 45, wherein each non-trapping FAIMS analyzer of the plurality of other FAIMS analyzers comprises an inner electrode and an outer electrode defining an annular space therebetween.

47. An apparatus according to claim 46, wherein at least one of the inner electrode and the outer electrode of each non-trapping FAIMS analyzer of the plurality of other FAIMS analyzers includes an electrical contact for connection to the electrical controller, for receiving an asymmetric waveform voltage and a direct current voltage therefrom for establishing an electrical field within at least one of the non-trapping FAIMS for providing conditions for supporting transmission therethrough of at least some of the ions introduced into the at least one of the non-trapping FAIMS.

48. An apparatus according to claim 47, comprising a processor including a memory, the memory for storing information relating to conditions for supporting transmission of ions within the non-trapping FAIMS analyzers of the plurality of other FAIMS analyzers, the processor in communication with the electrical controller for automatically providing to at least one of the non-trapping FAIMS analyzers conditions for supporting the transmission of ions therethrough, and for providing to other of the non-trapping FAIMS analyzers conditions other than supporting the transmission of ions therethrough.

49. An apparatus according to claim 48, wherein in a first operating mode the processor is for automatically providing to only one of the non-trapping FAIMS analyzers at a time, conditions for supporting the transmission of ions therethrough.

50. An apparatus according to claim 49, wherein in a second operating mode the processor is for automatically providing to more than one of the non-trapping FAIMS analyzers at a time, conditions for supporting the transmission of ions therethrough.

51. An apparatus according to claim 44, wherein the inner electrode of the first FAIMS analyzer comprises a generally cylindrical electrode body having a length, the generally cylindrical electrode body being substantially circular in a cross-section taken in a plane normal to the length.

52. An apparatus according to claim 51, wherein the inner electrode includes a domed terminus.

53. An apparatus according to claim 51, wherein the first FAIMS analyzer comprises a side-to-side FAIMS analyzer.

54. An apparatus according to claim 51, wherein at least one of the non-trapping FAIMS analyzers of the plurality of other FAIMS analyzers comprises a domed-FAIMS analyzer.

55. An apparatus according to claim 51, wherein at least one of the non-trapping FAIMS analyzers of the plurality of other FAIMS analyzers comprises a side-to-side FAIMS analyzer.

* * * * *